United States Patent
Sidorenko et al.

(10) Patent No.: US 11,913,004 B2
(45) Date of Patent: *Feb. 27, 2024

(54) PLANT PROMOTER FOR TRANSGENE EXPRESSION

(71) Applicant: CORTEVA AGRISCIENCE LLC, Indianapolis, IN (US)

(72) Inventors: Lyudmila Sidorenko, Johnston, IA (US); Cory M. Larsen, Zionsville, IN (US); Geny Anthony, Urbandale, IA (US); Shreedharan Sriram, Waukee, IA (US); Holly Jean Butler, Indianapolis, IN (US)

(73) Assignee: CORTEVA AGRISCIENCE, LLC, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/068,619

(22) Filed: Dec. 20, 2022

(65) Prior Publication Data

US 2023/0332167 A1 Oct. 19, 2023

Related U.S. Application Data

(63) Continuation of application No. 17/538,437, filed on Nov. 30, 2021, now Pat. No. 11,560,570, which is a continuation of application No. 16/763,406, filed as application No. PCT/US2018/058337 on Oct. 31, 2018, now Pat. No. 11,274,311.

(60) Provisional application No. 62/587,034, filed on Nov. 16, 2017.

(51) Int. Cl.
*C12N 15/82* (2006.01)

(52) U.S. Cl.
CPC .............................. *C12N 15/8216* (2013.01)

(58) Field of Classification Search
None
See application file for complete search history.

(56) References Cited

U.S. PATENT DOCUMENTS 9,725,729 B2 * 8/2017 Abbitt ................ C12N 15/8216
11,560,570 B2 * 1/2023 Sidorenko .......... C12N 15/8216

* cited by examiner

*Primary Examiner* — Cynthia E Collins

(57) ABSTRACT

This disclosure concerns compositions and methods for promoting transcription of a nucleotide sequence in a plant or plant cell, employing a promoter from a GmTEFs1 gene. Some embodiments relate to a promoter or a 5' UTR from a GmTEFs1 gene that functions in plants to promote transcription of operably linked nucleotide sequences. Other embodiments relate to a 3' UTR or a terminator from a GmTEFs1 gene that functions in plants to promote transcription of operably linked nucleotide sequences.

9 Claims, 1 Drawing Sheet

Specification includes a Sequence Listing.

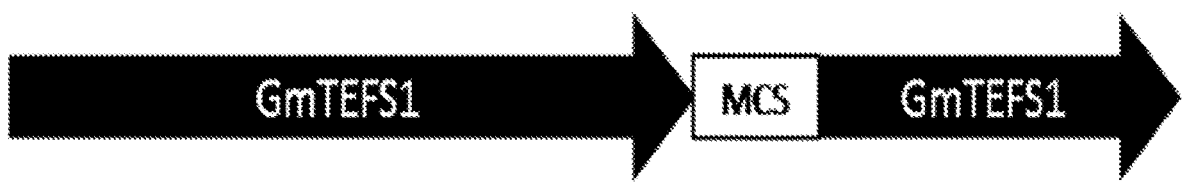

SEQUENCE LISTING

```
Sequence total quantity: 28
SEQ ID NO: 1            moltype = DNA  length = 2006
FEATURE                 Location/Qualifiers
misc_feature            1..2006
                        note = Synthetic GmTEFs1 (promoter/5'UTR and terminator
                        joined by multiple cloning site)
source                  1..2006
                        mol_type = other DNA
                        organism = synthetic construct
SEQUENCE: 1
cccagcattt gccacgttcg aacgtgagcc aaaacgatgt cgttacaata tcttaaccta   60
gccgaaacga tgtcgtggta actcataata tcgcagcctt ctgtttcgtc cttgcccaat  120
gccaactgga ctacgccgaa cccacaaaac ccgacatccg cgcgaaccaa agcgcgtgac  180
gccaaattgc tcaaaccaca aaggaaacaa aggcgcgtta ataacacgcg ctatcccacg  240
cgtgttaagc acagtaacgt tcaacaaaga gaagcagggt ataatgggaa accaaagaga  300
aacctaaggc cattatggga aacaaaaagt agctcactca ttataaaatt caagtaaccc  360
tagttttcat catcactctg ctgcctcgct ctgtttctgt ctctgtgttt gcggctgagg  420
attccgaacg agcgaccttc ttcgtttctc gcaaaggtaa cagcctctgc tcttgtctct  480
tccattcgat ccatgcctgt ctcttcttta cgatgatgtt tcttcggtgt atgtttattt  540
atttatttat ttatgcttta tgttgtgaat gttcggttgt tttgtttcgc tttgcttttg  600
tggattctat tggttttttga atcagttaat cggaagagat tttcgagttg ttttgtgttt  660
tggaggtgaa tcttttttgtt gaggtcgcag atctgttgat tttgtgtcat aaacgtgcga  720
ctctgtttga tttttttacga ggttatgacg ttttggttgt tttattatgg atctgttaag  780
gcagaaccat gatttatgtt tatgttcgtt tacacgatta aattttcttg taacacgatg  840
aagtttttttt aaacacgttg aaggagtctt gttgatatga atttgtcgat tgtttttttg  900
tggttttgtt ctcacgttat caagcgtaat cttttactat gtacgcgaac atatctagat  960
ctagcagagc ttttttttttt tttaattctt tgtgaagctt ttgaaatatg aaatttgttt 1020
ttcaaatttt ttttttaattt attgaaaaca ctgtggatac tgaataaggt tctatgtatg 1080
atgcgaacca tgtttgatat gtttgttttt gttgttccat atggattttt ctgttagatt 1140
tccatatgct tttgagtttg ttttttgctgt tacagattga tttacttttt agaatatttc 1200
tcttggcttt cactgtttta gaaattttttt gttattggta actataaatg tgtgaatttg 1260
gattatacct ttaccttgtt atttagttgt gtgataattt ggtttatagt tatttttgagt 1320
tctgactcgt gtttctttga attgattcca gtttaagtca tcggatccac acgacaccat 1380
ggtgagtagt tagcttaatc acttaggtca ccgagctctt gcatttgggc aattttgcta 1440
gcacatgtga tcatcatcgt ggttactcct ttatagtagt tttatccttg cagagtctta 1500
ggtgtttttgt ttaagttata tttttaagtt tctgccgatt tcatgtagcc gtaactttca 1560
aaactaggtt cttgatcggc ggtggtcaat tttcattgct gtttgttttt gatgagtact 1620
gttttttgtt ttgatggtaa gaagagtctg agatatttcg aatttcacaa gcagctatag 1680
ggttttagtc catttccttt gctgctgagg gatgtttttaa gttgcattta atttataacg 1740
aagtttttata aactgtttat ggtttaaagg ctattattct ttaattttgt tgttgaagta 1800
atgtgagtgg gaggtgcgct tgagctgtgt ggacgtagtt agctcttaat tatgcgatcg 1860
tagattcgta gttgcactaa tgaacaattg ttgccatgtt ttatctttca agagtacctg 1920
tcaccaatta cgcaatccat tcttatgcaa tattattgat tgataaataa aaaagaatac 1980
gcaggccaat atattgttgt ataaca                                      2006
```

| SEQ ID NO: 2 | moltype = DNA   length = 371 |
| --- | --- |
| FEATURE | Location/Qualifiers |
| misc_feature | 1..371 |
| | note = Synthetic GmTEFs1 promoter |
| source | 1..371 |
| | mol_type = other DNA |
| | organism = synthetic construct |

SEQUENCE: 2

| | | |
|---|---|---|
| cccagcattt gccacgttcg aacgtgagcc aaaacgatgt cgttacaata tcttaaccta | 60 |
| gccgaaacga tgtcgtggta actcataata tcgcagcctt ctgtttcgtc cttgcccaat | 120 |
| gccaactgga ctacgccgaa cccacaaaac ccgacatccg cgcgaaccaa agcgcgtgac | 180 |
| gccaaattgc tcaaaccaca aaggaaacaa aggcgcgtta ataacacgcg ctatcccacg | 240 |
| cgtgttaagc acagtaacgt tcaacaaaga gaagcagggt ataatgggaa accaaagaga | 300 |
| aacctaaggc cattatggga aacaaaaagt agctcactca ttataaaatt caagtaaccc | 360 |
| tagttttcat c | 371 |

| SEQ ID NO: 3 | moltype = DNA   length = 991 |
| --- | --- |
| FEATURE | Location/Qualifiers |
| source | 1..991 |
| | mol_type = other DNA |
| | organism = Glycine max |

SEQUENCE: 3

| | |
|---|---|
| atcactctgc tgcctcgctc tgtttctgtc tctgtgtttg cggctgagga ttccgaacga | 60 |
| gcgaccttct tcgtttctcg caaaggtaac agcctctgct cttgtctctt ccattcgatc | 120 |
| catgcctgtc tcttctttac gatgatgttt cttcggtgta tgtttattta tttatttatt | 180 |
| tatgctttat gttgtgaatg ttcggttgtt tgtttcgct ttgtcttttgt ggattctatt | 240 |
| ggttttgaa tcagttaatc ggaagagatt ttcgagttgt tttgtgtttt ggaggtgaat | 300 |
| cttttttgttg aggtcgcaga tctgttgatt ttgtgtcata aacgtgcgac tctgtttgat | 360 |
| tttttacgag gttatgacgt tttggttgtt ttattatgga tctgttaagg cagaaccatg | 420 |
| atttatgttt atgttcgttt acacgattaa attttcttgt aacacgatga agtttttta | 480 |
| aacacgttga aggagtcttg ttgatatgaa tttgtcgatt gttttttgt ggttttgttc | 540 |
| tcacgttatc aagcgtaatc ttttactatg tacgcgaaca tatctagatc tagcagagct | 600 |
| tttttttttt ttaattcttt gtgaagcttt tgaaatatga aatttgtttt tcaaattttt | 660 |
| ttttaattta ttgaaaacac tgtggatact gaataaggtt ctatgtatga tgcgaaccat | 720 |
| gtttgatatg ttttgttttg ttgttccata tggatttttc tgttagattt ccatatgcat | 780 |
| ttgagtttgt ttttgctgtt acagattgat ttactttta gaatatttct cttggctttc | 840 |
| actgttttag aaattttttg ttattggtaa ctataaatgt gtgaatttgg attataccttt | 900 |
| taccttgtta tttagttgtg tgataatttg gtttatagtt attttgagtt ctgactcgtg | 960 |
| tttctttgaa ttgattccag tttaagtcat c | 991 |

| SEQ ID NO: 4 | moltype = DNA   length = 364 |
| --- | --- |
| FEATURE | Location/Qualifiers |
| source | 1..364 |
| | mol_type = other DNA |
| | organism = Glycine max |

SEQUENCE: 4

| | |
|---|---|
| ttgcatttgg gcaattttgc tagcacatgt gatcatcatc gtggttactc ctttatagta | 60 |
| gttttatcct tgcagagtct taggtgtttt gtttaagtta tattttttaag tttctgccga | 120 |
| tttcatgtag ccgtaacttt caaaactagg ttcttgatcg gcgtggtca attttcattg | 180 |
| ctgtttgttt ttgatgagta ctgttttttg ttttgatggt aagaagagtc tgagatattt | 240 |
| cgaatttcac aagcagctat agggttttag tccatttcct ttgctgctga gggatgtttt | 300 |
| aagttgcatt taatttataa cgaagtttta taaactgttt atggtttaaa ggctattatt | 360 |
| cttt | 364 |

| SEQ ID NO: 5 | moltype = DNA   length = 588 |
| --- | --- |
| FEATURE | Location/Qualifiers |
| source | 1..588 |
| | mol_type = genomic DNA |
| | organism = Glycine max |

SEQUENCE: 5

| | |
|---|---|
| ttgcatttgg gcaattttgc tagcacatgt gatcatcatc gtggttactc ctttatagta | 60 |
| gttttatcct tgcagagtct taggtgtttt gtttaagtta tattttttaag tttctgccga | 120 |
| tttcatgtag ccgtaacttt caaaactagg ttcttgatcg gcgtggtca attttcattg | 180 |
| ctgtttgttt ttgatgagta ctgttttttg ttttgatggt aagaagagtc tgagatattt | 240 |
| cgaatttcac aagcagctat agggttttag tccatttcct ttgctgctga gggatgtttt | 300 |
| aagttgcatt taatttataa cgaagtttta taaactgttt atggtttaaa ggctattatt | 360 |
| ctttaatttt gttgttgaag taatgtgagt gggaggtgcg cttgagctgt gtggacgtag | 420 |
| ttagctctta attatgcgat cgtagattcg tagttgcact aatgaacaat tgttgccatg | 480 |
| tttatctttt caagagtacc tgtcaccaat tacgcaatcc attcttatgc aatattattg | 540 |
| attgataaat aaaaaggaat acgcaggcca atatattgtt gtataaca | 588 |

| SEQ ID NO: 6 | moltype = DNA   length = 1416 |
| --- | --- |
| FEATURE | Location/Qualifiers |
| misc_feature | 1..1416 |
| | note = Synthetic GmAct7-2 promoter and 5'UTR from |
| | Glyma06g15520 |
| source | 1..1416 |
| | mol_type = other DNA |
| | organism = synthetic construct |

```
SEQUENCE: 6
aaagggtaga aaggtgtgaa atgaaaaaga aaaggctgtc atccagtcac cctatccctc    60
ttttctcgtg gtcgaaatga ttccctctct ctccagtcct tcaatttcaa tttttggtcc   120
caacctcaat tccaatttca aatacattac attacactct cactctcaca ccaacgacac   180
actctctctt tccgcatata tatacccctt ctccttctcc cctctctct tctcattcct   240
ctttcctctt tctgtagccc tcaagcaccg gagagagaga gagtgtgtgt gtgtgtgagt   300
gagtgctaag ccatcttctt cttctcacac aaggtattca tcttaatctc tcacatcata   360
actttgatgc aaagtacgtt tccttttgct ctttgattca gcgcttttg caatctcgaa    420
tgtttattct tagattttgt tccatagtagt actctttttt atgtttttct ttttaaatct   480
gtgtgagata agattgttac ctacctcatc aaaatcatat ctggatgttt tgtatctgat   540
tatttatatt cgtactacct gatctatact gaatgaaatg tagtagattg tggcgatctg   600
tagttttagt ggtggaaatg acatatcaca gttccgatct tctatagcag agatcttcga   660
acttttttgaa ctgtaccttt acttattctg aaatgtggat agccatcgat tacataatct   720
ggtgttggat ggatttatgg tctgatctgt tttttttatc actttttgg cttttatttt    780
ttcctcattg atctttctta gtagaagatc atttggtttg ggaacttaag atatgctgtg   840
tcagaggact tctgagattt tagctggtgt cctaatggac gttttctatt catctattaa   900
ttttggcagt ttcatttaaa aaatgcacag gatcggctcc tttatctgtt tatgtacatt   960
tgttactgtt ttatttctaa gtagattgta taatactgaa ttatttttt tccttgtttt    1020
ctttcctatt gattttgtgt gttatatata ctatgatgct gtcttgtgta gaaaaagaga   1080
gtttgaagta aaccctcaaa gtctgtaaat ggctgggttc tgtagattgt ctattcaaac   1140
ttggtggtac tgacaattta ttgtatgcgt actgtagttt ggtaaaaaat ggctgatgct   1200
gaggatattc aaccccttgt ttgtgacaat ggaactgtaa tgtttgaaggt tagtacttg   1260
cagtttcttg ttagtgtaat tgcatctatt tagtcttggt ttcattattg ctcaatttat   1320
ttaaatgatc atctgtgtac aggcaggatt tgctgtgacg atgttcctag gctgtgtttt   1380
cccagtattg ttggtcgacc tcgtcatact ggtgtt                             1416

SEQ ID NO: 7              moltype = DNA   length = 1170
FEATURE                   Location/Qualifiers
misc_feature              1..1170
                          note = Synthetic GmGAPC2 promoter and 5' UTR from
                          Glyma0618110
source                    1..1170
                          mol_type = other DNA
                          organism = synthetic construct
SEQUENCE: 7
cccaaataac tgctaattag tatgaatagg ataggattag tacaatctat tgcaggaaag    60
tatgtgttca tgtttatta gacaaaaatt aaacaaaatt ttaaaataaa aaacagagga   120
aatcatgcct tggcttggta acttactatc ttctggtcct tcatatgata aacaaacagt   180
gttttttcc cctaatcata agaatcatat aattattttt aaatgtatta ataactattt   240
ttttatatct ttaatttgtt gtgaagtctt ttaatgatca ctcattattc atgaaagtat   300
atacagttaa tgaactatta ataatataac ttattctcat cggttaacaa gtattttca   360
tgtattatga gtagtgatat tatatgtaac cacttcttat atccattgat tttatggata   420
tttttaaaat aaaaatttgaa tttatattag tattaattaa aagtaactac tttaatcatt   480
tttatttgtc ttgattatt aatcttatgg tttcatttg tgatgatgat caaagatagt    540
atgatagtat gattttgtta tatttgtgca cacttagtt atgttaata attttttta   600
aaaaaatata aatatattga aaaggtcata tgcaagcggt agcctcaccc aagaataatt   660
aaaatagacc caaattctct gaataaatag acctaaatac tccatgaatg tgtttcattg   720
tttgttattt gatgttcatc aaatatcaaa tataattaaa gctcatcata ttctcgtaca   780
gtatagtatt agtattatat cctgctcact aaaccaaaca tctaagaata accttatttc   840
atttagaaaa aaacccaag taaaattgaa aaagaatca aaacaataaa aagagagaaa    900
agcgaatgga atattcgcat atctgtttggc gtgaaacaga aaccacaaaa aaaacggtac   960
agcgtagtag tccttggcaa agcatcacga gtcacaaggc ggtcccgtag gagtcacgca  1020
cttcacttgg cccattacc tgtcattgcg gtctttact cttctcaata ccttattaaa   1080
accctatctc actcactcac tcacaccgtt ccatttctca caacttctg ctacttccta   1140
ctccaaccgc acttctgctc cgcaattatc                                   1170

SEQ ID NO: 8              moltype = DNA   length = 632
FEATURE                   Location/Qualifiers
source                    1..632
                          mol_type = genomic DNA
                          organism = Glycine max
SEQUENCE: 8
aggtgggata ggattggagg gtatattcgg agctgtgatg tatcatatat tgtgtggcat    60
ccctctggat gtggcgggca cagaattgat gagaagcatt tttcaccttg gaattcatca   120
atgtcttcga aagtaggttg tctgtagcaa aggagtgatt gtgaatgctt atttttatttt  180
ctatgtatcc ttttttcagag ttcacatttt ttttggcctt cggaacatta atgtgaatgt   240
ctatagctac atgtatcgag aatttatat aagattgtca gttcgcactc aaattatcaa   300
atttttagttt attcatgaat cacttgcccg atatttgagt gtgctatagg catgaagaca   360
cacttaaaag ttgtaatggt gaggatacct gcacgatccc tggtttacca ggagtccaag   420
ggaagggaaa atatctaaat actctaattt tgctatcggt taaatttaat tttaatattt   480
tttagtattg agtttattaa tgtgtatgat tatgctctgt tacgtgttat gttttttagtt   540
gagtaaaataa tttcacaaga atttcagata acaagaataa ttttacattc aaacctagtg   600
gatacacgat atatgaatga aaagaatatt gt                                 632

SEQ ID NO: 9              moltype = DNA   length = 525
FEATURE                   Location/Qualifiers
source                    1..525
                          mol_type = genomic DNA
                          organism = Glycine max
```

```
SEQUENCE: 9
cgtttatcta gaacttcacg gaataatcag tttccaaaaa gtactttcac actattacag    60
tataacttat ccaaccaatt aagttttgaa tatcaggtac gccaatcaaa ccaatatgaa   120
ctaaaagcca aaaatgttaa tttaaatacg gactaaaata agcacagaaa atgtttaaa    180
ccacgaatcc aagattcaaa gcaaacagga tcaaatatac gagaaccaca aatgaaaaaa   240
aggacggaca aatatctact ataacaatca ataacaagta cattagcaag tattcaagcc   300
aagtacatca gcgagtatat aaaaatccaa aaactcgatc ccctccaca  agagaaaaca   360
tcaaaagtcc aaaaaagagc taatgctcct ccaacaagta acaccactgg tttcagaaac   420
cgatttattc agacctctca ttttttgctc gagcaagaca ctaaatcgca gctaaacata   480
aacatacggt aataatgtga agacaagcta ctttgaagta acacc                   525

SEQ ID NO: 10              moltype = DNA   length = 1686
FEATURE                    Location/Qualifiers
misc_feature               1..1686
                           note = The coding sequence of the chimeric RFP/AAD12
                             reporter gene
source                     1..1686
                           mol_type = other DNA
                           organism = synthetic construct
SEQUENCE: 10
atggtgagca aaggcgagga acttatcaaa gagaacatgc acatgaagct ctacatggag    60
ggcactgtca acaatcatca cttcaaatgc acatccgagg agaaggcaa  gccttatgag   120
ggaacccaga ccatgaggat caaagtggtt gagggtggac cactcccatt tgccttcgac   180
atacttgcca ctagcttcat gtatggctcc agaactttca tcaatcacac acaagggatt   240
cccgacttct taagcagtc  ttttcctgag ggtttcacat gggagcgtgt tacaacttac   300
gaagatgg tg gcgtgttgac cgctactcaa gacacttctt tgcaagatgg tgtgtctcatc  360
tacaatgtca agattagagg tgtgaacttt ccatcaaatg gaccagttat gcagaagaaa   420
acccttggat gggaagcaaa caccgagatg ctttacccag ccgatggtgg gcttgagggg   480
aggtctgata tggcactcaa gttggttgga ggtggccatt tgatttgcaa cttcaagacc   540
acataccgct caaagaaacc tgctaagaat ctcaagatgc ctggcgtcta ctatgtggat   600
catcgcttgg aaaggatcaa ggaggcagac aaggaaacct atgtcgaaca gcatgaggtg   660
gctgttgctc gttactgtga ccttcccagc aagctcggac acaagttgaa tctcgccgag   720
gaagcagccg ctaagagagc tgcagccaag gaagccgctg caaggaggc  tgccgcaaaa   780
gaagccgcag ctaaggcagc tgccatggct cagaccactc tccaaatcac acccactggt   840
gccaccttgg gtgccacagt cactggtgtt caccttgcca cacttgacga tgctggtttc   900
gctgccctcc atgcagcctg gcttcaacat gcactcttga tcttccctgg caacacctc    960
agcaatgacc aacagattac ctttgctaaa cgctttggag caattgagag gattggcgga  1020
ggtgacattg ttgccatatc caatgtcaag gcagatggca cagtgcgcca gcactctcct  1080
gctgagtggg atgacatgat gaaggtcatt gtgggcaaca tggcctggca cgccgactca  1140
acctacatgc cagtcatggc tcaaggagct gtgttcagcg cagaagttgt cccagcagtt  1200
gggggcagaa cctgctttgc tgacatgagg gcagcctacg atgcccttga tgaggcaacc  1260
cgtgctcttg ttcaccaaag gtctgctcgt cactcccttg tgtattctca gagcaagttg  1320
ggacatgtcc aacaggccgg gtcagcctac ataggttatg gcatggacac cactgcaact  1380
cctctcagac cattggtcaa ggtgcatcct gagactggaa ggcccagcct cttgatcggc  1440
cgccatgccc atgccatccc tggcatggat gcagctgaat cagagcgctt ccttgaagga  1500
cttgttgact gggcctgcca ggctcccaga gtccatgctc accaatgggc tgctggagat  1560
gtggttgtgt gggacaaccg ctgtttgctc caccgtgctg agcctgggga tttcaagttg  1620
ccacgtgtga tgtggcactc cagactcgct ggacgcccag aaactgaggg tgctgccttg  1680
gtttga                                                             1686

SEQ ID NO: 11              moltype = DNA   length = 3686
FEATURE                    Location/Qualifiers
misc_feature               1..3686
                           note = Gene expression casette containing the GmTEFs1
                             promoter - GmTEFs1 5' UTR - RFP/AAD12 coding sequence -
                             GmTEFs1 terminator
source                     1..3686
                           mol_type = other DNA
                           organism = synthetic construct
SEQUENCE: 11
cccagcattt gccacgttcg aacgtgagcc aaaacgatgt cgttacaata tcttaaccta    60
gccgaaacga tgtcgtggta actcataata tcgcagcctt ctgtttcgtc cttgcccaat   120
gccaactgga ctacgccgaa cccacaaaac ccgacatccg cgcgaaccaa agcgcgtgac   180
gccaaattgc tcaaaccaca aaggaaacaa aggcgcgtta ataacacgcg ctatcccacg   240
cgtgttaagc acagtaacgt tcaacaaaga gaagcagggt ataatgggaa accaaagaga   300
aacctaaggc cattatggga aacaaaagt  agctcactca ttataaaatt caagtaaccc   360
tagttttcat catcactctg ctgcctcgct ctgtttctgt ctctgtgttt gcggctgagg   420
attccgaacg agcgaccttc ttcgtttctc gcaaaggtaa cagctctgc  tcttgtctct   480
tccattcgat ccatgcctgt ctcttcttta cgatgattgt tcttcggtgt atgtttattt   540
atttatttat ttatgcttta tgttgtgaat gttcggttgt tttgtttcgc tttgcttttg   600
tggattctat tggttttttga atcagttaat cggaagagat tttcgagttg ttttgtgttt   660
tggaggtgaa tctttttgtt gaggtcgcag atctgttgat tttgtgtcat aaacgtgcga   720
ctctgtttga ttttttacga ggttatgacg ttttggttgt tttattatgg atctgttaag   780
gcagaaccat gatttatgtt tatgttcgtt tacacgatta aattttcttg taacacgatg   840
aagtttttt  aaacacgttg aaggagtctt gttgatatga atttgtcgat gtttttttg    900
tggttttgtt ctcacgttat caagcgtaat cttttactat gtacgcgaac atatctagat   960
ctagcagagc ttttttttt  tttaattctt tgtgaagctt ttgaaatatg aaatttgttt  1020
ttcaaatttt tttttaattt attgaaaaca ctgtggatac tgaataaggt tctatgtatg  1080
atgcgaacca tgtttgatat gtttgttttt gttgttccat atggattttt ctgttagatt  1140
```

```
tccatatgct ttttgagtttg tttttgctgt tacagattga tttactttt  agaatatttc   1200
tcttggcttt cactgtttta gaaatttttt gttattggta actataaatg tgtgaatttg   1260
gattataacct ttaccttgtt atttagttgt gtgataattt ggtttatagt tatttgagt   1320
tctgactcgt gtttctttga attgattcca gtttaagtca tcggatccaa acaatggtga   1380
gcaaaggcga ggaacttatc aaagagaaca tgcacatgaa gctctacatg gagggcactg   1440
tcaacaatca tcacttcaaa tgcacatccg agggagaagg caagccttat gagggaaccc   1500
agaccatgag gatcaaagtg gttgagggtg gaccactccc atttgccttc gacatacttg   1560
ccactagctt catgtatggc tccagaactt tcatcaatca cacacaaggg attcccgact   1620
tctttaagca gtcttttcct gagggtttca catgggagcg tgttacaact tacgaagatg   1680
gtggcgtgtt gaccgctact caagacactt ctttgcaaga tgggtgtctc atctacaatg   1740
tcaagattag aggtgtgaac tttccatcaa atggaccagt tatgcagaag aaaacccttg   1800
gatgggaagc aaacaccgag atgctttacc cagccgatgg tgggcttgag gggaggtctg   1860
atatggcact caagttggtt ggaggtgcc  atttgatttg caacttcaag accacatacc   1920
gctcaaagaa acctgctaag aatctcaaga tgcctggcgt ctactatgtg gatcatcgct   1980
tggaaaggat caaggaggca gacaaggaaa cctatgtcga acagcatgag gtggctgttg   2040
ctcgttactg tgaccttccc agcaagctcg gacacaagtt gaatctcgcc gaggaagcag   2100
ccgctaaaga ggctgcagcc aaggaagccg ctgcaaagga ggctgccgca aaagaagccg   2160
cagctaaggc agctgccatg gctcagacca ctctccaaat cacacccact ggtgccacct   2220
tgggtgccac agtcactggt gttcaccttg ccacacttga cgatgctggt ttcgctgccc   2280
tccatgcagc ctggcttcaa catgcactct tgatcttccc tggcaacac  ctcagcaatg   2340
accaacagat taccttgct  aaacgctttg gagcaattga gaggattggc ggaggtgaca   2400
ttgttgccat atccaatgtc aaggcagatg gcacagtgcg cacactct   cctgctgagt   2460
gggatgacat gatgaaggtc attgtgggca acatggcctg gcacgccgac tcaacctaca   2520
tgccagtcat ggctcaagga gctgtgttca gcgcagaagt tgtcccagca gttggggca    2580
gaacctgctt tgctgacatg agggcagcct acgatgccct tgatgaggca acccgtgctc   2640
ttgttcacca aagtctgct  cgtcactccc ttgtgtattc tcagagcagg ttgggacatg   2700
tccaacaggc cgggtcagcc tacataggtt atggcatgaa caccactgca actcctctca   2760
gaccattggt caaggtgcat cctgagactg gaaggcccag cctcttgatc ggccgccatg   2820
cccatgccat ccctggcatg gatgcagctg aatcagagcg cttccttgaa ggacttgttg   2880
actgggcctg ccaggctccc agagtccatg ctcaccaatg ggctgctgga gatgtggttg   2940
tgtgggacaa ccgctgtttg ctccaccgtg ctgagccctg ggatttcaag ttgccacgtg   3000
tgatgtggca ctcagactc  gctggacgcc cagaaactga gggtgctgcc ttggtttgag   3060
tagttagctt aatcacctag agctcggtca ccgagctctt gcatttgggc aattttgcta   3120
gcacatgta  tcatcatcgt ggttactcct ttatagtagt tttatccttg cagagtctta   3180
ggtgtttgt  ttaagttata tttttaagtt tctgccgatt tcatgtagcc gtaacttca   3240
aaactaggtt cttgatcggc ggtggtcaat tttcattgct gtttgttttt gatgagtact   3300
gttttttgtt ttgatggtaa gaagagtctg agatatttcg aatttcacaa gcagctatag   3360
ggttttagtc cattttcttt gctgctgagg gatgttttaa gttgcattta atttataacg   3420
aagttttata aactgtttat ggtttaaagg ctattattct ttaattttgt tgttgaagta   3480
atgtgagtgg gaggtgcgct tgagctgtgt ggacgtagtt agctcttaat tatgcgatcg   3540
tagattcgta gttgcactaa tgaacaattg ttgccatgtt ttatcttca  agagtacctg   3600
tcaccaatta cgcaatccat tcttatgcaa tattattgat tgataaataa aaagaatac   3660
gcaggccaat atattgttgt ataaca                                        3686

SEQ ID NO: 12            moltype = DNA   length = 5287
FEATURE                  Location/Qualifiers
misc_feature             1..5287
                         note = Gene expression cassette containing the GFP and PAT
                         reporter/selectable marker genes
source                   1..5287
                         mol_type = other DNA
                         organism = synthetic construct
SEQUENCE: 12
aagcttcgga tttggagcca agtctcataa acgccattgt ggaagaaagt cttgagttgg   60
tggtaatgta acagagtagt aagaacagag aagagagaga gtgtgagata catgaattgt   120
cgggcaacaa aaatcctgaa catcttattt tagcaaagag aaagagttcc gagtctgtag   180
cagaagagtg aggagaaatt taagctcttg gacttgtgaa ttgttccgcc tcttgaatac   240
ttcttcaatc ctcatatatt cttcttctat gttaccctgaa aaccggcatt taatctcgcg   300
ggtttattcc ggttcaacat ttttttttgtt ttgagttatt atctgggctt aataacgcag   360
gcctgaaata aattcaaggc ccaactgttt tttttttaa gaagttgctg ttaaaaaaaa   420
aaaagggaat taacaacaac aacaaaaaaa gataaagaaa ataataacaa ttactttaat   480
tgtagactaa aaaaacatag attttatcat gaaaaaaaga gaaagaaat aaaaacttgg   540
atcaaaaaaa aaaacataca gatcttctaa ttattaactt tcttaaaaa  ttaggtcctt   600
tttcccaaca attaggttta gagttttgga attaaaccaa aaagattgtt ctaaaaaata   660
ctcaaatttg gtagataagt ttccttattt taattagtca atggtagata cttttttttc   720
ttttctttat tagagtagat tagaatcttt tatgccaagt attgataaat taaatcaaga   780
agataaaacta tcataatcaa catgaaatta aagaaaaat  ctcatatata gtattagtat   840
tctctatata tattatgatt gcttattctt aatgggttgg gttaaccaag acatagtcta   900
aatggaaaga atctttttg  aactttttcc ttattgatta aattcttcta tagaaaagaa   960
agaaattatt tgaggaaaag tatatacaaa aagaaaaata gaaaatgtc  agtgaagcag   1020
atgtaatgga tgacctaatc caaccaccac cataggatgt ttctacttga gtcggtcttt   1080
taaaacgca  cggtggaaaa tatgcacacgt atcatatgat tccttccttt agtttcgtga   1140
taatatcct  caactgatat cttccttttt ttgtttggc taaagatatt ttattctcat   1200
taatagaaaa gacggttttg ggcttttggt ttgcgatata aagaagacct tcgtgtgaa   1260
gataataatt catcccttcg tcttttttctg actcttcaat ctctcccaaa gcctaaagcg   1320
atctctgcaa atctctcgcg actctctctt tcaaggtata ttttctgatt cttttttgttt   1380
ttgattcgta tctgatctcc aatttttgtt atgtggatta ttgaatcttt tgtataaatt   1440
gcttttgaca atattgttcg tttcgtcaat ccagcttcta aattttgtcc tgattactaa   1500
gatatcgatt cgtagtgttt acatctgtgt aatttcttgc ttgattgtga aattaggatt   1560
```

```
ttcaaggacg atctattcaa tttttgtgtt ttctttgttc gattctctct gttttaggtt    1620
tcttatgttt agatccgttt ctctttggtg ttgttttgat ttctcttacg gcttttgatt    1680
tggtatatgt tcgctgattg gtttctactt gttctattgt tttatttcag ggatctccat    1740
ggagtccgat gaatccggtc tcccagctat ggagattgaa tgcagaatca ctggcacttt    1800
gaacggtgtt gagtttgaac tggtgggagg tggcgaaggg acgcctgaac aagggaggat    1860
gacaaacaag atgaagtcca ccaaggtgca attgaccttc tctccgtacc ttctcagcca    1920
tgtcatgggc tacggtttct atcactttgg cacctatccg tctggctatg agaacccctt    1980
tcttcatgcc atcaacaatg gaggttacac caacacacgc attgagaagt atgaagatgg    2040
tggagtgctc cacgtctcct tcagctaccg ctacgaggct gggagggtca taggagattt    2100
caaagtgatg ggaactggct ttccagagga ctcagtcatc ttcacagaca agatcattag    2160
atccaatgca acggttgagc atcttcaccc aatgggagac aatgacctgg atgggtcatt    2220
cacaagaacg ttctctctgc gtgatggagg ctactatagc tctgttgtgg actcacacat    2280
gcacttcaaa tctgccattc atcctagcat cttgcagaat ggtggaccca tgtttgcttt    2340
tcgtagggtg gaagaggatc actcaaacac cgagcttgac atagttgagt accagcatgc    2400
cttcaagact cctgatgcag atgctgggga agagtgagta gttagcttaa tcacttaggt    2460
caccgagctc cttttttgtga tctgatgata agtggttggt tcgtgtctca tgcacttggg    2520
aggtgatcta tttcacctgg tgtagttttgt gtttccgtca gttggaaaaa cttatcccta    2580
tcgatttcgt tttcattttc tgcttttctt ttatgtacct tcgtttgggc ttgtaacggg    2640
cctttgtatt tcaactctca ataataatcc aagtgcatgt taaacaattt gtcatctgtt    2700
tcggctttga tatactactg gtgaagatgg gccgtactac tgcatcacaa cgaaaaataa    2760
taataagatg aaaaacttga agtggaaaaa aaaaaaaact tgaatgttca ctactactca    2820
ttgaccataa tgtttaacat acatagcctca atagtatttt tgtgaatatg gcaacacaaa    2880
cagtccaaaa caattgtctc ttactatacc aaaccaaggg cgccgcttgt ttgccactct    2940
ttgtgtgcaa tagtgtgatt accacatctc cacattcaat atattccctg aattatctga    3000
cgattttgat ggctcactgt tttcccaagt cttgaattgt cttctgtgcg ccagtcaaat    3060
gcatatgtgt tgagtttatc ttttaaatat caagcttttt ttttaacttt ttgtttgtaa    3120
ccaaaaactc acagtaggag tttgatcaca taatttatg tttgcctttg caatttctag     3180
tgagtctttg attaagcggc cgcttaatta aactagtgct agcctcgagg tcgactctga    3240
tcatggatgc tacgtcacgg cagtacagga ctatcatctt gaaagtcgat tgagcatcga    3300
aacccagctt tcttgtacaa agtggttgcg gccgcttaag taaggcgccc ggtatttgtt    3360
aaaagcggcg atagctttcg aagtacttag tcaagacgag cagtccgaag cgatcgcgtt    3420
tgggaagcta ggccaccgtg gcccgcctgc aggggaagct tgtttaaacc cagaaggtaa    3480
ttatccaaga tgtagcatca agaatccaat gtttacggga aaaactatgg aagtattatg    3540
taagctcagc aagaagcaga tcaatatgcg gcacatatgc aacctatgtt caaaaatgaa    3600
gaatgtacag atacaagatc ctatactgcc agaatacgaa gaagaatacg tagaaattga    3660
aaagaagaa ccaggcgaag aaaagaatct tgaagacgta agcactgacg acaacaatga     3720
aaagaagaag ataaggtcgg tgattgtgaa agagacatag aggacacatg taaggtggaa    3780
aatgtaaggg cggaaagtaa ccttatcaca aaggaatctt atcccccact acttatcctt    3840
ttatattttt ccgtgtcatt tttgcccttg agttttccta tataaggaac caagttcggc    3900
atttgtgaaa acaagaaaaa atttggtgta agctattttc tttgaagtac tgaggataca    3960
acttcagaga aatttgtaag tttgtagatc tccatgtctc cggagaggag accagttgag    4020
attaggccag ctacagcagc tgatatggcc gcggtttgtg atatcgttaa ccattacatt    4080
gagacgtcta cagtgaactt taggacagag ccacaaacac cacaagagtg gattgatgat    4140
ctagagaggt tgcaagatag ataccccttg ttggttgctg aggttgaggg tgttgtggct    4200
ggtattgctt acgctgggcc ctggaaggct aggaacgctt acgattggac agttgagagt    4260
actgtttacg tgtcacatag gcatcaaagg ttgggcctag gatccacatt gtacacacat    4320
ttgcttaagt ctatggaggc gcaaggtttt aagtctgtgg ttgctgttat aggccttcca    4380
aacgatccat ctgttaggtt gcatgaggct ttgggataca cagcccgtgg tacattgcgc    4440
gcagctggat acaagcatgg tggatggcat gatgttggtt tttggcaaag ggattttgag    4500
ttgccagctc ctcaaggcc agttaggcca gttaccagaa tctgactgag cttgagctta    4560
tgagcttaga agcttagagc tcagatcggc ggcaatagct tcttagcgcc atcccgagtt    4620
gatcctatct gtgttgaaat agttgcggtg ggcaaggctc tctttcagaa agacaggcgg    4680
ccaaaggaac ccaaggtgag gtgggctatg gctctcagtt ccttgtggaa gcgcttggtc    4740
taaggtgcag aggtgttagc ggggatgaag caaaagtgtc cgattgtaac aagatatgtt    4800
gatcctacgt aaggatatta aagtatgtat tcatcactaa tataatcagt gtattccaat    4860
atgtactacg atttccaatg tctttattgt cgccgtatgc aatcggcgtc acaaaataat    4920
ccccggtgac tttcttttaa tccaggatga aataatatgt tattataatt tttgcgattt    4980
ggtccgttat aggaattgaa gtgtgcttgc ggtcgccacc actcccattt cataattta     5040
catgtatttg aaaaataaaa atttatggta ttcaatttaa acacgtatc ttgtaaagaa     5100
tgatatcttg aaagaaatat agtttaaata tttattgata aaataacaag tcaggtatta    5160
tagtccaagc aaaaacataa atttattgat gcaagtttaa attcagaaat atttcaataa    5220
ctgattatat cagctggtac attgccgtag atgaaagact gagtgcgata ttatggtgta    5280
atacata                                                              5287
```

| | | |
|---|---|---|
| SEQ ID NO: 13 | moltype = DNA length = 22 | |
| FEATURE | Location/Qualifiers | |
| misc_feature | 1..22 | |
| | note = Primer sequence | |
| source | 1..22 | |
| | mol_type = other DNA | |
| | organism = synthetic construct | |

SEQUENCE: 13
gaggattagg gtttcaacgg ag                                        22

| | | |
|---|---|---|
| SEQ ID NO: 14 | moltype = DNA length = 21 | |
| FEATURE | Location/Qualifiers | |
| misc_feature | 1..21 | |
| | note = Primer Sequence | |
| source | 1..21 | |

```
                              mol_type = other DNA
                              organism = synthetic construct
SEQUENCE: 14
gagaattgag ctgagacgag g                                                   21

SEQ ID NO: 15             moltype = DNA   length = 25
FEATURE                   Location/Qualifiers
misc_feature              1..25
                          note = Probe Sequence
source                    1..25
                          mol_type = other DNA
                          organism = synthetic construct
SEQUENCE: 15
agagaagttt cgacggattt cgggc                                               25

SEQ ID NO: 16             moltype = DNA   length = 29
FEATURE                   Location/Qualifiers
misc_feature              1..29
                          note = Primer Sequence
source                    1..29
                          mol_type = other DNA
                          organism = synthetic construct
SEQUENCE: 16
acaagagtgg attgatgatc tagagaggt                                           29

SEQ ID NO: 17             moltype = DNA   length = 29
FEATURE                   Location/Qualifiers
misc_feature              1..29
                          note = Primer Sequence
source                    1..29
                          mol_type = other DNA
                          organism = synthetic construct
SEQUENCE: 17
ctttgatgcc tatgtgacac gtaaacagt                                           29

SEQ ID NO: 18             moltype = DNA   length = 29
FEATURE                   Location/Qualifiers
misc_feature              1..29
                          note = Probe Sequence
source                    1..29
                          mol_type = other DNA
                          organism = synthetic construct
SEQUENCE: 18
agggtgttgt ggctggtatt gcttacgct                                           29

SEQ ID NO: 19             moltype = DNA   length = 20
FEATURE                   Location/Qualifiers
misc_feature              1..20
                          note = Primer Sequence
source                    1..20
                          mol_type = other DNA
                          organism = synthetic construct
SEQUENCE: 19
cagagtccat gctcaccaat                                                     20

SEQ ID NO: 20             moltype = DNA   length = 19
FEATURE                   Location/Qualifiers
misc_feature              1..19
                          note = Primer Sequence
source                    1..19
                          mol_type = other DNA
                          organism = synthetic construct
SEQUENCE: 20
acgtggcaac ttgaaatcc                                                      19

SEQ ID NO: 21             moltype = DNA   length = 24
FEATURE                   Location/Qualifiers
misc_feature              1..24
                          note = Probe Sequence
source                    1..24
                          mol_type = other DNA
                          organism = synthetic construct
SEQUENCE: 21
tggagatgtg gttgtgtggg acaa                                                24

SEQ ID NO: 22             moltype = DNA   length = 26
FEATURE                   Location/Qualifiers
misc_feature              1..26
                          note = Primer Sequence
```

```
source                         1..26
                               mol_type = other DNA
                               organism = synthetic construct
SEQUENCE: 22
acaagagtgg attgatgatc tagaga                                          26

SEQ ID NO: 23                  moltype = DNA   length = 26
FEATURE                        Location/Qualifiers
misc_feature                   1..26
                               note = Primer Sequence
source                         1..26
                               mol_type = other DNA
                               organism = synthetic construct
SEQUENCE: 23
ctttgatgcc tatgtgacac gtaaac                                          26

SEQ ID NO: 24                  moltype = DNA   length = 29
FEATURE                        Location/Qualifiers
misc_feature                   1..29
                               note = Probe Sequence
source                         1..29
                               mol_type = other DNA
                               organism = synthetic construct
SEQUENCE: 24
ccagcgtaag caataccagc cacaacacc                                       29

SEQ ID NO: 25                  moltype = DNA   length = 21
FEATURE                        Location/Qualifiers
misc_feature                   1..21
                               note = Primer Sequence
source                         1..21
                               mol_type = other DNA
                               organism = synthetic construct
SEQUENCE: 25
cgccgaagta tcgactcaac t                                               21

SEQ ID NO: 26                  moltype = DNA   length = 19
FEATURE                        Location/Qualifiers
misc_feature                   1..19
                               note = Primer Sequence
source                         1..19
                               mol_type = other DNA
                               organism = synthetic construct
SEQUENCE: 26
gcaacgtcgg ttcgagatg                                                  19

SEQ ID NO: 27                  moltype = DNA   length = 24
FEATURE                        Location/Qualifiers
misc_feature                   1..24
                               note = Probe Sequence
source                         1..24
                               mol_type = other DNA
                               organism = synthetic construct
SEQUENCE: 27
tcagaggtag ttggcgtcat cgag                                            24

SEQ ID NO: 28                  moltype = DNA   length = 895
FEATURE                        Location/Qualifiers
source                         1..895
                               mol_type = genomic DNA
                               organism = Glycine max
SEQUENCE: 28
gtaacagcct ctgctcttgt ctcttccatt cgatccatgc ctgtctcttc tttacgatga     60
tgtttcttcg gtgtatgttt atttatttat ttatttatgc tttatgttgt gaatgttcgg    120
ttgttttgtt tcgctttgct tttgtggatt ctattggttt ttgaatcagt taatcggaag    180
agatttcga gttgttttgt gttttggagg tgaatctttt tgttgaggtc gcagatctgt    240
tgattttgtg tcataaacgt gcgactctgt ttgatttttt acgaggttat gacgttttgg    300
ttgttttatt atggatctgt taaggcagaa ccatgattta tgtttatgtt cgtttacacg    360
attaaatttt cttgtaacac gatgaagttt ttttaaacac gttgaaggag tcttgttgat    420
atgaatttgt cgattgtttt tttgtggttt tgttctcacg ttatcaagcg taatcttta    480
ctatgtacgc gaacatatct agatctagca gagctttttt tttttttaat tcttttgtgaa    540
gcttttgaaa tatgaaattt gtttttcaaa tttttttta atttattgaa aacactgtgg    600
atactgaata aggttctatg tatgatgcga accatgtttg atatgtttgt ttttgttgtt    660
ccatatggat ttttctgtta gatttccata tgcttttgag tttgttttg ctgttacaga    720
ttgatttact ttttagaata tttctcttgg ctttcactgt tttagaaatt ttttgttatt    780
ggtaactata aatgtgtgaa tttggattat acctttacct tgttatttag ttgtgtgata    840
atttggttta tagttatttt gagttctgac tcgtgttttct ttgaattgat tccag        895
```

PLANT PROMOTER FOR TRANSGENE EXPRESSION

INCORPORATION BY REFERENCE

This application claims the benefit of application Ser. No. 17/538,437 filed on Nov. 30, 2021, now issued, which claims the benefit of application Ser. No. 16/763,406 filed on May 12, 2020, now issued as U.S. Pat. No. 11,274,311, which claims the benefit of PCT/US18/58337 filed on Oct. 31, 2018 which claims the benefit of U.S. Provisional Patent Application Ser. No. 62/587,034 filed Nov. 16, 2017 which is expressly incorporated by reference in its entirety herein.

Incorporated by reference in its entirety is a computer-readable nucleotide/amino acid sequence listing submitted concurrently herewith and identified as follows: one 52.5 KB .XML file named "80596-US-PCN2" created on Dec. 6, 2022.

BACKGROUND

Many plant species are capable of being transformed with transgenes to introduce agronomically desirable traits or characteristics. The resulting plant species are developed and/or modified to have particular desirable traits. Generally, desirable traits include, for example, improving nutritional value quality, increasing yield, conferring pest or disease resistance, increasing drought and stress tolerance, improving horticultural qualities (e.g., pigmentation and growth), imparting herbicide tolerance, enabling the production of industrially useful compounds and/or materials from the plant, and/or enabling the production of pharmaceuticals.

Transgenic plant species comprising multiple transgenes stacked at a single genomic locus are produced via plant transformation technologies. Plant transformation technologies result in the introduction of a transgene into a plant cell, recovery of a fertile transgenic plant that contains the stably integrated copy of the transgene in the plant genome, and subsequent transgene expression via transcription and translation results in transgenic plants that possess desirable traits and phenotypes. However, novel gene regulatory elements that allow the production of transgenic plant species to highly express multiple transgenes engineered as a trait stack are desirable.

Likewise, novel gene regulatory elements that allow the expression of a transgene within particular tissues or organs of a plant are desirable. For example, increased resistance of a plant to infection by soil-borne pathogens might be accomplished by transforming the plant genome with a pathogen-resistance gene such that pathogen-resistance protein is robustly expressed within the roots of the plant. Alternatively, it may be desirable to express a transgene in plant tissues that are in a particular growth or developmental phase such as, for example, cell division or elongation. Furthermore, it may be desirable to express a transgene in leaf and stem tissues of a plant to provide tolerance against herbicides, or resistance against above ground insects and pests.

Therefore, a need exists for new gene regulatory elements that can drive the desired levels of expression of transgenes in specific plant tissues.

BRIEF SUMMARY

In embodiments of the subject disclosure, the disclosure relates to a nucleic acid vector comprising a promoter operably linked to: a polylinker sequence; a non-GmTEFs1 heterologous coding sequence; wherein said promoter comprises a polynucleotide sequence that has at least 95% sequence identity with SEQ ID NO:2. In further embodiments, said promoter is 371 bp in length. In other embodiments, said promoter consists of a polynucleotide sequence that has at least 95% sequence identity with SEQ ID NO:2. In additional embodiments, said promoter is operably linked to a heterologous coding sequence. Accordingly, the heterologous coding sequence encodes a selectable marker protein, an insecticidal resistance protein, a herbicide tolerance protein, a nitrogen use efficiency protein, a water use efficiency protein, a small RNA molecule, a nutritional quality protein, or a DNA binding protein. In other embodiments, the nucleic acid vector comprises a terminator polynucleotide sequence. In additional embodiments, the nucleic acid vector comprises a 3' untranslated polynucleotide sequence. In additional embodiments, the nucleic acid vector comprises a 5' untranslated polynucleotide sequence. In additional embodiments, the nucleic acid vector comprises an intron sequence. In additional embodiments, said promoter has tissue constitutive expression. In further embodiments, the nucleic acid vector comprises a polynucleotide sequence that has at least 95% sequence identity with SEQ ID NO:2 operably linked to a heterologous coding sequence. In further embodiments, said plant is selected from the group consisting of *Zea mays*, wheat, rice, sorghum, oats, rye, bananas, sugar cane, *Glycine max*, cotton, *Arabidopsis*, tobacco, sunflower, and canola. In yet another embedment, said plant is *Glycine max*. In some embodiments, the heterologous coding sequence is inserted into the genome of said plant. In other embodiments, the promoter comprises a polynucleotide sequence having at least 95% sequence identity with SEQ ID NO:2 and said promoter is operably linked to a heterologous coding sequence. In additional embodiments, the transgenic plant comprises a 3' untranslated sequence. In further embodiments, said heterologous coding sequence has tissue constitutive expression. In additional embodiments, the transgenic plant comprises said promoter of 371 bp in length.

In embodiments of the subject disclosure, the disclosure relates to a method for producing a transgenic plant cell, the method comprising the steps of transforming a plant cell with a gene expression cassette comprising a GmTEFs1 promoter operably linked to at least one polynucleotide sequence of interest; isolating the transformed plant cell comprising the gene expression cassette; and, producing a transgenic plant cell comprising the GmTEFs1 promoter operably linked to at least one polynucleotide sequence of interest. In other embodiments, the transformation of a plant cell is performed with a plant transformation method. In some aspects, the plant transformation method is selected from the group consisting of an *Agrobacterium*-mediated transformation method, a biolistics transformation method, a silicon carbide transformation method, a protoplast transformation method, and a liposome transformation method. In further embodiments, the polynucleotide sequence of interest is expressed in a plant cell. In other embodiments, the polynucleotide sequence of interest is stably integrated into the genome of the transgenic plant cell. In further embodiments, the method comprises regenerating the transgenic plant cell into a transgenic plant; and, obtaining the transgenic plant, wherein the transgenic plant comprising the gene expression cassette comprising the GmTEFs1 promoter of operably linked to at least one polynucleotide sequence of interest. In other embodiments, the transgenic plant cell is a monocotyledonous transgenic plant cell or a dicotyledonous transgenic plant cell. Examples of a dicotyledonous transgenic plant cell includes an *Arabidopsis* plant cell, a tobacco plant cell, a *Glycine max* plant cell, a canola plant cell, and a cotton plant cell. Examples of a monocotyledonous transgenic plant cell includes a *Zea mays* plant cell, a rice plant cell, and a wheat plant cell. In some embodiments, the GmTEFs1 promoter comprises the polynucleotide of SEQ ID NO:2. In other embodiments, the GmTEFs1 promoter comprises a first polynucleotide sequence of interest operably linked to the 3' end of SEQ ID NO:2. In additional embodiments, the method comprises introducing into the plant cell a polynucleotide sequence of interest operably linked to a GmTEFs1 promoter. In further embodiments, the polynucleotide sequence of interest operably linked to the GmTEFs1 promoter is introduced into the plant cell by a plant transformation method. Examples of plant transformation methods include *Agrobacterium*-mediated transformation method, a biolistics transformation method, a silicon carbide transformation method, a protoplast transformation method, and a liposome transformation method. In further embodiments, the polynucleotide sequence of interest is expressed in embryonic cell tissue. In additional embodiments, the polynucleotide sequence of interest is stably integrated into the genome of the plant cell. In some embodiments, the transgenic plant cell is a monocotyledonous plant cell or a dicotyledonous plant cell. Examples of dicotyledonous plant cells include an *Arabidopsis* plant cell, a tobacco plant cell, a *Glycine max* plant cell, a canola plant cell, and a cotton plant cell. Examples of monocotyledonous plant cells include a *Zea mays* plant cell, a rice plant cell, and a wheat plant cell.

In embodiments of the subject disclosure, the disclosure relates to a transgenic plant cell comprising a GmTEFs1 promoter. In other embodiments, the transgenic plant cell comprises a transgenic event. In further embodiments, the transgenic event comprises an agronomic trait. Examples of agronomic traits include an insecticidal resistance trait, herbicide tolerance trait, nitrogen use efficiency trait, water use efficiency trait, nutritional quality trait, DNA binding trait, selectable marker trait, small RNA trait, or any combination thereof. In further embodiments, the agronomic trait comprises an herbicide tolerant trait. In an aspect of this embodiment, the herbicide tolerant trait comprises an aad-1 coding sequence. In yet another embodiment, the transgenic plant cell produces a commodity product. Examples of a commodity product includes protein concentrate, protein isolate, grain, meal, flour, oil, or fiber. In further embodiments, the transgenic plant cell is selected from the group consisting of a dicotyledonous plant cell or a monocotyledonous plant cell. For example, the dicotyledonous plant cell is a *Glycine max* plant cell. In additional embodiments, the GmTEFs1 promoter comprises a polynucleotide with at least 95% sequence identity to the polynucleotide of SEQ ID NO:2. In other embodiments, the GmTEFs1 promoter is 371 bp in length. In some embodiments, the GmTEFs1 promoter consists of SEQ ID NO:2. In subsequent embodiments, the GmTEFs1 promoter comprises a first polynucleotide sequence of interest operably linked to the 3' end of SEQ ID NO:2. In other embodiments, the agronomic trait is expressed in plant tissues. In further embodiments, the isolated polynucleotide comprises a nucleic acid sequence with at least 95% sequence identity to the polynucleotide of SEQ ID NO:2. In additional embodiments, the isolated polynucleotide drives constitutive tissue expression. In other embodiments, the isolated polynucleotide comprises expression activity within a plant cell. In some embodiments, the isolated polynucleotide comprise an open-reading frame polynucleotide coding for a polypeptide; and a termination sequence. In subsequent embodiments, the polynucleotide of SEQ ID NO:2 is 371 bp in length.

In embodiments of the subject disclosure, the disclosure relates to a gene expression cassette comprising a promoter operably linked to a heterologous coding sequence, wherein the promoter comprises a polynucleotide comprising a sequence identity of at least 95% to SEQ ID NO:2. In some embodiments, the polynucleotide has at least 95% sequence identity to SEQ ID NO:2. In additional embodiments, the gene expression cassette comprises an intron. In further embodiments, the gene expression cassette comprises a 5' UTR. In subsequent embodiments, the promoter has constitutive tissue expression. In other embodiments, the promoter is operably linked to a heterologous coding sequence that encodes a polypeptide or a small RNA gene. Examples of the encoded polypeptide or small RNA gene include a heterologous coding sequence conferring insecticidal resistance, herbicide tolerance, a nucleic acid conferring nitrogen use efficiency, a nucleic acid conferring water use efficiency, a nucleic acid conferring nutritional quality, a nucleic acid encoding a DNA binding protein, and a nucleic acid encoding a selectable marker. In additional embodiments, the gene expression cassette comprises a 3' untranslated region. For example, the 3' untranslated region has at least 95% sequence identity to SEQ ID NO:4. In additional embodiments, the gene expression cassette comprises a 5' untranslated region. For example, the 5' untranslated region has at least 95% sequence identity to SEQ ID NO:3. In additional embodiments, the gene expression cassette comprises a terminator region. For example, the terminator region has at least 95% sequence identity to SEQ ID NO:5. In other embodiments the subject disclosure relates to a recombinant vector comprising the gene expression cassette, wherein the vector is selected from the group consisting of a plasmid, a cosmid, a bacterial artificial chromosome, a virus, and a bacteriophage. In other embodiments the subject disclosure relates to a transgenic cell comprising the gene expression cassette. In an aspect of this embodiment, the transgenic cell is a transgenic plant cell. In other aspects of this embodiment the transgenic plant comprises the transgenic plant cell. In further aspects the transgenic plant is a monocotyledonous plant or dicotyledonous plant. Examples of a monocotyledonous plant is include a maize plant, a rice plant, and a wheat plant. In further aspects of the embodiment, the transgenic plant produces a seed comprising the gene expression cassette. In other embodiments, the promoter is a constitutive tissue promoter. In some embodiments, the promoter is a constitutive promoter.

The foregoing and other features will become more apparent from the following detailed description of several embodiments, which proceeds with reference to the accompanying figures.

BRIEF DESCRIPTION OF THE FIGURES

FIG. 1. Provides a figure of a linear synthetic DNA fragment containing GmTEFs1 promoter, 5' UTR and terminator linked by the multiple cloning site.

DETAILED DESCRIPTION

I. Overview of Several Embodiments

Development of transgenic plant products is becoming increasingly complex. Commercially viable transgenic plants now require the stacking of multiple transgenes into a single locus. Plant promoters and 3' UTRs/terminators used for basic research or biotechnological applications are generally unidirectional, directing only one gene that has been fused at its 3' end (downstream) for the promoter, or at its 5' end (upstream) for the 3' UTR/terminator. Accordingly, each transgene/heterologous coding sequence usually requires a promoter and 3' UTR/terminator for expression, wherein multiple regulatory elements are required to express multiple transgenes within one gene stack. With an increasing number of transgenes in gene stacks, the same promoter and/or 3' UTR/terminator is routinely used to obtain optimal levels of expression patterns of different transgenes. Obtaining optimal levels of transgene/heterologous coding sequence expression is necessary for the production of a single polygenic trait. Unfortunately, multi-gene constructs driven by the same promoter and/or 3' UTR/terminator are known to cause gene silencing resulting in less efficacious transgenic products in the field. The repeated promoter and/or 3' UTR/terminator elements may lead to homology-based gene silencing. In addition, repetitive sequences within a transgene/heterologous coding sequence may lead to gene intra locus homologous recombination resulting in polynucleotide rearrangements. The silencing and rearrangement of transgenes will likely have an undesirable affect on the performance of a transgenic plant produced to express transgenes. Further, excess of transcription factor (TF)-binding sites due to promoter repetition can cause depletion of endogenous TFs leading to transcriptional inactivation. Given the need to introduce multiple genes into plants for metabolic engineering and trait stacking, a variety of promoters and/or 3' UTRs/terminators are required to develop transgenic crops that drive the expression of multiple genes.

A particular problem in promoter and/or 3' UTR/terminator identification is the need to identify tissue-specific/preferred promoters, related to specific cell types, developmental stages and/or functions in the plant that are not expressed in other plant tissues. Tissue specific (i.e., tissue preferred) or organ specific promoters drive gene expression in a certain tissue such as in the kernel, root, leaf, or tapetum of the plant. Tissue and developmental stage specific promoters and/or 3' UTRs/terminators can be initially identified from observing the expression of genes, which are expressed in particular tissues or at particular time periods during plant development. These tissue specific/preferred promoters and/or 3' UTRs/terminators are required for certain applications in the transgenic plant industry and are desirable as they permit specific expression of heterologous genes in a tissue and/or developmental stage selective manner, indicating expression of the heterologous gene differentially at various organs, tissues and/or times, but not in other undesirable tissues. For example, increased resistance of a plant to infection by soil-borne pathogens might be accomplished by transforming the plant genome with a pathogen-resistance gene such that pathogen-resistance protein is robustly expressed within the roots of the plant. Alternatively, it may be desirable to express a transgene/heterologous coding sequence in plant tissues that are in a particular growth or developmental phase such as, for example, cell division or elongation. Another application is the desirability of using tissue specific/preferred promoters and/or 3' UTRs/terminators to confine the expression of the transgenes encoding an agronomic trait in specific tissues types like developing parenchyma cells. As such, a particular problem in the identification of promoters and/or 3' UTRs/terminators is how to identify the promoters, and to relate the identified promoter to developmental properties of the cell for specific/preferred tissue expression.

Another problem regarding the identification of a promoter is the requirement to clone all relevant cis-acting and trans-activating transcriptional control elements so that the cloned DNA fragment drives transcription in the wanted specific expression pattern. Given that such control elements are located distally from the translation initiation or start site, the size of the polynucleotide that is selected to comprise the promoter is of importance for providing the level of expression and the expression patterns of the promoter polynucleotide sequence. It is known that promoter lengths include functional information, and different genes have been shown to have promoters longer or shorter than promoters of the other genes in the genome. Elucidating the transcription start site of a promoter and predicting the functional gene elements in the promoter region is challenging. Further adding to the challenge are the complexity, diversity and inherent degenerate nature of regulatory motifs and cis- and trans-regulatory elements (Blanchette, Mathieu, et al. "Genome-wide computational prediction of transcriptional regulatory modules reveals new insights into human gene expression." *Genome research* 16.5 (2006): 656-668). The cis- and trans-regulatory elements are located in the distal parts of the promoter which regulate the spatial and temporal expression of a gene to occur only at required sites and at specific times (Porto, Milena Silva, et al. "Plant promoters: an approach of structure and function." *Molecular biotechnology* 56.1 (2014): 38-49). Accordingly, the identification of promoter regulatory elements requires that an appropriate sequence of a specific size containing the necessary cis- and trans-regulatory elements is obtained that will result in driving expression of an operably linked transgene/heterologous coding sequence in a desirable manner.

Provided are methods and compositions for overcoming such problems through the use of GmTEFs1 gene regulatory elements to express transgenes in planta.

II. Terms and Abbreviations

Throughout the application, a number of terms are used. In order to provide a clear and consistent understanding of the specification and claims, including the scope to be given such terms, the following definitions are provided.

As used herein, the articles, "a," "an," and "the" include plural references unless the context clearly and unambiguously dictates otherwise.

The term "isolated", as used herein means having been removed from its natural environment, or removed from other compounds present when the compound is first formed. The term "isolated" embraces materials isolated from natural sources as well as materials (e.g., nucleic acids and proteins) recovered after preparation by recombinant expression in a host cell, or chemically-synthesized compounds such as nucleic acid molecules, proteins, and peptides.

The term "purified", as used herein relates to the isolation of a molecule or compound in a form that is substantially free of contaminants normally associated with the molecule or compound in a native or natural environment, or substantially enriched in concentration relative to other compounds present when the compound is first formed, and means having been increased in purity as a result of being separated from other components of the original composition. The term "purified nucleic acid" is used herein to describe a nucleic acid sequence which has been separated, produced apart from, or purified away from other biological compounds including, but not limited to polypeptides, lipids and carbohydrates, while effecting a chemical or functional change in the component (e.g., a nucleic acid may be purified from a chromosome by removing protein contaminants and breaking chemical bonds connecting the nucleic acid to the remaining DNA in the chromosome).

The term "synthetic", as used herein refers to a polynucleotide (i.e., a DNA or RNA) molecule that was created via chemical synthesis as an in vitro process. For example, a synthetic DNA may be created during a reaction within an Eppendor™ tube, such that the synthetic DNA is enzymatically produced from a native strand of DNA or RNA. Other laboratory methods may be utilized to synthesize a polynucleotide sequence. Oligonucleotides may be chemically synthesized on an oligo synthesizer via solid-phase synthesis using phosphoramidites. The synthesized oligonucleotides may be annealed to one another as a complex, thereby producing a "synthetic" polynucleotide. Other methods for chemically synthesizing a polynucleotide are known in the art, and can be readily implemented for use in the present disclosure.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

For the purposes of the present disclosure, a "gene," includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, introns and locus control regions.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

As used herein a "transgene" is defined to be a nucleic acid sequence that encodes a gene product, including for example, but not limited to, an mRNA. In one embodiment the transgene/heterologous coding sequence is an exogenous nucleic acid, where the transgene/heterologous coding sequence has been introduced into a host cell by genetic engineering (or the progeny thereof) where the transgene/heterologous coding sequence is not normally found. In one example, a transgene/heterologous coding sequence encodes an industrially or pharmaceutically useful compound, or a gene encoding a desirable agricultural trait (e.g., an herbicide-resistance gene). In yet another example, a transgene/heterologous coding sequence is an antisense nucleic acid sequence, wherein expression of the antisense nucleic acid sequence inhibits expression of a target nucleic acid sequence. In one embodiment the transgene/heterologous coding sequence is an endogenous nucleic acid, wherein additional genomic copies of the endogenous nucleic acid are desired, or a nucleic acid that is in the antisense orientation with respect to the sequence of a target nucleic acid in a host organism.

As used herein the term "non-GmTEFs1 transgene" or "non-GmTEFs1 gene" is any transgene/heterologous coding sequence that has less than 80% sequence identity with the GmTEFs1 gene coding sequence.

As used herein, "heterologous DNA coding sequence" means any coding sequence other than the one that naturally encodes the GmTEFs1 gene, or any homolog of the expressed GmTEFs1 protein. The term "heterologous" is used in the context of this invention for any combination of nucleic acid sequences that is not normally found intimately associated in nature.

A "gene product" as defined herein is any product produced by the gene. For example the gene product can be the direct transcriptional product of a gene (e.g., mRNA, tRNA, rRNA, antisense RNA, interfering RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation. Gene expression can be influenced by external signals, for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein the term "gene expression" relates to the process by which the coded information of a nucleic acid transcriptional unit (including, e.g., genomic DNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein, "homology-based gene silencing" (HBGS) is a generic term that includes both transcriptional gene silencing and post-transcriptional gene silencing. Silencing of a target locus by an unlinked silencing locus can result from transcription inhibition (transcriptional gene silencing; TGS) or mRNA degradation (post-transcriptional gene silencing; PTGS), owing to the production of double-stranded RNA (dsRNA) corresponding to promoter or transcribed sequences, respectively. The involvement of distinct cellular components in each process suggests that dsRNA-induced TGS and PTGS likely result from the diversification of an ancient common mechanism. However, a strict comparison of TGS and PTGS has been difficult to achieve because it generally relies on the analysis of distinct silencing loci. In some instances, a single transgene locus can triggers both TGS and PTGS, owing to the production of dsRNA corresponding to promoter and transcribed sequences of different target genes. Mourrain et al. (2007) *Planta* 225:365-79. It is likely that siRNAs are the actual molecules that trigger TGS and PTGS on homologous sequences: the siRNAs would in this model trigger silencing and methylation of homologous sequences in cis and in trans through the spreading of methylation of transgene sequences into the endogenous promoter.

As used herein, the term "nucleic acid molecule" (or "nucleic acid" or "polynucleotide") may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide". A nucleic acid molecule is usually at least 10 bases in length, unless otherwise specified. The term may refer to a molecule of RNA or DNA of indeterminate length. The term includes single- and double-stranded forms of DNA. A nucleic acid molecule may include either or both naturally-occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidites, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Transcription proceeds in a 5' to 3' manner along a DNA strand. This means that RNA is made by the sequential addition of ribonucleotide-5'-triphosphates to the 3' terminus of the growing chain (with a requisite elimination of the pyrophosphate). In either a linear or circular nucleic acid molecule, discrete elements (e.g., particular nucleotide sequences) may be referred to as being "upstream" or "5'" relative to a further element if they are bonded or would be bonded to the same nucleic acid in the 5' direction from that element. Similarly, discrete elements may be "downstream" or "3'" relative to a further element if they are or would be bonded to the same nucleic acid in the 3' direction from that element.

A base "position", as used herein, refers to the location of a given base or nucleotide residue within a designated nucleic acid. The designated nucleic acid may be defined by alignment (see below) with a reference nucleic acid.

Hybridization relates to the binding of two polynucleotide strands via Hydrogen bonds. Oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide and the DNA or RNA target. The oligonucleotide need not be 100% complementary to its target sequence to be specifically hybridizable. An oligonucleotide is specifically hybridizable when binding of the oligonucleotide to the target DNA or RNA molecule interferes with the normal function of the target DNA or RNA, and there is sufficient degree of complementarity to avoid non-specific binding of the oligonucleotide to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the chosen hybridization method and the composition and length of the hybridizing nucleic acid sequences. Generally, the temperature of hybridization and the ionic strength (especially the Na+ and/or Mg2+ concentration) of the hybridization buffer will contribute to the stringency of hybridization, though wash times also influence stringency. Calculations regarding hybridization conditions required for attaining particular degrees of stringency are discussed in Sambrook et al. (ed.), *Molecular Cloning: A Laboratory Manual,* 2nd ed., vol. 1-3, Cold Spring Harbor Laboratory Press, Cold Spring Harbor, New York, 1989, chs. 9 and 11.

As used herein, "stringent conditions" encompass conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

In particular embodiments, stringent conditions can include hybridization at 65° C., followed by washes at 65° C. with 0.1×SSC/0.1% SDS for 40 minutes.

The following are representative, non-limiting hybridization conditions:

Very High Stringency: Hybridization in 5×SSC buffer at 65° C. for 16 hours; wash twice in 2×SSC buffer at room temperature for 15 minutes each; and wash twice in 0.5×SSC buffer at 65° C. for 20 minutes each.

High Stringency: Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency: Hybridization in 6×SSC buffer at room temperature to 55° C. for 16-20 hours; wash at least twice in 2×-3×SSC buffer at room temperature to 55° C. for 20-30 minutes each.

In particular embodiments, specifically hybridizable nucleic acid molecules can remain bound under very high stringency hybridization conditions. In these and further embodiments, specifically hybridizable nucleic acid molecules can remain bound under high stringency hybridization conditions. In these and further embodiments, specifically hybridizable nucleic acid molecules can remain bound under moderate stringency hybridization conditions.

As used herein, the term "oligonucleotide" refers to a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of small DNA sequences. In PCR, the oligonucleotide is typically referred to as a "primer", which allows a DNA polymerase to extend the oligonucleotide and replicate the complementary strand.

The terms "percent sequence identity" or "percent identity" or "identity" are used interchangeably to refer to a sequence comparison based on identical matches between correspondingly identical positions in the sequences being compared between two or more amino acid or nucleotide sequences. The percent identity refers to the extent to which two optimally aligned polynucleotide or peptide sequences are invariant throughout a window of alignment of components, e.g., nucleotides or amino acids. Hybridization experiments and mathematical algorithms known in the art may be used to determine percent identity. Many mathematical algorithms exist as sequence alignment computer programs known in the art that calculate percent identity. These programs may be categorized as either global sequence alignment programs or local sequence alignment programs.

Global sequence alignment programs calculate the percent identity of two sequences by comparing alignments end-to-end in order to find exact matches, dividing the number of exact matches by the length of the shorter sequences, and then multiplying by 100. Basically, the percentage of identical nucleotides in a linear polynucleotide sequence of a reference ("query) polynucleotide molecule as compared to a test ("subject") polynucleotide molecule when the two sequences are optimally aligned (with appropriate nucleotide insertions, deletions, or gaps).

Local sequence alignment programs are similar in their calculation, but only compare aligned fragments of the sequences rather than utilizing an end-to-end analysis. Local sequence alignment programs such as BLAST can be used to compare specific regions of two sequences. A BLAST comparison of two sequences results in an E-value, or expectation value, that represents the number of different alignments with scores equivalent to or better than the raw alignment score, S, that are expected to occur in a database search by chance. The lower the E value, the more significant the match. Because database size is an element in E-value calculations, E-values obtained by BLASTing against public databases, such as GENBANK, have generally increased over time for any given query/entry match. In setting criteria for confidence of polypeptide function prediction, a "high" BLAST match is considered herein as having an E-value for the top BLAST hit of less than 1E-30; a medium BLASTX E-value is 1E-30 to 1E-8; and a low BLASTX E-value is greater than 1E-8. The protein function assignment in the present invention is determined using combinations of E-values, percent identity, query coverage and hit coverage. Query coverage refers to the percent of the query sequence that is represented in the BLAST alignment. Hit coverage refers to the percent of the database entry that is represented in the BLAST alignment. In one embodiment of the invention, function of a query polypeptide is inferred from function of a conserved protein sequence where either (1) hit p<1e-30 or % identity >35% AND query_coverage >50% AND hit_coverage >50%, or (2) hit p<1e-8 AND query_coverage >70% AND hit_coverage >70%. The following abbreviations are produced during a BLAST analysis of a sequence.

Methods for aligning sequences for comparison are well-known in the art. Various programs and alignment algorithms are described. In an embodiment, the subject disclosure relates to calculating percent identity between two polynucleotides or amino acid sequences using an AlignX alignment program of the Vector NTI suite (Invitrogen, Carlsbad, CA). The AlignX alignment program is a global sequence alignment program for polynucleotides or proteins. In an embodiment, the subject disclosure relates to calculating percent identity between two polynucleotides or amino acid sequences using the MegAlign program of the LASERGENE bioinformatics computing suite (MegAlign™ ©1993-2016). DNASTAR. Madison, WI). The MegAlign program is global sequence alignment program for polynucleotides or proteins. In an embodiment, the subject disclosure relates to calculating percent identity between two polynucleotides or amino acid sequences using the Clustal suite of alignment programs, including, but not limited to, ClustalW and ClustalV (Higgins and Sharp (1988) Gene. December 15; 73(1):237-44; Higgins and Sharp (1989) CABIOS 5:151-3; Higgins et al. (1992) Comput. Appl. Biosci. 8:189-91). In an embodiment, the subject disclosure relates to calculating percent identity between two polynucleotides or amino acid sequences using the GCG suite of programs (Wisconsin Package Version 9.0, Genetics Computer Group (GCG), Madison, WI). In an embodiment, the subject disclosure relates to calculating percent identity between two polynucleotides or amino acid sequences using the BLAST suite of alignment programs, for example, but not limited to, BLASTP, BLASTN, BLASTX, etc. (Altschul et al. (1990) J. Mol. Biol. 215:403-10). Further examples of such BLAST alignment programs include Gapped-BLAST or PSI-BLAST (Altschul et al., 1997). In an embodiment, the subject disclosure relates to calculating percent identity between two polynucleotides or amino acid sequences using the FASTA suite of alignment programs, including, but not limited to, FASTA, TFASTX, TFASTY, SSEARCH, LALIGN etc. (Pearson (1994) Comput. Methods Genome Res. [Proc. Int. Symp.], Meeting Date 1992 (Suhai and Sandor, Eds.), Plenum: New York, NY, pp. 111-20). In an embodiment, the subject disclosure relates to calculating percent identity between two polynucleotides or amino acid sequences using the T-Coffee alignment program (Notredame, et. al. (2000) J. Mol. Biol. 302, 205-17). In an embodiment, the subject disclosure relates to calculating percent identity between two polynucleotides or amino acid sequences using the DIALIGN suite of alignment programs, including, but not limited to DIALIGN, CHAOS, DIALIGN-TX, DIALIGN-T etc. (Al Ait, et. al. (2013) DIALIGN at GOBICS Nuc. Acids Research 41, W3-W7). In an embodiment, the subject disclosure relates to calculating percent identity between two polynucleotides or amino acid sequences using the MUSCLE suite of alignment programs (Edgar (2004) Nucleic Acids Res. 32(5): 1792-1797). In an embodiment, the subject disclosure relates to calculating percent identity between two polynucleotides or amino acid sequences using the MAFFT alignment program (Katoh, et. al. (2002) Nucleic Acids Research 30(14): 3059-3066). In an embodiment, the subject disclosure relates to calculating percent identity between two polynucleotides or amino acid sequences using the Genoogle program (Albrecht, Felipe. arXiv150702987v1 [cs.DC] 10 Jul. 2015). In an embodiment, the subject disclosure relates to calculating percent identity between two polynucleotides or amino acid sequences using the HMMER suite of programs (Eddy. (1998) *Bioinformatics,* 14:755-63). In an embodiment, the subject disclosure relates to calculating percent identity between two polynucleotides or amino acid sequences using the PLAST suite of alignment programs, including, but not limited to, TPLASTN, PLASTP, KLAST, and PLASTX (Nguyen & Lavenier. (2009) *BMC Bioinformatics,* 10:329). In an embodiment, the subject disclosure relates to calculating percent identity between two polynucleotides or amino acid sequences using the USEARCH alignment program (Edgar (2010) *Bioinformatics* 26(19), 2460-61). In an embodiment, the subject disclosure relates to calculating percent identity between two polynucleotides or amino acid sequences using the SAM suite of alignment programs (Hughey & Krogh (January 1995) *Technical Report UCSC0CRL-95-7,* University of California, Santa Cruz). In an embodiment, the subject disclosure relates to calculating percent identity between two polynucleotides or amino acid sequences using the IDF Searcher (O'Kane, K. C., The Effect of Inverse Document Frequency Weights on Indexed Sequence Retrieval, *Online Journal of Bioinformatics,* Volume 6 (2) 162-173, 2005). In an embodiment, the subject disclosure relates to calculating percent identity between two polynucleotides or amino acid sequences using the Parasail alignment program. (Daily, Jeff. Parasail: SIMD C library for global, semi-global, and local pairwise sequence alignments. *BMC Bioinformatics.* 17:18. Feb. 10, 2016). In an embodiment, the subject disclosure relates to calculating percent identity between two polynucleotides or amino acid sequences using the ScalaBLAST alignment program (Oehmen C, Nieplocha J. "ScalaBLAST: A scalable implementation of BLAST for high-performance data-intensive bioinformatics analysis." *IEEE Transactions on Parallel & Distributed Systems* 17 (8): 740-749 August 2006). In an embodiment, the subject disclosure relates to calculating percent identity between two polynucleotides or amino acid sequences using the SWIPE alignment program (Rognes, T. Faster Smilth-Waterman database searches with inter-sequence SIMD parallelization. *BMC Bioinformatics.* 12, 221 (2011)). In an embodiment, the subject disclosure relates to calculating percent identity between two polynucleotides or amino acid sequences using the ACANA alignment program (Weichun Huang, David M. Umbach, and Leping Li, Accurate anchoring alignment of divergent sequences. *Bioinformatics* 22:29-34, Jan. 1, 2006). In an embodiment, the subject disclosure relates to calculating percent identity between two polynucleotides or amino acid sequences using the DOTLET alignment program (Junier, T. & Pagni, M. DOTLET: diagonal plots in a web browser. *Bioinformatics* 16(2): 178-9 Feb. 2000). In an embodiment, the subject disclosure relates to calculating percent identity between two polynucleotides or amino acid sequences using the G-PAS alignment program (Frohmberg, W., et al. G-PAS 2.0—an improved version of protein alignment tool with an efficient backtracking routine on multiple GPUs. *Bulletin of the Polish Academy of Sciences Technical Sciences,* Vol. 60, 491 November 2012). In an embodiment, the subject disclosure relates to calculating percent identity between two polynucleotides or amino acid sequences using the GapMis alignment program (Flouri, T. et. al., Gap Mis: A tool for pairwise sequence alignment with a single gap. *Recent Pat DNA Gene Seq.* 7(2): 84-95 August 2013). In an embodiment, the subject disclosure relates to calculating percent identity between two polynucleotides or amino acid sequences using the EMBOSS suite of alignment programs, including, but not limited to: Matcher, Needle, Stretcher, Water, Wordmatch, etc. (Rice, P., Longden, I. & Bleasby, A. EMBOSS: The European Molecular Biology Open Software Suite. *Trends in Genetics* 16(6) 276-77 (2000)). In an embodiment, the subject disclosure relates to calculating percent identity between two polynucleotides or amino acid sequences using the Ngila alignment program (Cartwright, R. Ngila: global pairwise alignments with logarithmic and affine gap costs. *Bioinformatics.* 23(11): 1427-28. Jun. 1, 2007). In an embodiment, the subject disclosure relates to calculating percent identity between two polynucleotides or amino acid sequences using the probA, also known as propA, alignment program (Muckstein, U., Hofacker, IL, & Stadler, PF. Stochastic pairwise alignments. *Bioinformatics* 18 Suppl. 2: S153-60. 2002). In an embodiment, the subject disclosure relates to calculating percent identity between two polynucleotides or amino acid sequences using the SEQALN suite of alignment programs (Hardy, P. & Waterman, M. *The Sequence Alignment Software Library at USC.* 1997). In an embodiment, the subject disclosure relates to calculating percent identity between two polynucleotides or amino acid sequences using the SIM suite of alignment programs, including, but not limited to, GAP, NAP, LAP, etc. (Huang, X & Miller, W. A Time-Efficient, Linear-Space Local Similarity Algorithm. *Advances in Applied Mathematics,* vol. 12 (1991) 337-57). In an embodiment, the subject disclosure relates to calculating percent identity between two polynucleotides or amino acid sequences using the UGENE alignment program (Okonechnikov, K., Golosova, O. & Fursov, M. Unipro UGENE: a unified bioinformatics toolkit. *Bioinformatics.* 2012 28:1166-67). In an embodiment, the subject disclosure relates to calculating percent identity between two polynucleotides or amino acid sequences using the BAli-Phy alignment program (Suchard, MA & Redelings, BD. BAli-Phy: simultaneous Bayesian inference of alignment and phylogeny. *Bioinformatics.* 22:2047-48. 2006). In an embodiment, the subject disclosure relates to calculating percent identity between two polynucleotides or amino acid sequences using the Base-By-Base alignment program (Brodie, R., et. al. Base-By-Base: Single nucleotide-level analysis of whole viral genome alignments, *BMC Bioinformatics,* 5, 96, 2004). In an embodiment, the subject disclosure relates to calculating percent identity between two polynucleotides or amino acid sequences using the DECIPHER alignment program (E S Wright (2015) "DECIPHER: harnessing local sequence context to improve protein multiple sequence alignment." *BMC Bioinformatics,* doi:10.1186/s12859-015-0749-z.). In an embodiment, the subject disclosure relates to calculating percent identity between two polynucleotides or amino acid sequences using the FSA alignment program (Bradley, R K, et. al. (2009) Fast Statistical Alignment. *PLoS Computational Biology.* 5: e1000392). In an embodiment, the subject disclosure relates to calculating percent identity between two polynucleotides or amino acid sequences using the Geneious alignment program (Kearse, M., et. al. (2012). Geneious Basic: an integrated and extendable desktop software platform for the organization and analysis of sequence data. *Bioinformatics,* 28(12), 1647-49). In an embodiment, the subject disclosure relates to calculating percent identity between two polynucleotides or amino acid sequences using the Kalign alignment program (Lassmann, T. & Sonnhammer, E. Kalign—an accurate and fast multiple sequence alignment algorithm. *BMC Bioinformatics* 2005 6:298). In an embodiment, the subject disclosure relates to calculating percent identity between two polynucleotides or amino acid sequences using the MAVID alignment program (Bray, N. & Pachter, L. MAVID: Constrained Ancestral Alignment of Multiple Sequences. *Genome Res.* 2004 April; 14(4): 693-99). In an embodiment, the subject disclosure relates to calculating percent identity between two polynucleotides or amino acid sequences using the MSA alignment program (Lipman, D J, et. al. A tool for multiple sequence alignment. *Proc. Nat'l Acad. Sci. USA.* 1989; 86:4412-15). In an embodiment, the subject disclosure relates to calculating percent identity between two polynucleotides or amino acid sequences using the MultAlin alignment program (Corpet, F., Multiple sequence alignment with hierarchical clustering. *Nucl. Acids Res.*, 1988, 16(22), 10881-90). In an embodiment, the subject disclosure relates to calculating percent identity between two polynucleotides or amino acid sequences using the LAGAN or MLAGAN alignment programs (Brudno, et. al. LAGAN and Multi-LAGAN: efficient tools for large-scale multiple alignment of genomic DNA. *Genome Research* 2003 April; 13(4): 721-31). In an embodiment, the subject disclosure relates to calculating percent identity between two polynucleotides or amino acid sequences using the Opal alignment program (Wheeler, T. J., & Kececiouglu, J. D. Multiple alignment by aligning alignments. Proceedings of the 15$^{th}$ ISCB conference on Intelligent Systems for Molecular Biology. *Bioinformatics.* 23, i559-68, 2007). In an embodiment, the subject disclosure relates to calculating percent identity between two polynucleotides or amino acid sequences using the PicXAA suite of programs, including, but not limited to, PicXAA, PicXAA-R, PicXAA-Web, etc. (Mohammad, S., Sahraeian, E. & Yoon, B. PicXAA: greedy probabilistic construction of maximum expected accuracy alignment of multiple sequences. *Nucleic Acids Research.* 38(15):4917-28. 2010). In an embodiment, the subject disclosure relates to calculating percent identity between two polynucleotides or amino acid sequences using the PSAlign alignment program (SZE, S.-H., Lu, Y., & Yang, Q. (2006) A polynomial time solvable formulation of multiple sequence alignment *Journal of Computational Biology,* 13, 309-19). In an embodiment, the subject disclosure relates to calculating percent identity between two polynucleotides or amino acid sequences using the StatAlign alignment program (Novak, A., et. al. (2008) StatAlign: an extendable software package for joint Bayesian estimation of alignments and evolutionary trees. *Bioinformatics,* 24(20):2403-04). In an embodiment, the subject disclosure relates to calculating percent identity between two polynucleotides or amino acid sequences using the Gap alignment program of Needleman and Wunsch (Needleman and Wunsch, *Journal of Molecular Biology* 48:443-453, 1970). In an embodiment, the subject disclosure relates to calculating percent identity between two polynucleotides or amino acid sequences using the BestFit alignment program of Smith and Waterman (Smith and Waterman, *Advances in Applied Mathematics,* 2:482-489, 1981, Smith et al., *Nucleic Acids Research* 11:2205-2220, 1983). These programs produces biologically meaningful multiple sequence alignments of divergent sequences. The calculated best match alignments for the selected sequences are lined up so that identities, similarities, and differences can be seen.

The term "similarity" refers to a comparison between amino acid sequences, and takes into account not only identical amino acids in corresponding positions, but also functionally similar amino acids in corresponding positions. Thus similarity between polypeptide sequences indicates functional similarity, in addition to sequence similarity.

The term "homology" is sometimes used to refer to the level of similarity between two or more nucleic acid or amino acid sequences in terms of percent of positional identity (i.e., sequence similarity or identity). Homology also refers to the concept of evolutionary relatedness, often evidenced by similar functional properties among different nucleic acids or proteins that share similar sequences.

As used herein, the term "variants" means substantially similar sequences. For nucleotide sequences, naturally occurring variants can be identified with the use of well-known molecular biology techniques, such as, for example, with polymerase chain reaction (PCR) and hybridization techniques as outlined herein.

For nucleotide sequences, a variant comprises a deletion and/or addition of one or more nucleotides at one or more internal sites within the native polynucleotide and/or a substitution of one or more nucleotides at one or more sites in the native polynucleotide. As used herein, a "native" nucleotide sequence comprises a naturally occurring nucleotide sequence. For nucleotide sequences, naturally occurring variants can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the invention will have at least about 40%, 45%, 50%>, 55%, 60%, 65%, 70%, 75%, 80%, 85%, 90%, 91%, 92%, 93%, 94%, 95%, 96%, 97%, 98%0, 99% or more sequence identity to that particular nucleotide sequence as determined by sequence alignment programs and parameters described elsewhere herein. A biologically active variant of a nucleotide sequence of the invention may differ from that sequence by as few as 1-15 nucleic acid residues, as few as 1-10, such as 6-10, as few as 5, as few as 4, 3, 2, or even 1 nucleic acid residue.

As used herein the term "operably linked" relates to a first nucleic acid sequence is operably linked with a second nucleic acid sequence when the first nucleic acid sequence is in a functional relationship with the second nucleic acid sequence. For instance, a promoter is operably linked with a coding sequence when the promoter affects the transcription or expression of the coding sequence. When recombinantly produced, operably linked nucleic acid sequences are generally contiguous and, where necessary to join two protein-coding regions, in the same reading frame. However, elements need not be contiguous to be operably linked.

As used herein, the term "promoter" refers to a region of DNA that generally is located upstream (towards the 5' region of a gene) of a gene and is needed to initiate and drive transcription of the gene. A promoter may permit proper activation or repression of a gene that it controls. A promoter may contain specific sequences that are recognized by transcription factors. These factors may bind to a promoter DNA sequence, which results in the recruitment of RNA polymerase, an enzyme that synthesizes RNA from the coding region of the gene. The promoter generally refers to all gene regulatory elements located upstream of the gene, including, upstream promoters, 5' UTR, introns, and leader sequences.

As used herein, the term "upstream-promoter" refers to a contiguous polynucleotide sequence that is sufficient to direct initiation of transcription. As used herein, an upstream-promoter encompasses the site of initiation of transcription with several sequence motifs, which include TATA Box, initiator sequence, TFIIB recognition elements and other promoter motifs (Jennifer, E. F. et al., (2002) *Genes & Dev.*, 16: 2583-2592). The upstream promoter provides the site of action to RNA polymerase II which is a multi-subunit enzyme with the basal or general transcription factors like, TFIIA, B, D, E, F and H. These factors assemble into a transcription pre initiation complex that catalyzes the synthesis of RNA from DNA template.

The activation of the upstream-promoter is done by the additional sequence of regulatory DNA sequence elements to which various proteins bind and subsequently interact with the transcription initiation complex to activate gene expression. These gene regulatory elements sequences interact with specific DNA-binding factors. These sequence motifs may sometimes be referred to as cis-elements. Such cis-elements, to which tissue-specific or development-specific transcription factors bind, individually or in combination, may determine the spatiotemporal expression pattern of a promoter at the transcriptional level. These cis-elements vary widely in the type of control they exert on operably linked genes. Some elements act to increase the transcription of operably-linked genes in response to environmental responses (e.g., temperature, moisture, and wounding). Other cis-elements may respond to developmental cues (e.g., germination, seed maturation, and flowering) or to spatial information (e.g., tissue specificity). See, for example, Langridge et al., (1989) Proc. Natl. Acad. Sci. USA 86:3219-23. These cis-elements are located at a varying distance from transcription start point, some cis-elements (called proximal elements) are adjacent to a minimal core promoter region while other elements can be positioned several kilobases upstream or downstream of the promoter (enhancers).

As used herein, the terms "5' untranslated region" or "5' UTR" is defined as the untranslated segment in the 5' terminus of pre-mRNAs or mature mRNAs. For example, on mature mRNAs, a 5' UTR typically harbors on its 5' end a 7-methylguanosine cap and is involved in many processes such as splicing, polyadenylation, mRNA export towards the cytoplasm, identification of the 5' end of the mRNA by the translational machinery, and protection of the mRNAs against degradation.

As used herein, the term "intron" refers to any nucleic acid sequence comprised in a gene (or expressed polynucleotide sequence of interest) that is transcribed but not translated. Introns include untranslated nucleic acid sequence within an expressed sequence of DNA, as well as the corresponding sequence in RNA molecules transcribed therefrom. A construct described herein can also contain sequences that enhance translation and/or mRNA stability such as introns. An example of one such intron is the first intron of gene II of the histone H3 variant of *Arabidopsis thaliana* or any other commonly known intron sequence. Introns can be used in combination with a promoter sequence to enhance translation and/or mRNA stability.

As used herein, the terms "transcription terminator" or "terminator" is defined as the transcribed segment in the 3' terminus of pre-mRNAs or mature mRNAs. For example, longer stretches of DNA beyond "polyadenylation signal" site is transcribed as a pre-mRNA. This DNA sequence usually contains transcription termination signal for the proper processing of the pre-mRNA into mature mRNA.

As used herein, the term "3' untranslated region" or "3' UTR" is defined as the untranslated segment in a 3' terminus of the pre-mRNAs or mature mRNAs. For example, on mature mRNAs this region harbors the poly-(A) tail and is known to have many roles in mRNA stability, translation initiation, and mRNA export. In addition, the 3' UTR is considered to include the polyadenylation signal and transcription terminator.

As used herein, the term "polyadenylation signal" designates a nucleic acid sequence present in mRNA transcripts that allows for transcripts, when in the presence of a poly-(A) polymerase, to be polyadenylated on the polyadenylation site, for example, located 10 to 30 bases downstream of the poly-(A) signal. Many polyadenylation signals are known in the art and are useful for the present invention. An exemplary sequence includes AAUAAA and variants thereof, as described in Loke J., et al., (2005) Plant Physiology 138(3); 1457-1468.

A "DNA binding transgene" is a polynucleotide coding sequence that encodes a DNA binding protein. The DNA binding protein is subsequently able to bind to another molecule. A binding protein can bind to, for example, a DNA molecule (a DNA-binding protein), a RNA molecule (an RNA-binding protein), and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding, and protein-binding activity.

Examples of DNA binding proteins include; meganucleases, zinc fingers, CRISPRs, and TALEN binding domains that can be "engineered" to bind to a predetermined nucleotide sequence. Typically, the engineered DNA binding proteins (e.g., zinc fingers, CRISPRs, or TALENs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP, CRISPR, and/or TALEN designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication Nos. 20110301073, 20110239315 and 20119145940.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; 6,534,261 and 6,794,136; see also WO 98/53058; WO 98/53059; WO 98/53060; WO 02/016536 and WO 03/016496.

In other examples, the DNA-binding domain of one or more of the nucleases comprises a naturally occurring or engineered (non-naturally occurring) TAL effector DNA binding domain. See, e.g., U.S. Patent Publication No. 20110301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than different effector proteins into the plant cell. Among these injected proteins are transcription activator-like (TALEN) effectors which mimic plant transcriptional activators and manipulate the plant transcriptome (see Kay et al., (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al., (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al., (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar strain GMI1000 and in the biovar 4 strain RS1000 (See Heuer et al., (2007) *Appl and Enviro Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Patent Publication No. 20110301073, incorporated by reference in its entirety.

Specificity of these TAL effectors depends on the sequences found in the tandem repeats. The repeated sequence comprises approximately 102 bp and the repeats are typically 91-100% homologous with each other (Bonas et al., ibid). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence (see Moscou and Bogdanove, (2009) *Science* 326:1501 and Boch et al., (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al., ibid). Engineered TAL proteins have been linked to a FokI cleavage half domain to yield a TAL effector domain nuclease fusion (TALEN) exhibiting activity in a yeast reporter assay (plasmid based target).

The CRISPR (Clustered Regularly Interspaced Short Palindromic Repeats)/Cas (CRISPR Associated) nuclease system is a recently engineered nuclease system based on a bacterial system that can be used for genome engineering. It is based on part of the adaptive immune response of many bacteria and Archaea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA called a "protospacer." Cas9 cleaves the DNA to generate blunt ends at the double-stranded break (DSB) at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek et al., (2012) Science 337, pp. 816-821, Jinek et al., (2013), eLife 2: e00471, and David Segal, (2013) eLife 2: e00563). In other examples, the crRNA associates with the tracrRNA to guide the Cpf1 nuclease to a region homologous to the crRNA to cleave DNA with staggered ends (see Zetsche, Bernd, et al. *Cell* 163.3 (2015): 759-771). Thus, the CRISPR/Cas system can be engineered to create a DSB at a desired target in a genome, and repair of the DSB can be influenced by the use of repair inhibitors to cause an increase in error prone repair.

In other examples, the DNA binding transgene/heterologous coding sequence is a site specific nuclease that comprises an engineered (non-naturally occurring) Meganuclease (also described as a homing endonuclease). The recognition sequences of homing endonucleases or meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al., (1997) *Nucleic Acids Res.* 25:3379-30 3388; Dujon et al., (1989) *Gene* 82:115-118; Perler et al., (1994) *Nucleic Acids Res.* 22, 11127; Jasin (1996) *Trends Genet.* 12:224-228; Gimble et al., (1996) *J. Mol. Biol.* 263:163-180; Argast et al., (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al., (2002)*Molec. Cell* 10:895-905; Epinat et al., (2003) *Nucleic Acids Res.* 5 31:2952-2962; Ashworth et al., (2006) *Nature* 441:656-659; Paques et al., (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

As used herein, the term "transformation" encompasses all techniques that a nucleic acid molecule can be introduced into such a cell. Examples include, but are not limited to: transfection with viral vectors; transformation with plasmid vectors; electroporation; lipofection; microinjection (Mueller et al., (1978) *Cell* 15:579-85); *Agrobacterium*-mediated transfer; direct DNA uptake; WHISKERS™-mediated transformation; and microprojectile bombardment. These techniques may be used for both stable transformation and transient transformation of a plant cell. "Stable transformation" refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms. "Transient transformation" refers to the introduction of a nucleic acid fragment into the nucleus, or DNA-containing organelle, of a host organism resulting in gene expression without genetically stable inheritance.

An exogenous nucleic acid sequence. In one example, a transgene/heterologous coding sequence is a gene sequence (e.g., an herbicide-resistance gene), a gene encoding an industrially or pharmaceutically useful compound, or a gene encoding a desirable agricultural trait. In yet another example, the transgene/heterologous coding sequence is an antisense nucleic acid sequence, wherein expression of the antisense nucleic acid sequence inhibits expression of a target nucleic acid sequence. A transgene/heterologous coding sequence may contain regulatory sequences operably linked to the transgene/heterologous coding sequence (e.g., a promoter). In some embodiments, a polynucleotide sequence of interest is a transgene. However, in other embodiments, a polynucleotide sequence of interest is an endogenous nucleic acid sequence, wherein additional genomic copies of the endogenous nucleic acid sequence are desired, or a nucleic acid sequence that is in the antisense orientation with respect to the sequence of a target nucleic acid molecule in the host organism.

As used herein, the term a transgenic "event" is produced by transformation of plant cells with heterologous DNA, i.e., a nucleic acid construct that includes a transgene/heterologous coding sequence of interest, regeneration of a population of plants resulting from the insertion of the transgene/heterologous coding sequence into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene/heterologous coding sequence DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene/heterologous coding sequence of interest as the result of a sexual cross of one parental line that includes the inserted DNA (e.g., the original transformant and progeny resulting from selfing) and a parental line that does not contain the inserted DNA.

As used herein, the terms "Polymerase Chain Reaction" or "PCR" define a procedure or technique in which minute amounts of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51:263 (1987); Erlich, ed., PCR Technology, (Stockton Press, N Y, 1989).

As used herein, the term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized.

As used herein, the term "probe" refers to an oligonucleotide that hybridizes to a target sequence. In the TaqMan® or TaqMan®-style assay procedure, the probe hybridizes to a portion of the target situated between the annealing site of the two primers. A probe includes about eight nucleotides, about ten nucleotides, about fifteen nucleotides, about twenty nucleotides, about thirty nucleotides, about forty nucleotides, or about fifty nucleotides. In some embodiments, a probe includes from about eight nucleotides to about fifteen nucleotides. A probe can further include a detectable label, e.g., a fluorophore (Texas-Red©, Fluorescein isothiocyanate, etc.,). The detectable label can be covalently attached directly to the probe oligonucleotide, e.g., located at the probe's 5' end or at the probe's 3' end. A probe including a fluorophore may also further include a quencher, e.g., Black Hole Quencher™, Iowa Black™, etc.

As used herein, the terms "restriction endonucleases" and "restriction enzymes" refer to bacterial enzymes, each of which cut double-stranded DNA at or near a specific nucleotide sequence. Type-2 restriction enzymes recognize and cleave DNA at the same site, and include but are not limited to XbaI, BamHI, HindIII, EcoRI, XhoI, SalI, KpnI, AvaI, PstI and SmaI.

As used herein, the term "vector" is used interchangeably with the terms "construct", "cloning vector" and "expression vector" and means the vehicle by which a DNA or RNA sequence (e.g. a foreign gene) can be introduced into a host cell, so as to transform the host and promote expression (e.g. transcription and translation) of the introduced sequence. A "non-viral vector" is intended to mean any vector that does not comprise a virus or retrovirus. In some embodiments a "vector" is a sequence of DNA comprising at least one origin of DNA replication and at least one selectable marker gene. Examples include, but are not limited to, a plasmid, cosmid, bacteriophage, bacterial artificial chromosome (BAC), or virus that carries exogenous DNA into a cell. A vector can also include one or more genes, antisense molecules, and/or selectable marker genes and other genetic elements known in the art. A vector may transduce, transform, or infect a cell, thereby causing the cell to express the nucleic acid molecules and/or proteins encoded by the vector.

The term "plasmid" defines a circular strand of nucleic acid capable of autosomal replication in either a prokaryotic or a eukaryotic host cell. The term includes nucleic acid which may be either DNA or RNA and may be single- or double-stranded. The plasmid of the definition may also include the sequences which correspond to a bacterial origin of replication.

As used herein, the term "selectable marker gene" as used herein defines a gene or other expression cassette which encodes a protein which facilitates identification of cells into which the selectable marker gene is inserted. For example a "selectable marker gene" encompasses reporter genes as well as genes used in plant transformation to, for example, protect plant cells from a selective agent or provide resistance/tolerance to a selective agent. In one embodiment only those cells or plants that receive a functional selectable marker are capable of dividing or growing under conditions having a selective agent. The phrase "marker-positive" refers to plants that have been transformed to include a selectable marker gene.

As used herein, the term "detectable marker" refers to a label capable of detection, such as, for example, a radioisotope, fluorescent compound, bioluminescent compound, a chemiluminescent compound, metal chelator, or enzyme. Examples of detectable markers include, but are not limited to, the following: fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In an embodiment, a detectable marker can be attached by spacer arms of various lengths to reduce potential steric hindrance.

As used herein, the terms "cassette", "expression cassette" and "gene expression cassette" refer to a segment of DNA that can be inserted into a nucleic acid or polynucleotide at specific restriction sites or by homologous recombination. As used herein the segment of DNA comprises a polynucleotide that encodes a polypeptide of interest, and the cassette and restriction sites are designed to ensure insertion of the cassette in the proper reading frame for transcription and translation. In an embodiment, an expression cassette can include a polynucleotide that encodes a polypeptide of interest and having elements in addition to the polynucleotide that facilitate transformation of a particular host cell. In an embodiment, a gene expression cassette may also include elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

As used herein a "linker" or "spacer" is a bond, molecule or group of molecules that binds two separate entities to one another. Linkers and spacers may provide for optimal spacing of the two entities or may further supply a labile linkage that allows the two entities to be separated from each other. Labile linkages include photocleavable groups, acid-labile moieties, base-labile moieties and enzyme-cleavable groups. The terms "polylinker" or "multiple cloning site" as used herein defines a cluster of three or more Type-2 restriction enzyme sites located within 10 nucleotides of one another on a nucleic acid sequence. In other instances the term "polylinker" as used herein refers to a stretch of nucleotides that are targeted for joining two sequences via any known seamless cloning method (i.e., Gibson Assembly®, NEBuilder HiFiDNA Assembly®, Golden Gate Assembly, BioBrick® Assembly, etc.). Constructs comprising a polylinker are utilized for the insertion and/or excision of nucleic acid sequences such as the coding region of a gene.

As used herein, the term "control" refers to a sample used in an analytical procedure for comparison purposes. A control can be "positive" or "negative". For example, where the purpose of an analytical procedure is to detect a differentially expressed transcript or polypeptide in cells or tissue, it is generally preferable to include a positive control, such as a sample from a known plant exhibiting the desired expression, and a negative control, such as a sample from a known plant lacking the desired expression.

As used herein, the term "plant" includes a whole plant and any descendant, cell, tissue, or part of a plant. A class of plant that can be used in the present invention is generally as broad as the class of higher and lower plants amenable to mutagenesis including angiosperms (monocotyledonous and dicotyledonous plants), gymnosperms, ferns and multicellular algae. Thus, "plant" includes dicot and monocot plants. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant, comprising a protoplast and a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein.

As used herein, the term "small RNA" refers to several classes of non-coding ribonucleic acid (ncRNA). The term small RRNA describes the short chains of ncRNA produced in bacterial cells, animals, plants, and fungi. These short chains of ncRNA may be produced naturally within the cell or may be produced by the introduction of an exogenous sequence that expresses the short chain or ncRNA. The small RNA sequences do not directly code for a protein, and differ in function from other RNA in that small RNA sequences are only transcribed and not translated. The small RNA sequences are involved in other cellular functions, including gene expression and modification. Small RNA molecules are usually made up of about 20 to 30 nucleotides. The small RNA sequences may be derived from longer precursors. The precursors form structures that fold back on each other in self-complementary regions; they are then processed by the nuclease Dicer in animals or DCL1 in plants.

Many types of small RNA exist either naturally or produced artificially, including microRNAs (miRNAs), short interfering RNAs (siRNAs), antisense RNA, short hairpin RNA (shRNA), and small nucleolar RNAs (snoRNAs). Certain types of small RNA, such as microRNA and siRNA, are important in gene silencing and RNA interference (RNAi). Gene silencing is a process of genetic regulation in which a gene that would normally be expressed is "turned off" by an intracellular element, in this case, the small RNA. The protein that would normally be formed by this genetic information is not formed due to interference, and the information coded in the gene is blocked from expression.

As used herein, the term "small RNA" encompasses RNA molecules described in the literature as "tiny RNA" (Storz, (2002) Science 296:1260-3; Illangasekare et al., (1999) RNA 5:1482-1489); prokaryotic "small RNA" (sRNA) (Wassarman et al., (1999) Trends Microbiol. 7:37-45); eukaryotic "noncoding RNA (ncRNA)"; "micro-RNA (miRNA)"; "small non-mRNA (snmRNA)"; "functional RNA (fRNA)"; "transfer RNA (tRNA)"; "catalytic RNA" [e.g., ribozymes, including self-acylating ribozymes (Illangaskare et al., (1999) RNA 5:1482-1489); "small nucleolar RNAs (snoRNAs)," "tmRNA" (a.k.a. "10S RNA," Muto et al., (1998) Trends Biochem Sci. 23:25-29; and Gillet et al., (2001) Mol Microbiol. 42:879-885); RNAi molecules including without limitation "small interfering RNA (siRNA)," "endoribonuclease-prepared siRNA (e-siRNA)," "short hairpin RNA (shRNA)," and "small temporally regulated RNA (stRNA)," "diced siRNA (d-siRNA)," and aptamers, oligonucleotides and other synthetic nucleic acids that comprise at least one uracil base.

Unless otherwise specifically explained, all technical and scientific terms used herein have the same meaning as commonly understood by those of ordinary skill in the art to which this disclosure belongs. Definitions of common terms in molecular biology can be found in, for example: Lewin, Genes V, Oxford University Press, 1994 (ISBN 0-19-854287-9); Kendrew et al. (eds.), The Encyclopedia of Molecular Biology, Blackwell Science Ltd., 1994 (ISBN 0-632-02182-9); and Meyers (ed.), Molecular Biology and Biotechnology: A Comprehensive Desk Reference, VCH Publishers, Inc., 1995 (ISBN 1-56081-569-8).

III. GmTEFs1 Gene Regulatory Elements and Nucleic Acids Comprising the Same

Provided are methods and compositions for using a promoter from a *Glycine max* Glyma19g07240 (Elongation factor-1 alpha) gene to express non-GmTEFs1 transgenes in plant. In an embodiment, a promoter can be the GmTEFs1 gene promoter of SEQ ID NO:2.

In an embodiment, a polynucleotide is provided comprising a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:2. In an embodiment, a promoter is a GmTEFs1 gene promoter comprising a polynucleotide of at least 80%, 85%, 90%, 91%, 92%, 93%, 94%, 95%, 96%, 97%, 98%, 99%, 99.5%, 99.8%, or 100% identity to the polynucleotide of SEQ ID NO:2. In an embodiment, an isolated polynucleotide is provided comprising at least 80%, 85%, 90%, 91%, 92%, 93%, 94%, 95%, 96%, 97%, 98%, 99%, 99.5%, 99.8%, or 100% identity to the polynucleotide of SEQ ID NO:2. In an embodiment, a nucleic acid vector is provided comprising a GmTEFs1 promoter of SEQ ID NO:2. In an embodiment, a polynucleotide is provided comprising a GmTEFs1 promoter that is operably linked to a polylinker. In an embodiment, a gene expression cassette is provided comprising a GmTEFs1 promoter that is operably linked to a non-GmTEFs1 transgene. In an embodiment, a nucleic acid vector is provided comprising a GmTEFs1 promoter that is operably linked to a non-GmTEFs1 transgene. In one embodiment, the promoter consists of SEQ ID NO:2. In an illustrative embodiment, a nucleic acid vector comprises a GmTEFs1 promoter that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a small RNA transgene, selectable marker transgene, or combinations thereof.

In an embodiment, a nucleic acid vector comprises a gene expression cassette as disclosed herein. In an embodiment, a vector can be a plasmid, a cosmid, a bacterial artificial chromosome (BAC), a bacteriophage, a virus, or an excised polynucleotide fragment for use in direct transformation or gene targeting such as a donor DNA.

Transgene expression may also be regulated by a 5' UTR region located downstream of the promoter sequence. Both a promoter and a 5' UTR can regulate transgene/heterologous coding sequence expression. While a promoter is necessary to drive transcription, the presence of a 5' UTR can increase expression levels resulting in mRNA transcript for translation and protein synthesis. A 5' UTR gene region aids stable expression of a transgene. In a further embodiment an 5' UTR is operably linked to a GmTEFs1 promoter. In an embodiment, a 5' UTR can be the GmTEFs1 5' UTR of SEQ ID NO:3.

In an embodiment, a polynucleotide is provided comprising a 5' UTR, wherein the 5' UTR is at least 80%, 85%0, 90%, 91%, 92%, 93%, 94%, 95%, 96%, 97%, 98%, 99%, 99.5%, 99.8%, or 100% identical to SEQ ID NO:3. In an embodiment, a 5' UTR is a GmTEFs1 5' UTR comprising a polynucleotide of at least 80%, 85%, 90%, 91%, 92%, 93%, 94%, 95%, 96%, 97%, 98%, 99%, 99.5%, 99.8%, or 100% identity to the polynucleotide of SEQ ID NO:3. In an embodiment, an isolated polynucleotide is provided comprising at least 80%, 85%, 90%, 91%, 92%, 93%, 94%, 95%, 96%, 97%, 98%, 99%, 99.5%, 99.8%, or 100% identity to the polynucleotide of SEQ ID NO:3. In an embodiment, a nucleic acid vector is provided comprising GmTEFs1 5' UTR of SEQ ID NO:3. In an embodiment, a polynucleotide is provided comprising a GmTEFs1 5' UTR that is operably linked to a polylinker. In an embodiment, a gene expression cassette is provided comprising a GmTEFs1 5' UTR that is operably linked to a non-GmTEFs1 transgene. In an embodiment, a nucleic acid vector is provided comprising a GmTEFs1 5' UTR that is operably linked to a non-GmTEFs1 transgene. In one embodiment, the 5' UTR consists of SEQ ID NO:3. In an illustrative embodiment, a nucleic acid vector comprises a GmTEFs1 5' UTR that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a small RNA transgene, selectable marker transgene, or combinations thereof.

Transgene expression may also be regulated by an intron region located downstream of the promoter sequence. Both a promoter and an intron can regulate transgene/heterologous coding sequence expression. While a promoter is necessary to drive transcription, the presence of an intron can increase expression levels resulting in mRNA transcript for translation and protein synthesis. An intron gene region aids stable expression of a transgene. In a further embodiment an intron is operably linked to a GmTEFs1 promoter. In an embodiment, a intron can be the GmTEFs1 5' UTR of SEQ ID NO:28.

In an embodiment, a polynucleotide is provided comprising a intron, wherein intron is at least 80%, 85%, 90%, 91%, 92%, 93%, 94%, 95%, 96%, 97%, 98%, 99%, 99.5%, 99.8%, or 100% identical to SEQ ID NO:28. In an embodiment, a intron is a GmTEFs1 intron comprising a polynucleotide of at least 80%, 85%, 90%, 91%, 92%, 93%, 94%, 95%, 96%, 97%, 98%, 99%, 99.5%, 99.8%, or 100% identity to the polynucleotide of SEQ ID NO:28. In an embodiment, an isolated polynucleotide is provided comprising at least 80%, 85%, 90%, 91%, 92%, 93%, 94%, 95%, 96%, 97%, 98%, 99%, 99.5%, 99.8%, or 100% identity to the polynucleotide of SEQ ID NO:28. In an embodiment, a nucleic acid vector is provided comprising GmTEFs1 intron of SEQ ID NO:28. In an embodiment, a polynucleotide is provided comprising a GmTEFs1 intron that is operably linked to a polylinker. In an embodiment, a gene expression cassette is provided comprising a GmTEFs1 intron that is operably linked to a non-GmTEFs1 transgene. In an embodiment, a nucleic acid vector is provided comprising a GmTEFs1 intron that is operably linked to a non-GmTEFs1 transgene. In one embodiment, the intron consists of SEQ ID NO:28. In an illustrative embodiment, a nucleic acid vector comprises a GmTEFs1 intron that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a small RNA transgene, selectable marker transgene, or combinations thereof.

In accordance with one embodiment a nucleic acid vector is provided comprising a recombinant gene expression cassette wherein the recombinant gene expression cassette comprises a GmTEFs1 promoter operably linked to a polylinker sequence, a non-GmTEFs1 gene or non-GmTEFs1 transgene or combination thereof. In one embodiment the recombinant gene cassette comprises a GmTEFs1 promoter operably linked to a non-GmTEFs1 gene or transgene. In one embodiment the recombinant gene cassette comprises a GmTEFs1 promoter as disclosed herein is operably linked to a polylinker sequence. The polylinker is operably linked to the GmTEFs1 promoter in a manner such that insertion of a coding sequence into one of the restriction sites of the polylinker will operably link the coding sequence allowing for expression of the coding sequence when the vector is transformed or transfected into a host cell.

In accordance with one embodiment a nucleic acid vector is provided comprising a gene cassette that consists of a GmTEFs1 promoter and a non-GmTEFs1 gene. In an embodiment, the GmTEFs1 promoter of SEQ ID NO: 2 is operably linked to the 5' end of the non-GmTEFs1 gene or transgene. In a further embodiment the GmTEFs1 promoter sequence comprises SEQ ID NO:2 or a sequence that has 80, 85, 90, 95, 99 or 100% sequence identity with SEQ ID NO:2. In accordance with one embodiment a nucleic acid vector is provided comprising a gene cassette that consists of a GmTEFs1 promoter, a non-GmTEFs1 gene, wherein the GmTEFs1 promoter is operably linked to the 5' end of the non-GmTEFs1 gene, and the GmTEFs1 promoter sequence comprises SEQ ID NO:2 or a sequence that has 80, 85, 90, 95, 99 or 100% sequence identity with SEQ ID NO: 2. In a further embodiment the GmTEFs1 promoter sequence consists of SEQ ID NO: 2, or a 371 bp sequence that has 80, 85, 90, 95, or 99% sequence identity with SEQ ID NO: 2.

In accordance with one embodiment a nucleic acid vector is provided comprising a recombinant gene expression cassette wherein the recombinant gene expression cassette comprises a GmTEFs1 5' UTR operably linked to a polylinker sequence, a non-GmTEFs1 gene or transgene or combination thereof. In one embodiment the recombinant gene cassette comprises a GmTEFs1 5' UTR operably linked to a non-GmTEFs1 gene or transgene. In one embodiment the recombinant gene cassette comprises a GmTEFs1 5' UTR as disclosed herein is operably linked to a polylinker sequence. The polylinker is operably linked to the GmTEFs1 5' UTR in a manner such that insertion of a coding sequence into one of the restriction sites of the polylinker will operably link the coding sequence allowing for expression of the coding sequence when the vector is transformed or transfected into a host cell.

In accordance with one embodiment a nucleic acid vector is provided comprising a gene cassette that consists of a GmTEFs1 5' UTR and a non-GmTEFs1 gene. In an embodiment, the GmTEFs1 5' UTR of SEQ ID NO:3 is operably linked to the 5' end of the non-GmTEFs1 gene or transgene. In a further embodiment the GmTEFs1 5' UTR sequence comprises SEQ ID NO:3 or a sequence that has 80, 85, 90, 95, 99 or 100% sequence identity with SEQ ID NO:3. In accordance with one embodiment a nucleic acid vector is provided comprising a gene cassette that consists of a GmTEFs1 5' UTR, a non-GmTEFs1 gene, wherein the GmTEFs1 5' UTR is operably linked to the 5' end of the non-GmTEFs1 gene, and the GmTEFs1 gene 5' UTR sequence comprises SEQ ID NO:3 or a sequence that has 80, 85, 90, 95, 99 or 100% sequence identity with SEQ ID NO:3. In a further embodiment the GmTEFs1 gene 5' UTR sequence consists of SEQ ID NO:3, or a 248 bp sequence that has 80, 85, 90, 95, or 99% sequence identity with SEQ ID NO:3.

In accordance with one embodiment a nucleic acid vector is provided comprising a recombinant gene expression cassette wherein the recombinant gene expression cassette comprises a GmTEFs1 intron operably linked to a polylinker sequence, a non-GmTEFs1 gene or transgene or combination thereof. In one embodiment the recombinant gene cassette comprises a GmTEFs1 intron operably linked to a non-GmTEFs1 gene or transgene. In one embodiment the recombinant gene cassette comprises a GmTEFs1 intron as disclosed herein is operably linked to a polylinker sequence. The polylinker is operably linked to the GmTEFs1 intron in a manner such that insertion of a coding sequence into one of the restriction sites of the polylinker will operably link the coding sequence allowing for expression of the coding sequence when the vector is transformed or transfected into a host cell.

In accordance with one embodiment a nucleic acid vector is provided comprising a gene cassette that consists of a GmTEFs1 intron and a non-GmTEFs1 gene. In an embodiment, the GmTEFs1 intron of SEQ ID NO:28 is operably linked to the 5' end of the non-GmTEFs1 gene or transgene. In a further embodiment the GmTEFs1 intron sequence comprises SEQ ID NO:28 or a sequence that has 80, 85, 90, 95, 99 or 100% sequence identity with SEQ ID NO:28. In accordance with one embodiment a nucleic acid vector is provided comprising a gene cassette that consists of a GmTEFs1 intron, a non-GmTEFs1 gene, wherein the GmTEFs1 intron is operably linked to the 5' end of the non-GmTEFs1 gene, and the GmTEFs1 gene intron sequence comprises SEQ ID NO:28 or a sequence that has 80, 85, 90, 95, 99 or 100% sequence identity with SEQ ID NO:28. In a further embodiment the GmTEFs1 gene intron sequence consists of SEQ ID NO:28, or a 895 bp sequence that has 80, 85, 90, 95, or 99% sequence identity with SEQ ID NO:28.

A GmTEFs1 promoter may also comprise one or more additional sequence elements. In some embodiments, a GmTEFs1 promoter may comprise an exon (e.g., a leader or signal peptide such as a chloroplast transit peptide or ER retention signal). For example and without limitation, a GmTEFs1 promoter may encode an exon incorporated into the GmTEFs1 promoter as a further embodiment.

Further provided are methods and compositions for using a 3' UTR from a *Glycine max* Glyma19g07240 (Elongation factor-1 alpha) gene to terminate the expression of non-GmTEFs1 transgenes in a plant. In an embodiment, a 3' UTR terminator can be the GmTEFs1 3' UTR of SEQ ID NO:4.

In an embodiment, a polynucleotide is provided comprising a 3' UTR, wherein the 3' UTR is at least 80%, 85%, 90%, 91%, 92%, 93%, 94%, 95%, 96%, 97%, 98%, 99%, 99.5%, 99.8%, or 100% identical to SEQ ID NO:4. In an embodiment, a 3' UTR is a GmTEFs1 3' UTR comprising a polynucleotide of at least 80%, 85%, 90%, 91%, 92%, 93%, 94%, 95%, 96%, 97%, 98%, 99%, 99.5%, 99.8%, or 100% identity to the polynucleotide of SEQ ID NO:4. In an embodiment, an isolated polynucleotide is provided comprising at least 80%, 85%, 90%, 91%, 92%, 93%, 94%, 95%, 96%, 97%, 98%, 99%, 99.5%, 99.8%, or 100% identity to the polynucleotide of SEQ ID NO:4. In an embodiment, a nucleic acid vector is provided comprising a GmTEFs1 3' UTR of SEQ ID NO:4. In an embodiment, a polynucleotide is provided comprising a GmTEFs1 3' UTR that is operably linked to a polylinker. In an embodiment, a gene expression cassette is provided comprising a GmTEFs1 3' UTR that is operably linked to a non-GmTEFs1 transgene. In an embodiment, a nucleic acid vector is provided comprising a GmTEFs1 3' UTR that is operably linked to a non-GmTEFs1 transgene. In one embodiment, the 3' UTR consists of SEQ ID NO: 4. In an illustrative embodiment, a nucleic acid vector comprises a GmTEFs1 gene 3' UTR that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a small RNA transgene, selectable marker transgene, or combinations thereof.

In accordance with one embodiment a nucleic acid vector is provided comprising a recombinant gene expression cassette wherein the recombinant gene expression cassette comprises a GmTEFs1 3'UTR operably linked to a polylinker sequence, a non-GmTEFs1 gene or transgene/heterologous coding sequence or combination thereof. In one embodiment the recombinant gene cassette comprises a GmTEFs1 3'UTR operably linked to a non-GmTEFs1 gene or transgene. In one embodiment the recombinant gene cassette comprises a GmTEFs1 3'UTR as disclosed herein is operably linked to a polylinker sequence. The polylinker is operably linked to the GmTEFs1 3'UTR in a manner such that insertion of a coding sequence into one of the restriction sites of the polylinker will operably link the coding sequence allowing for expression of the coding sequence when the vector is transformed or transfected into a host cell.

In accordance with one embodiment a nucleic acid vector is provided comprising a gene cassette that consists of a GmTEFs1 3'UTR and a non-GmTEFs1 gene. In an embodiment, the GmTEFs1 3'UTR of SEQ ID NO:4 is operably linked to the 3' end of the non-GmTEFs1 gene or transgene.

In a further embodiment the GmTEFs1 3'UTR sequence comprises SEQ ID NO:4 or a sequence that has 80, 85, 90, 95, 99 or 100% sequence identity with SEQ ID NO:4. In accordance with one embodiment a nucleic acid vector is provided comprising a gene cassette that consists of a GmTEFs1 3'UTR, a non-GmTEFs1 gene, wherein the GmTEFs1 3'UTR is operably linked to the 3' end of the non-GmTEFs1 gene, and the GmTEFs1 3'UTR sequence comprises SEQ ID NO:4 or a sequence that has 80, 85, 90, 95, 99 or 100% sequence identity with SEQ ID NO:4. In a further embodiment the GmTEFs1 3'UTR sequence consists of SEQ ID NO:4, or a 739 bp sequence that has 80, 85, 90, 95, or 99% sequence identity with SEQ ID NO:4.

Further provided are methods and compositions for using a terminator from a *Glycine max* Glyma19g07240 (Elongation factor-1 alpha) gene to terminate the expression of non-GmTEFs 1 transgenes in a plant. In an embodiment, a terminator can be the GmTEFs1 terminator of SEQ ID NO:5.

In an embodiment, a polynucleotide is provided comprising a terminator, wherein the terminator is at least 80%, 85%, 90%, 91%, 92%, 93%, 94%, 95%, 96%, 97%, 98%, 99%, 99.5%, 99.8%, or 100% identical to SEQ ID NO:5. In an embodiment, a terminator is a GmTEFs1 terminator comprising a polynucleotide of at least 80%, 85%, 90%, 91%, 92%, 93%, 94%, 95%, 96%, 97%, 98%, 99%, 99.5%, 99.8%, or 100% identity to the polynucleotide of SEQ ID NO:5. In an embodiment, an isolated polynucleotide is provided comprising at least 80%, 85%, 90%, 91%, 92%, 93%, 94%, 95%, 96%, 97%, 98%, 99%, 99.5%, 99.8%, or 100% identity to the polynucleotide of SEQ ID NO:5. In an embodiment, a nucleic acid vector is provided comprising a GmTEFs1 terminator of SEQ ID NO:5. In an embodiment, a polynucleotide is provided comprising a GmTEFs1 terminator that is operably linked to a polylinker. In an embodiment, a gene expression cassette is provided comprising a GmTEFs1 terminator that is operably linked to a non-GmTEFs1 transgene. In an embodiment, a nucleic acid vector is provided comprising a GmTEFs1 terminator that is operably linked to a non-GmTEFs1 transgene. In one embodiment, the terminator consists of SEQ ID NO: 5. In an illustrative embodiment, a nucleic acid vector comprises a GmTEFs1 terminator that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a small RNA transgene, selectable marker transgene, or combinations thereof.

In accordance with one embodiment a nucleic acid vector is provided comprising a recombinant gene expression cassette wherein the recombinant gene expression cassette comprises a GmTEFs1 terminator operably linked to a polylinker sequence, a non-GmTEFs1 gene or transgene or combination thereof. In one embodiment the recombinant gene cassette comprises a GmTEFs1 terminator operably linked to a non-GmTEFs1 gene or transgene. In one embodiment the recombinant gene cassette comprises a GmTEFs1 terminator as disclosed herein is operably linked to a polylinker sequence. The polylinker is operably linked to the GmTEFs1 terminator in a manner such that insertion of a coding sequence into one of the restriction sites of the polylinker will operably link the coding sequence allowing for expression of the coding sequence when the vector is transformed or transfected into a host cell.

In accordance with one embodiment a nucleic acid vector is provided comprising a gene cassette that consists of a GmTEFs1 terminator and a non-GmTEFs1 gene. In an embodiment, the GmTEFs1 terminator of SEQ ID NO:5 is operably linked to the 3' end of the non-GmTEFs1 gene or transgene. In a further embodiment the GmTEFs1 terminator sequence comprises SEQ ID NO:5 or a sequence that has 80, 85, 90, 95, 99 or 100% sequence identity with SEQ ID NO:5. In accordance with one embodiment a nucleic acid vector is provided comprising a gene cassette that consists of a GmTEFs1 terminator, a non-GmTEFs1 gene, wherein the GmTEFs1 terminator is operably linked to the 3' end of the non-GmTEFs1 gene, and the GmTEFs1 terminator sequence comprises SEQ ID NO:5 or a sequence that has 80, 85, 90, 95, 99 or 100% sequence identity with SEQ ID NO:5. In a further embodiment the GmTEFs1 terminator sequence consists of SEQ ID NO:5, or a 897 bp sequence that has 80, 85, 90, 95, or 99% sequence identity with SEQ ID NO:5.

In one embodiment a nucleic acid construct is provided comprising a GmTEFs1 promoter and a non-GmTEFs1 gene and optionally one or more of the following elements:
a) a 5' untranslated region;
b) an intron; and
c) a 3' untranslated region,
wherein,
the GmTEFs1 promoter consists of SEQ ID NO:2 or a sequence having 95% sequence identity with SEQ ID NO:2;
the GmTEFs1 5'UTR consists of a known 5'UTR, SEQ ID NO:3 or a sequence having 95% sequence identity with SEQ ID NO:3; and
the 3' UTR consists of a known 3' UTR, SEQ ID NO:4 or a sequence having 95% sequence identity with SEQ ID NO:4; further wherein said GmTEFs1 promoter is operably linked to said transgene/heterologous coding sequence and each optional element, when present, is also operably linked to both the promoter and the transgene. In a further embodiment a transgenic cell is provided comprising the nucleic acid construct disclosed immediately above. In one embodiment the transgenic cell is a plant cell, and in a further embodiment a plant is provided wherein the plant comprises said transgenic cells.

In one embodiment a nucleic acid construct is provided comprising a GmTEFs1 promoter and a non-GmTEFs1 gene and optionally one or more of the following elements:
a) a 5' untranslated region;
b) an intron; and
c) a 3' terminator region,
wherein,
the GmTEFs1 promoter consists of SEQ ID NO:2 or a sequence having 95% sequence identity with SEQ ID NO:2;
the GmTEFs1 5'UTR consists of a known 5'UTR, SEQ ID NO:3 or a sequence having 95% sequence identity with SEQ ID NO:3; and the 3' terminator consists of a known 3' terminator, SEQ ID NO:5 or a sequence having 95% sequence identity with SEQ ID NO:5; further wherein said GmTEFs1 promoter is operably linked to said transgene/heterologous coding sequence and each optional element, when present, is also operably linked to both the promoter and the transgene. In a further embodiment a transgenic cell is provided comprising the nucleic acid construct disclosed immediately above. In one embodiment the transgenic cell is a plant cell, and in a further embodiment a plant is provided wherein the plant comprises said transgenic cells.

Another aspect of the subject disclosure comprises a functional variant which differs in one or more nucleotides from those of the nucleotide sequences comprising the regulatory element, provided herein. Such a variant is produced as the result of one or more modifications (e.g., deletion, rearrangement, or insertion) of the nucleotide sequences comprising the sequence described herein. For example, fragments and variants of the GmTEFs1 promoter sequence of SEQ ID NO: 2 may be used in a DNA construct or in a gene expression cassette to drive expression of a heterologous coding sequence. As used herein, the term "fragment" refers to a portion of the nucleic acid sequence. Fragments of GmTEFs1 promoter sequence of SEQ ID NO: 2 may retain the biological activity of initiating transcription, more particularly driving transcription in a tissue constitutively expressed manner. Alternatively, fragments of a nucleotide sequence which are useful as hybridization probes may not necessarily retain biological activity. Fragments of a nucleotide sequence for the promoter region of the GmTEFs1 promoter sequence of SEQ ID NO:2 may range from at least about 20 nucleotides, about 50 nucleotides, about 100 nucleotides, up to the full-length nucleotide sequence of the invention for the promoter region of the gene.

A biologically active portion of a GmTEFs1 promoter sequence of SEQ ID NO:2 can be prepared by isolating a portion of the GmTEFs1 promoter sequence of SEQ ID NO:2, and assessing the promoter activity of the portion. Nucleic acid molecules that are fragments of an GmTEFs1 promoter nucleotide sequence comprise at least about 16, 50, 75, 100, 150, 200, 250, 300, 350, 400, 450, 500, 550, 600, 650, 700, 800, 900, 1000, 1100, 1200, 1300, 1400, 1500, 1550, 1600, 1650, or 1700 nucleotides, or up to the number of nucleotides present in a full-length GmTEFs1 promoter sequence disclosed herein.

Variant nucleotide sequences also encompass sequences derived from a mutagenic and recombinogenic procedure such as DNA shuffling. With such a procedure, GmTEFs1 promoter nucleotide sequences of SEQ ID NO:2 can be manipulated to create a new GmTEFs1 promoter. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* i: 10747-10751; Stemmer (1994) Nature 570:389-391; Crameri et al. (1997) Nature Biotech. 75:436-438; Moore et al. (1997) J. Mol. Biol. 272:336-347; Zhang et al. (1997) Proc. Natl. Acad. Sci. USA £4:4504-4509; Crameri et al. (1998) Nature 527:288-291; and U.S. Pat. Nos. 5,605,793 and 5,837,458.

The nucleotide sequences of the subject disclosure can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire GmTEFs1 promoter sequence set forth herein or to fragments thereof are encompassed by the present invention.

In a PCR approach, oligonucleotide primers can be designed for use in PCR reactions to amplify corresponding DNA sequences from genomic DNA extracted from any plant of interest. Methods for designing PCR primers and PCR cloning are generally known in the art and are disclosed in Sambrook et al. (1989) Molecular Cloning: A Laboratory Manual (2d ed., Cold Spring Harbor Laboratory Press, Plainview, New York), hereinafter Sambrook. See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments from a chosen organism. The hybridization probes may be labeled with a detectable group such as $P^{32}$ or any other detectable marker. Thus, for example, probes for hybridization can be made by labeling synthetic oligonucleotides based on the GmTEFs1 promoter sequence of the invention. Methods for preparation of probes for hybridization and for construction of genomic libraries are generally known in the art and are disclosed in Sambrook. For example, the entire GmTEFs1 promoter sequence disclosed herein, or one or more portions thereof, may be used as a probe capable of specifically hybridizing to corresponding GmTEFs1 promoter sequences and messenger RNAs. To achieve specific hybridization under a variety of conditions, such probes include sequences that are unique among GmTEFs1 promoter sequence and are at least about 10 nucleotides in length or at least about 20 nucleotides in length. Such probes may be used to amplify corresponding GmTEFs1 promoter sequence from a chosen plant by PCR. This technique may be used to isolate additional coding sequences from a desired organism, or as a diagnostic assay to determine the presence of coding sequences in an organism. Hybridization techniques include hybridization screening of plated DNA libraries (either plaques or colonies; see, for example, Sambrook).

In accordance with one embodiment the nucleic acid vector further comprises a sequence encoding a selectable maker. In accordance with one embodiment the recombinant gene cassette is operably linked to an *Agrobacterium* T-DNA border. In accordance with one embodiment the recombinant gene cassette further comprises a first and second T-DNA border, wherein the first T-DNA border is operably linked to one end of a gene construct, and the second T-DNA border is operably linked to the other end of a gene construct. The first and second *Agrobacterium* T-DNA borders can be independently selected from T-DNA border sequences originating from bacterial strains selected from the group consisting of a nopaline synthesizing *Agrobacterium* T-DNA border, an ocotopine synthesizing *Agrobacterium* T-DNA border, a mannopine synthesizing *Agrobacterium* T-DNA border, a succinamopine synthesizing *Agrobacterium* T-DNA border, or any combination thereof. In one embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene/heterologous coding sequence operably linked to a sequence selected from SEQ ID NO:2 or a sequence having 80, 85, 90, 95, or 99% sequence identity with SEQ ID NO:2. In another embodiment, the first and second *Agrobacterium* T-DNA borders can be independently selected from T-DNA border sequences originating from bacterial strains selected from the group consisting of a nopaline synthesizing *Agrobacterium* T-DNA border, an ocotopine synthesizing *Agrobacterium* T-DNA border, a mannopine synthesizing *Agrobacterium* T-DNA border, a succinamopine synthesizing *Agrobacterium* T-DNA border, or any combination thereof. In an embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene/heterologous coding sequence operably linked to a sequence selected from SEQ ID NO:3 or a sequence having 80, 85, 90, 95, or 99% sequence identity with SEQ ID NO:3. In one embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene/heterologous coding sequence operably linked to a sequence selected from SEQ ID NO:4 or a sequence having 80, 85, 90, 95, or 99% sequence identity with SEQ ID NO:4. In one embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene/heterologous coding sequence operably linked to a sequence selected from SEQ ID NO:5 or a sequence having 80, 85, 90, 95, or 99% sequence identity with SEQ ID NO:5.

Transgenes of interest that are suitable for use in the present disclosed constructs include, but are not limited to, coding sequences that confer (1) resistance to pests or disease, (2) tolerance to herbicides, (3) value added agronomic traits, such as; yield improvement, nitrogen use efficiency, water use efficiency, and nutritional quality, (4) binding of a protein to DNA in a site specific manner, (5) expression of small RNA, and (6) selectable markers. In accordance with one embodiment, the transgene/heterologous coding sequence encodes a selectable marker or a gene product conferring insecticidal resistance, herbicide tolerance, small RNA expression, nitrogen use efficiency, water use efficiency, or nutritional quality.

1. Insect Resistance

Various insect resistance genes can be operably linked to the GmTEFs1 promoter comprising SEQ ID NO: 2, or a sequence that has 80, 85, 90, 95 or 99% sequence identity with SEQ ID NO: 2. In addition, the insect resistance genes can be operably linked to the GmTEFs1 5' UTR comprising SEQ ID NO:3, or a sequence that has 80, 85, 90, 95 or 99% sequence identity with SEQ ID NO:3. The insect resistance genes can be operably linked to the GmTEFs1 intron comprising SEQ ID NO:28, or a sequence that has 80, 85, 90, 95 or 99% sequence identity with SEQ ID NO:28. Likewise, the insect resistance genes can be operably linked to the GmTEFs1 3' UTR comprising SEQ ID NO:4, or a sequence that has 80, 85, 90, 95 or 99% sequence identity with SEQ ID NO: 4. Furthermore, the insect resistance genes can be operably linked to the GmTEFs1 terminator comprising SEQ ID NO:5, or a sequence that has 80, 85, 90, 95 or 99% sequence identity with SEQ ID NO: 5. The operably linked sequences can then be incorporated into a chosen vector to allow for identification and selection of transformed plants ("transformants"). Exemplary insect resistance coding sequences are known in the art. As embodiments of insect resistance coding sequences that can be operably linked to the regulatory elements of the subject disclosure, the following traits are provided. Coding sequences that provide exemplary Lepidopteran insect resistance include: cry1A; cry1A.105; cry1Ab; cry1Ab(truncated); cry1Ab-Ac (fusion protein); cry1Ac (marketed as Widestrike®); cry1C; cry1F (marketed as Widestrike®); cry1Fa2; cry2Ab2; cry2Ae; cry9C; mocry1F; pinII (protease inhibitor protein); vip3A (a); and vip3Aa20. Coding sequences that provide exemplary Coleopteran insect resistance include: cry34Ab1 (marketed as Herculex®); cry35Ab1 (marketed as Herculex®); cry3A; cry3Bb1; dvsnf7; and mcry3A. Coding sequences that provide exemplary multi-insect resistance include ecry31.Ab. The above list of insect resistance genes is not meant to be limiting. Any insect resistance genes are encompassed by the present disclosure.

2. Herbicide Tolerance

Various herbicide tolerance genes can be operably linked to the GmTEFs1 promoter comprising SEQ ID NO: 2, or a sequence that has 80, 85, 90, 95 or 99% sequence identity with SEQ ID NO: 2. In addition, the insect resistance genes can be operably linked to the GmTEFs1 5' UTR comprising SEQ ID NO:3, or a sequence that has 80, 85, 90, 95 or 99% sequence identity with SEQ ID NO:3. The insect resistance genes can be operably linked to the GmTEFs1 intron comprising SEQ ID NO:28, or a sequence that has 80, 85, 90, 95 or 99% sequence identity with SEQ ID NO:28. Likewise, the insect resistance genes can be operably linked to the GmTEFs1 3' UTR comprising SEQ ID NO:4, or a sequence that has 80, 85, 90, 95 or 99% sequence identity with SEQ ID NO: 4. Furthermore, the insect resistance genes can be operably linked to the GmTEFs1 terminator comprising SEQ ID NO:5, or a sequence that has 80, 85, 90, 95 or 99% sequence identity with SEQ ID NO: 5. The operably linked sequences can then be incorporated into a chosen vector to allow for identification and selection of transformed plants ("transformants"). Exemplary herbicide tolerance coding sequences are known in the art. As embodiments of herbicide tolerance coding sequences that can be operably linked to the regulatory elements of the subject disclosure, the following traits are provided. The glyphosate herbicide contains a mode of action by inhibiting the EPSPS enzyme (5-enolpyruvylshikimate-3-phosphate synthase). This enzyme is involved in the biosynthesis of aromatic amino acids that are essential for growth and development of plants. Various enzymatic mechanisms are known in the art that can be utilized to inhibit this enzyme. The genes that encode such enzymes can be operably linked to the gene regulatory elements of the subject disclosure. In an embodiment, selectable marker genes include, but are not limited to genes encoding glyphosate resistance genes include: mutant EPSPS genes such as 2mEPSPS genes, cp4 EPSPS genes, mEPSPS genes, dgt-28 genes; aroA genes; and glyphosate degradation genes such as glyphosate acetyl transferase genes (gat) and glyphosate oxidase genes (gox). These traits are currently marketed as Gly-Tol™, Optimum® GAT®, Agrisure® GT and Roundup Ready®. Resistance genes for glufosinate and/or bialaphos compounds include dsm-2, bar and pat genes. The bar and pat traits are currently marketed as LibertyLink®. Also included are tolerance genes that provide resistance to 2,4-D such as aad-1 genes (it should be noted that aad-1 genes have further activity on arloxyphenoxypropionate herbicides) and aad-12 genes (it should be noted that aad-12 genes have further activity on pyidyloxyacetate synthetic auxins). These traits are marketed as Enlist® crop protection technology. Resistance genes for ALS inhibitors (sulfonylureas, imidazolinones, triazolopyrimidines, pyrimidinylthiobenzoates, and sulfonylamino-carbonyl-triazolinones) are known in the art. These resistance genes most commonly result from point mutations to the ALS encoding gene sequence. Other ALS inhibitor resistance genes include hra genes, the csr1-2 genes, Sr-HrA genes, and surB genes. Some of the traits are marketed under the tradename Clearfield®. Herbicides that inhibit HPPD include the pyrazolones such as pyrazoxyfen, benzofenap, and topramezone; triketones such as mesotrione, sulcotrione, tembotrione, benzobicyclon; and diketonitriles such as isoxaflutole. These exemplary HPPD herbicides can be tolerated by known traits. Examples of HPPD inhibitors include hppdPF W336 genes (for resistance to isoxaflutole) and avhppd-03 genes (for resistance to meostrione). An example of oxynil herbicide tolerant traits include the bxn gene, which has been showed to impart resistance to the herbicide/antibiotic bromoxynil. Resistance genes for dicamba include the dicamba monooxygenase gene (dmo) as disclosed in International PCT Publication No. WO 2008/105890. Resistance genes for PPO or PROTOX inhibitor type herbicides (e.g., acifluorfen, butafenacil, flupropazil, pentoxazone, carfentrazone, fluazolate, pyraflufen, aclonifen, azafenidin, flumioxazin, flumiclorac, bifenox, oxyfluorfen, lactofen, fomesafen, fluoroglycofen, and sulfentrazone) are known in the art. Exemplary genes conferring resistance to PPO include over expression of a wild-type *Arabidopsis thaliana* PPO enzyme (Lermontova I and Grimm B, (2000) Overexpression of plastidic protoporphyrinogen IX oxidase leads to resistance to the diphenyl-ether herbicide acifluorfen. *Plant Physiol* 122:75-83), the *B. subtilis* PPO gene (Li, X. and Nicholl D. 2005. Development of PPO inhibitor-resistant cultures and crops. *Pest Manag. Sci.* 61:277-285 and Choi K W, Han O, Lee H J, Yun Y C, Moon Y H, Kim M K, Kuk Y I, Han S U and Guh J O, (1998) Generation of resistance to the diphenyl ether herbicide, oxyfluorfen, via expression of the *Bacillus subtilis* protoporphyrinogen oxidase gene in transgenic tobacco plants. *Biosci Biotechnol Biochem* 62:558-560.) Resistance genes for pyridinoxy or phenoxy proprionic acids and cyclohexones include the ACCase inhibitor-encoding genes (e.g., Acc1-S1, Acc1-S2 and Acc1-S3). Exemplary genes conferring resistance to cyclohexanediones and/or aryloxyphenoxypropanoic acid include haloxyfop, diclofop, fenoxyprop, fluazifop, and quizalofop. Finally, herbicides can inhibit photosynthesis, including triazine or benzonitrile are provided tolerance by psbA genes (tolerance to triazine), Is+ genes (tolerance to triazine), and nitrilase genes (tolerance to benzonitrile). The above list of herbicide tolerance genes is not meant to be limiting. Any herbicide tolerance genes are encompassed by the present disclosure.

3. Agronomic Traits

Various agronomic trait genes can be operably linked to the GmTEFs1 promoter comprising SEQ ID NO: 2, or a sequence that has 80, 85, 90, 95 or 99% sequence identity with SEQ ID NO: 2. In addition, the insect resistance genes can be operably linked to the GmTEFs1 5' UTR comprising SEQ ID NO:3, or a sequence that has 80, 85, 90, 95 or 99% sequence identity with SEQ ID NO:3. The insect resistance genes can be operably linked to the GmTEFs1 intron comprising SEQ ID NO:28, or a sequence that has 80, 85, 90, 95 or 99% sequence identity with SEQ ID NO:28. Likewise, the insect resistance genes can be operably linked to the GmTEFs1 3' UTR comprising SEQ ID NO:4, or a sequence that has 80, 85, 90, 95 or 99% sequence identity with SEQ ID NO: 4. Furthermore, the insect resistance genes can be operably linked to the GmTEFs1 terminator comprising SEQ ID NO:5, or a sequence that has 80, 85, 90, 95 or 99% sequence identity with SEQ ID NO: 5. The operably linked sequences can then be incorporated into a chosen vector to allow for identification and selection of transformed plants ("transformants"). Exemplary agronomic trait coding sequences are known in the art. As embodiments of agronomic trait coding sequences that can be operably linked to the regulatory elements of the subject disclosure, the following traits are provided. Delayed fruit softening as provided by the pg genes inhibit the production of polygalacturonase enzyme responsible for the breakdown of pectin molecules in the cell wall, and thus causes delayed softening of the fruit. Further, delayed fruit ripening/senescence of acc genes act to suppress the normal expression of the native acc synthase gene, resulting in reduced ethylene production and delayed fruit ripening. Whereas, the accd genes metabolize the precursor of the fruit ripening hormone ethylene, resulting in delayed fruit ripening. Alternatively, the sam-k genes cause delayed ripening by reducing S-adenosylmethionine (SAM), a substrate for ethylene production. Drought stress tolerance phenotypes as provided by cspB genes maintain normal cellular functions under water stress conditions by preserving RNA stability and translation. Another example includes the EcBetA genes that catalyze the production of the osmoprotectant compound glycine betaine conferring tolerance to water stress. In addition, the RmBetA genes catalyze the production of the osmoprotectant compound glycine betaine conferring tolerance to water stress. Photosynthesis and yield enhancement is provided with the bbx32 gene that expresses a protein that interacts with one or more endogenous transcription factors to regulate the plant's day/night physiological processes. Ethanol production can be increase by expression of the amy797E genes that encode a thermostable alpha-amylase enzyme that enhances bioethanol production by increasing the thermostability of amylase used in degrading starch. Finally, modified amino acid compositions can result by the expression of the cordapA genes that encode a dihydrodipicolinate synthase enzyme that increases the production of amino acid lysine. The above list of agronomic trait coding sequences is not meant to be limiting. Any agronomic trait coding sequence is encompassed by the present disclosure.

4. DNA Binding Proteins

Various DNA binding transgene/heterologous coding sequence genes/heterologous coding sequences can be operably linked to the GmTEFs1 promoter comprising SEQ ID NO: 2, or a sequence that has 80, 85, 90, 95 or 99% sequence identity with SEQ ID NO: 2. In addition, the insect resistance genes can be operably linked to the GmTEFs1 5' UTR comprising SEQ ID NO:3, or a sequence that has 80, 85, 90, 95 or 99% sequence identity with SEQ ID NO:3. The insect resistance genes can be operably linked to the GmTEFs1 intron comprising SEQ ID NO:28, or a sequence that has 80, 85, 90, 95 or 99% sequence identity with SEQ ID NO:28. Likewise, the insect resistance genes can be operably linked to the GmTEFs1 3' UTR comprising SEQ ID NO:4, or a sequence that has 80, 85, 90, 95 or 99% sequence identity with SEQ ID NO: 4. Furthermore, the insect resistance genes can be operably linked to the GmTEFs1 terminator comprising SEQ ID NO:5, or a sequence that has 80, 85, 90, 95 or 99% sequence identity with SEQ ID NO: 5. The operably linked sequences can then be incorporated into a chosen vector to allow for identification and selectable of transformed plants ("transformants"). Exemplary DNA binding protein coding sequences are known in the art. As embodiments of DNA binding protein coding sequences that can be operably linked to the regulatory elements of the subject disclosure, the following types of DNA binding proteins can include; Zinc Fingers, TALENS, CRISPRS, and meganucleases. The above list of DNA binding protein coding sequences is not meant to be limiting. Any DNA binding protein coding sequences is encompassed by the present disclosure.

5. Small RNA

Various small RNA sequences can be operably linked to the GmTEFs1 promoter comprising SEQ ID NO: 2, or a sequence that has 80, 85, 90, 95 or 99% sequence identity with SEQ ID NO: 2. In addition, the insect resistance genes can be operably linked to the GmTEFs1 5' UTR comprising SEQ ID NO:3, or a sequence that has 80, 85, 90, 95 or 99% sequence identity with SEQ ID NO:3. The insect resistance genes can be operably linked to the GmTEFs1 intron comprising SEQ ID NO:28, or a sequence that has 80, 85, 90, 95 or 99% sequence identity with SEQ ID NO:28. Likewise, the insect resistance genes can be operably linked to the GmTEFs1 3' UTR comprising SEQ ID NO:4, or a sequence that has 80, 85, 90, 95 or 99% sequence identity with SEQ ID NO: 4. Furthermore, the insect resistance genes can be operably linked to the GmTEFs1 terminator comprising SEQ ID NO:5, or a sequence that has 80, 85, 90, 95 or 99% sequence identity with SEQ ID NO: 5. The operably linked sequences can then be incorporated into a chosen vector to allow for identification and selection of transformed plants ("transformants"). Exemplary small RNA traits are known in the art. As embodiments of small RNA coding sequences that can be operably linked to the regulatory elements of the subject disclosure, the following traits are provided. For example, delayed fruit ripening/senescence of the anti-efe small RNA delays ripening by suppressing the production of ethylene via silencing of the ACO gene that encodes an ethylene-forming enzyme. The altered lignin production of ccomt small RNA reduces content of guanacyl (G) lignin by inhibition of the endogenous S-adenosyl-L-methionine: trans-caffeoyl CoA 3-O-methyltransferase (CCOMT gene). Further, the Black Spot Bruise Tolerance in Solanum verrucosum can be reduced by the Ppo5 small RNA which triggers the degradation of Ppo5 transcripts to block black spot bruise development. Also included is the dvsnf7 small RNA that inhibits Western Corn Rootworm with dsRNA containing a 240 bp fragment of the Western Corn Rootworm Snf7 gene. Modified starch/carbohydrates can result from small RNA such as the pPhL small RNA (degrades PhL transcripts to limit the formation of reducing sugars through starch degradation) and pR1 small RNA (degrades R1 transcripts to limit the formation of reducing sugars through starch degradation). Additional, benefits such as reduced acrylamide resulting from the asn1 small RNA that triggers degradation of Asn1 to impair asparagine formation and reduce polyacrylamide. Finally, the non-browning phenotype of pgas ppo suppression small RNA results in suppressing PPO to produce apples with a non-browning phenotype. The above list of small RNAs is not meant to be limiting. Any small RNA encoding sequences are encompassed by the present disclosure.

6. Selectable Markers

Various selectable markers also described as reporter genes can be operably linked to the GmTEFs1 promoter comprising SEQ ID NO: 2, or a sequence that has 80, 85, 90, 95 or 99% sequence identity with SEQ ID NO: 2. In addition, the insect resistance genes can be operably linked to the GmTEFs1 5' UTR comprising SEQ ID NO:3, or a sequence that has 80, 85, 90, 95 or 99% sequence identity with SEQ ID NO:3. The insect resistance genes can be operably linked to the GmTEFs1 intron comprising SEQ ID NO:28, or a sequence that has 80, 85, 90, 95 or 99% sequence identity with SEQ ID NO:28. Likewise, the insect resistance genes can be operably linked to the GmTEFs1 3' UTR comprising SEQ ID NO:4, or a sequence that has 80, 85, 90, 95 or 99% sequence identity with SEQ ID NO: 4. Furthermore, the insect resistance genes can be operably linked to the GmTEFs1 terminator comprising SEQ ID NO:5, or a sequence that has 80, 85, 90, 95 or 99% sequence identity with SEQ ID NO: 5. The operably linked sequences can then be incorporated into a chosen vector to allow for identification and selectable of transformed plants ("transformants"). Many methods are available to confirm expression of selectable markers in transformed plants, including for example DNA sequencing and PCR (polymerase chain reaction), Southern blotting, RNA blotting, immunological methods for detection of a protein expressed from the vector. But, usually the reporter genes are observed through visual observation of proteins that when expressed produce a colored product. Exemplary reporter genes are known in the art and encode β-glucuronidase (GUS), luciferase, green-fluorescent protein (GFP), yellow fluorescent protein (YFP, Phi-YFP), redfluorescent protein (DsRFP, RFP, etc), β-galactosidase, and the like (See Sambrook, et al., Molecular Cloning: A Laboratory Manual, Third Edition, Cold Spring Harbor Press, N.Y., 2001, the content of which is incorporated herein by reference in its entirety).

Selectable marker genes are utilized for selection of transformed cells or tissues. Selectable marker genes include genes encoding antibiotic resistance, such as those encoding neomycin phosphotransferase II (NEO), spectinomycin/streptinomycin resistance (AAD), and hygromycin phosphotransferase (HPT or HGR) as well as genes conferring resistance to herbicidal compounds. Herbicide resistance genes generally code for a modified target protein insensitive to the herbicide or for an enzyme that degrades or detoxifies the herbicide in the plant before it can act. For example, resistance to glyphosate has been obtained by using genes coding for mutant target enzymes, 5-enolpyruvylshikimate-3-phosphate synthase (EPSPS). Genes and mutants for EPSPS are well known, and further described below. Resistance to glufosinate ammonium, bromoxynil, and 2,4-dichlorophenoxyacetate (2,4-D) have been obtained by using bacterial genes encoding PAT or DSM-2, a nitrilase, an AAD-1, or an AAD-12, each of which are examples of proteins that detoxify their respective herbicides.

In an embodiment, herbicides can inhibit the growing point or meristem, including imidazolinone or sulfonylurea, and genes for resistance/tolerance of acetohydroxyacid synthase (AHAS) and acetolactate synthase (ALS) for these herbicides are well known. Glyphosate resistance genes include mutant 5-enolpyruvylshikimate-3-phosphate synthase (EPSPs) and dgt-28 genes (via the introduction of recombinant nucleic acids and/or various forms of in vivo mutagenesis of native EPSPs genes), aroA genes and glyphosate acetyl transferase (GAT) genes, respectively). Resistance genes for other phosphono compounds include bar and pat genes from *Streptomyces* species, including *Streptomyces hygroscopicus* and *Streptomyces viridichromogenes*, and pyridinoxy or phenoxy proprionic acids and cyclohexones (ACCase inhibitor-encoding genes). Exemplary genes conferring resistance to cyclohexanediones and/or aryloxyphenoxypropanoic acid (including haloxyfop, diclofop, fenoxyprop, fluazifop, quizalofop) include genes of acetyl coenzyme A carboxylase (ACCase); Acc1-S1, Acc1-S2 and Acc1-S3. In an embodiment, herbicides can inhibit photosynthesis, including triazine (psbA and 1s+ genes) or benzonitrile (nitrilase gene). Furthermore, such selectable markers can include positive selection markers such as phosphomannose isomerase (PMI) enzyme.

In an embodiment, selectable marker genes include, but are not limited to genes encoding: 2,4-D; neomycin phosphotransferase II; cyanamide hydratase; aspartate kinase; dihydrodipicolinate synthase; tryptophan decarboxylase; dihydrodipicolinate synthase and desensitized aspartate kinase; bar gene; tryptophan decarboxylase; neomycin phosphotransferase (NEO); hygromycin phosphotransferase (HPT or HYG); dihydrofolate reductase (DHFR); phosphinothricin acetyltransferase; 2,2-dichloropropionic acid dehalogenase; acetohydroxyacid synthase; 5-enolpyruvyl-shikimate-phosphate synthase (aroA); haloarylnitrilase; acetyl-coenzyme A carboxylase; dihydropteroate synthase (sul I); and 32 kD photosystem II polypeptide (psbA). An embodiment also includes selectable marker genes encoding resistance to: chloramphenicol; methotrexate; hygromycin; spectinomycin; bromoxynil; glyphosate; and phosphinothricin. The above list of selectable marker genes is not meant to be limiting. Any reporter or selectable marker gene are encompassed by the present disclosure.

In some embodiments the coding sequences are synthesized for optimal expression in a plant. For example, in an embodiment, a coding sequence of a gene has been modified by codon optimization to enhance expression in plants. An insecticidal resistance transgene, an herbicide tolerance transgene, a nitrogen use efficiency transgene, a water use efficiency transgene, a nutritional quality transgene, a DNA binding transgene, or a selectable marker transgene/heterologous coding sequence can be optimized for expression in a particular plant species or alternatively can be modified for optimal expression in dicotyledonous or monocotyledonous plants. Plant preferred codons may be determined from the codons of highest frequency in the proteins expressed in the largest amount in the particular plant species of interest. In an embodiment, a coding sequence, gene, heterologous coding sequence or transgene/heterologous coding sequence is designed to be expressed in plants at a higher level resulting in higher transformation efficiency. Methods for plant optimization of genes are well known. Guidance regarding the optimization and production of synthetic DNA sequences can be found in, for example, WO2013016546, WO2011146524, WO1997013402, U.S. Pat. Nos. 6,166, 302, and 5,380,831, herein incorporated by reference.

Transformation

Suitable methods for transformation of plants include any method by which DNA can be introduced into a cell, for example and without limitation: electroporation (see, e.g., U.S. Pat. No. 5,384,253); micro-projectile bombardment (see, e.g., U.S. Pat. Nos. 5,015,580, 5,550,318, 5,538,880, 6,160,208, 6,399,861, and 6,403,865); *Agrobacterium*-mediated transformation (see, e.g., U.S. Pat. Nos. 5,635,055, 5,824,877, 5,591,616; 5,981,840, and 6,384,301); and protoplast transformation (see, e.g., U.S. Pat. No. 5,508,184).

A DNA construct may be introduced directly into the genomic DNA of the plant cell using techniques such as agitation with silicon carbide fibers (see, e.g., U.S. Pat. Nos. 5,302,523 and 5,464,765), or the DNA constructs can be introduced directly to plant tissue using biolistic methods, such as DNA particle bombardment (see, e.g., Klein et al. (1987) *Nature* 327:70-73). Alternatively, the DNA construct can be introduced into the plant cell via nanoparticle transformation (see, e.g., US Patent Publication No. 20090104700, which is incorporated herein by reference in its entirety).

In addition, gene transfer may be achieved using non-*Agrobacterium* bacteria or viruses such as *Rhizobium* sp.

NGR234, *Sinorhizoboium meliloti, Mesorhizobium loti,* potato virus X, cauliflower mosaic virus and cassava vein mosaic virus and/or tobacco mosaic virus, See, e.g., Chung et al. (2006) *Trends Plant Sci.* 11(1):1-4.

Through the application of transformation techniques, cells of virtually any plant species may be stably transformed, and these cells may be developed into transgenic plants by well-known techniques. For example, techniques that may be particularly useful in the context of cotton transformation are described in U.S. Pat. Nos. 5,846,797, 5,159,135, 5,004,863, and 6,624,344; techniques for transforming *Brassica* plants in particular are described, for example, in U.S. Pat. No. 5,750,871; techniques for transforming soy bean are described, for example, in U.S. Pat. No. 6,384,301; and techniques for transforming *Zea mays* are described, for example, in U.S. Pat. Nos. 7,060,876 and 5,591,616, and International PCT Publication WO 95/06722.

After effecting delivery of an exogenous nucleic acid to a recipient cell, a transformed cell is generally identified for further culturing and plant regeneration. In order to improve the ability to identify transformants, one may desire to employ a selectable marker gene with the transformation vector used to generate the transformant. In an illustrative embodiment, a transformed cell population can be assayed by exposing the cells to a selective agent or agents, or the cells can be screened for the desired marker gene trait.

Cells that survive exposure to a selective agent, or cells that have been scored positive in a screening assay, may be cultured in media that supports regeneration of plants. In an embodiment, any suitable plant tissue culture media may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

Transgenic Plants

In an embodiment, a plant, plant tissue, or plant cell comprises a GmTEFs1 promoter. In one embodiment a plant, plant tissue, or plant cell comprises the GmTEFs1 promoter of a sequence selected from SEQ ID NO:2 or a sequence that has 80%, 85%, 90%, 95% or 99.5% sequence identity with a sequence selected from SEQ ID NO:2. In an embodiment, a plant, plant tissue, or plant cell comprises a gene expression cassette comprising a sequence selected from SEQ ID NO:2, or a sequence that has 80%, 85%, 90%, 95% or 99.5% sequence identity with a sequence selected from SEQ ID NO:2 that is operably linked to a non-GmTEFs1 gene. In an illustrative embodiment, a plant, plant tissue, or plant cell comprises a gene expression cassette comprising a GmTEFs1 promoter that is operably linked to a transgene or heterologous coding sequence, wherein the transgene or heterologous coding sequence can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In accordance with one embodiment a plant, plant tissue, or plant cell is provided wherein the plant, plant tissue, or plant cell comprises a GmTEFs1 promoter derived sequence operably linked to a transgene, wherein the GmTEFs1 promoter derived sequence comprises a sequence SEQ ID NO:2 or a sequence having 80%, 85%, 90%, 95% or 99.5% sequence identity with SEQ ID NO:2. In one embodiment a plant, plant tissue, or plant cell is provided wherein the plant, plant tissue, or plant cell comprises SEQ ID NO:2, or a sequence that has 80%, 85%, 90%, 95% or 99.5% sequence identity with SEQ ID NO:2 operably linked to a non-GmTEFs1 gene. In one embodiment the plant, plant tissue, or plant cell is a dicotyledonous or monocotyledonous plant or a cell or tissue derived from a dicotyledonous or monocotyledonous plant. In one embodiment the plant is selected from the group consisting of *Zea mays*, wheat, rice, sorghum, oats, rye, bananas, sugar cane, soybean, cotton, sunflower, and canola. In one embodiment the plant is *Zea mays*. In another embodiment the plant is soybean (e.g., *Glycine max*). In accordance with one embodiment the plant, plant tissue, or plant cell comprises SEQ ID NO: 2 or a sequence having 80%, 85%, 90%, 95% or 99.5% sequence identity with SEQ ID NO:2 operably linked to a non-GmTEFs1 gene. In one embodiment the plant, plant tissue, or plant cell comprises a promoter operably linked to a transgene/heterologous coding sequence wherein the promoter consists of SEQ ID NO:2 or a sequence having 80%, 85%, 90%, 95% or 99.5% sequence identity with SEQ ID NO:2. In accordance with one embodiment the gene construct comprising GmTEFs1 promoter sequence operably linked to a transgene/heterologous coding sequence is incorporated into the genome of the plant, plant tissue, or plant cell.

In an embodiment, a plant, plant tissue, or plant cell comprises a GmTEFs1 5' UTR. In one embodiment a plant, plant tissue, or plant cell comprises the GmTEFs1 5' UTR of a sequence selected from SEQ ID NO:3 or a sequence that has 80%, 85%, 90%, 95% or 99.5% sequence identity with a sequence selected from SEQ ID NO:3. In an embodiment, a plant, plant tissue, or plant cell comprises a gene expression cassette comprising a sequence selected from SEQ ID NO:3, or a sequence that has 80%, 85%, 90%, 95% or 99.5% sequence identity with a sequence selected from SEQ ID NO:3 that is operably linked to a non-GmTEFs1 gene. In an illustrative embodiment, a plant, plant tissue, or plant cell comprises a gene expression cassette comprising a GmTEFs1 5' UTR that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In accordance with one embodiment a plant, plant tissue, or plant cell is provided wherein the plant, plant tissue, or plant cell comprises a GmTEFs1 5' UTR derived sequence operably linked to a transgene, wherein the GmTEFs1 5' UTR derived sequence comprises a sequence SEQ ID NO:3 or a sequence having 80%, 85%, 90%, 95% or 99.5% sequence identity with SEQ ID NO:3. In one embodiment a plant, plant tissue, or plant cell is provided wherein the plant, plant tissue, or plant cell comprises SEQ ID NO:3, or a sequence that has 80%, 85%, 90%, 95% or 99.5% sequence identity with SEQ ID NO:3 operably linked to a non-GmTEFs1 gene. In one embodiment the plant, plant tissue, or plant cell is a dicotyledonous or monocotyledonous plant or a cell or tissue derived from a dicotyledonous or monocotyledonous plant. In one embodiment the plant is selected from the group consisting of *Zea mays*, wheat, rice, sorghum, oats, rye, bananas, sugar cane, soybean, cotton, sunflower, and canola. In one embodiment the plant is *Zea mays*. In another embodiment the plant is soybean (e.g., *Glycine max*). In accordance with one embodiment the plant, plant tissue, or plant cell comprises SEQ ID NO:3 or a sequence having 80%, 85%, 90%, 95% or 99.5% sequence identity with SEQ ID NO:3 operably linked to a non-GmTEFs1 gene. In one embodiment the plant, plant tissue, or plant cell comprises a 5' UTR operably linked to a transgene/heterologous coding sequence wherein the 5' UTR consists of SEQ ID NO:3 or a sequence having 80%, 85%, 90%, 95% or 99.5% sequence identity with SEQ ID NO:3. In accordance with one embodiment the gene construct comprising GmTEFs1 5' UTR sequence operably linked to a transgene/heterologous coding sequence is incorporated into the genome of the plant, plant tissue, or plant cell.

In an embodiment, a plant, plant tissue, or plant cell comprises a GmTEFs1 intron. In one embodiment a plant, plant tissue, or plant cell comprises the GmTEFs1 intron of a sequence selected from SEQ ID NO:28 or a sequence that has 80%, 85%, 90%, 95% or 99.5% sequence identity with a sequence selected from SEQ ID NO:28. In an embodiment, a plant, plant tissue, or plant cell comprises a gene expression cassette comprising a sequence selected from SEQ ID NO:28, or a sequence that has 80%, 85%, 90%, 95% or 99.5% sequence identity with a sequence selected from SEQ ID NO:28 that is operably linked to a non-GmTEFs1 gene. In an illustrative embodiment, a plant, plant tissue, or plant cell comprises a gene expression cassette comprising a GmTEFs1 intron that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In accordance with one embodiment a plant, plant tissue, or plant cell is provided wherein the plant, plant tissue, or plant cell comprises a GmTEFs1 intron derived sequence operably linked to a transgene, wherein the GmTEFs1 intron derived sequence comprises a sequence SEQ ID NO:28 or a sequence having 80%, 85%, 90%, 95% or 99.5% sequence identity with SEQ ID NO:28. In one embodiment a plant, plant tissue, or plant cell is provided wherein the plant, plant tissue, or plant cell comprises SEQ ID NO:28, or a sequence that has 80%, 85%, 90%, 95% or 99.5% sequence identity with SEQ ID NO:28 operably linked to a non-GmTEFs1 gene. In one embodiment the plant, plant tissue, or plant cell is a dicotyledonous or monocotyledonous plant or a cell or tissue derived from a dicotyledonous or monocotyledonous plant. In one embodiment the plant is selected from the group consisting of *Zea mays*, wheat, rice, sorghum, oats, rye, bananas, sugar cane, soybean, cotton, sunflower, and canola. In one embodiment the plant is *Zea mays*. In another embodiment the plant is soybean (e.g, *Glycine max*). In accordance with one embodiment the plant, plant tissue, or plant cell comprises SEQ ID NO:28 or a sequence having 80%, 85%, 90%, 95% or 99.5% sequence identity with SEQ ID NO:28 operably linked to a non-GmTEFs1 gene. In one embodiment the plant, plant tissue, or plant cell comprises a intron operably linked to a transgene/heterologous coding sequence wherein the intron consists of SEQ ID NO:28 or a sequence having 80%, 85%, 90%, 95% or 99.5% sequence identity with SEQ ID NO:28. In accordance with one embodiment the gene construct comprising GmTEFs1 intron sequence operably linked to a transgene/heterologous coding sequence is incorporated into the genome of the plant, plant tissue, or plant cell.

In an embodiment, a plant, plant tissue, or plant cell comprises a GmTEFs1 3' UTR. In one embodiment a plant, plant tissue, or plant cell comprises the GmTEFs1 3' UTR of a sequence selected from SEQ ID NO:4 or a sequence that has 80%, 85%, 90%, 95% or 99.5% sequence identity with a sequence selected from SEQ ID NO:4. In an embodiment, a plant, plant tissue, or plant cell comprises a gene expression cassette comprising a sequence selected from SEQ ID NO:4, or a sequence that has 80%, 85%, 90%, 95% or 99.5% sequence identity with a sequence selected from SEQ ID NO:4 that is operably linked to a non-GmTEFs1 gene. In an illustrative embodiment, a plant, plant tissue, or plant cell comprises a gene expression cassette comprising a GmTEFs1 3' UTR that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In accordance with one embodiment a plant, plant tissue, or plant cell is provided wherein the plant, plant tissue, or plant cell comprises a GmTEFs1 3' UTR derived sequence operably linked to a transgene, wherein the GmTEFs1 3' UTR derived sequence comprises a sequence SEQ ID NO:4 or a sequence having 80%, 85%, 90%, 95% or 99.5% sequence identity with SEQ ID NO:4. In one embodiment a plant, plant tissue, or plant cell is provided wherein the plant, plant tissue, or plant cell comprises SEQ ID NO:4, or a sequence that has 80%, 85%, 90%, 95% or 99.5% sequence identity with SEQ ID NO:4 operably linked to a non-GmTEFs1 gene. In one embodiment the plant, plant tissue, or plant cell is a dicotyledonous or monocotyledonous plant or a cell or tissue derived from a dicotyledonous or monocotyledonous plant. In one embodiment the plant is selected from the group consisting of *Zea mays*, wheat, rice, sorghum, oats, rye, bananas, sugar cane, soybean, cotton, sunflower, and canola. In one embodiment the plant is *Zea mays*. In another embodiment the plant is soybean (e.g, *Glycine max*). In accordance with one embodiment the plant, plant tissue, or plant cell comprises SEQ ID NO:4 or a sequence having 80%, 85%, 90%, 95% or 99.5% sequence identity with SEQ ID NO:4 operably linked to a non-GmTEFs1 gene. In one embodiment the plant, plant tissue, or plant cell comprises a 3' UTR operably linked to a transgene/heterologous coding sequence wherein the 3' UTR consists of SEQ ID NO:4 or a sequence having 80%, 85%, 90%, 95% or 99.5% sequence identity with SEQ ID NO:4. In accordance with one embodiment the gene construct comprising GmTEFs1 gene 3' UTR sequence operably linked to a transgene/heterologous coding sequence is incorporated into the genome of the plant, plant tissue, or plant cell.

In an embodiment, a plant, plant tissue, or plant cell comprises a GmTEFs1 terminator. In one embodiment a plant, plant tissue, or plant cell comprises the GmTEFs1 terminator of a sequence selected from SEQ ID NO:5 or a sequence that has 80%, 85%, 90%, 95% or 99.5% sequence identity with a sequence selected from SEQ ID NO:5. In an embodiment, a plant, plant tissue, or plant cell comprises a gene expression cassette comprising a sequence selected from SEQ ID NO:5, or a sequence that has 80%, 85%, 90%, 95% or 99.5% sequence identity with a sequence selected from SEQ ID NO:5 that is operably linked to a non-GmTEFs1 gene. In an illustrative embodiment, a plant, plant tissue, or plant cell comprises a gene expression cassette comprising a GmTEFs1 terminator that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In accordance with one embodiment a plant, plant tissue, or plant cell is provided wherein the plant, plant tissue, or plant cell comprises a GmTEFs1 terminator derived sequence operably linked to a transgene, wherein the GmTEFs1 terminator derived sequence comprises a sequence SEQ ID NO:5 or a sequence having 80%, 85%, 90%, 95% or 99.5% sequence identity with SEQ ID NO:5. In one embodiment a plant, plant tissue, or plant cell is provided wherein the plant, plant tissue, or plant cell comprises SEQ ID NO:5, or a sequence that has 80%, 85%, 90%, 95% or 99.5% sequence identity with SEQ ID NO:5 operably linked to a non-GmTEFs1 gene. In one embodiment the plant, plant tissue, or plant cell is a dicotyledonous or monocotyledonous plant or a cell or tissue derived from a dicotyledonous or monocotyledonous plant. In one embodiment the plant is selected from the group consisting of *Zea mays*, wheat, rice, sorghum, oats, rye, bananas, sugar cane, soybean, cotton, sunflower, and canola. In one embodiment the plant is *Zea mays*. In another embodiment the plant is soybean (e.g., *Glycine max*). In accordance with one embodiment the plant, plant tissue, or plant cell comprises SEQ ID NO:5 or a sequence having 80%, 85%, 90%, 95% or 99.5% sequence identity with SEQ ID NO:5 operably linked to a non-GmTEFs1 gene. In one embodiment the plant, plant tissue, or plant cell comprises a terminator operably linked to a transgene/heterologous coding sequence wherein the terminator consists of SEQ ID NO:5 or a sequence having 80%, 85%, 90%, 95% or 99.5% sequence identity with SEQ ID NO:5. In accordance with one embodiment the gene construct comprising GmTEFs1 gene terminator sequence operably linked to a transgene/heterologous coding sequence is incorporated into the genome of the plant, plant tissue, or plant cell.

In an embodiment, a plant, plant tissue, or plant cell according to the methods disclosed herein can be a dicotyledonous plant. The dicotyledonous plant, plant tissue, or plant cell can be, but not limited to alfalfa, rapeseed, canola, Indian mustard, Ethiopian mustard, soybean, sunflower, cotton, beans, broccoli, cabbage, cauliflower, celery, cucumber, eggplant, lettuce; melon, pea, pepper, peanut, potato, pumpkin, radish, spinach, sugarbeet, sunflower, tobacco, tomato, and watermelon.

One of skill in the art will recognize that after the exogenous sequence is stably incorporated in transgenic plants and confirmed to be operable, it can be introduced into other plants by sexual crossing. Any of a number of standard breeding techniques can be used, depending upon the species to be crossed.

The present disclosure also encompasses seeds of the transgenic plants described above, wherein the seed has the transgene/heterologous coding sequence or gene construct containing the gene regulatory elements of the subject disclosure. The present disclosure further encompasses the progeny, clones, cell lines or cells of the transgenic plants described above wherein said progeny, clone, cell line or cell has the transgene/heterologous coding sequence or gene construct containing the gene regulatory elements of the subject disclosure.

The present disclosure also encompasses the cultivation of transgenic plants described above, wherein the transgenic plant has the transgene/heterologous coding sequence or gene construct containing the gene regulatory elements of the subject disclosure. Accordingly, such transgenic plants may be engineered to, inter alia, have one or more desired traits or transgenic events containing the gene regulatory elements of the subject disclosure, by being transformed with nucleic acid molecules according to the invention, and may be cropped or cultivated by any method known to those of skill in the art.

Method of Expressing a Transgene

In an embodiment, a method of expressing at least one transgene/heterologous coding sequence in a plant comprises growing a plant comprising a GmTEFs1 promoter operably linked to at least one transgene/heterologous coding sequence or a polylinker sequence. In an embodiment the GmTEFs1 promoter consists of a sequence selected from SEQ ID NO:2 or a sequence that has 80%, 85%, 90%, 95% or 99.5% sequence identity with a sequence selected from SEQ ID NO:2. In an embodiment, a method of expressing at least one transgene/heterologous coding sequence in a plant comprising growing a plant comprising a GmTEFs1 promoter operably linked to at least one transgene. In an embodiment, a method of expressing at least one transgene/heterologous coding sequence in a plant tissue or plant cell comprising culturing a plant tissue or plant cell comprising a GmTEFs1 promoter operably linked to at least one transgene.

In an embodiment, a method of expressing at least one transgene/heterologous coding sequence in a plant comprises growing a plant comprising a gene expression cassette comprising a GmTEFs1 promoter operably linked to at least one transgene. In one embodiment the GmTEFs1 promoter consists of a sequence selected from SEQ ID NO:2 or a sequence that has 80%, 85%, 90%, 95% or 99.5% sequence identity with a sequence selected from SEQ ID NO:2. In an embodiment, a method of expressing at least one transgene/heterologous coding sequence in a plant comprises growing a plant comprising a gene expression cassette comprising a GmTEFs1 promoter operably linked to at least one transgene. In an embodiment, a method of expressing at least one transgene/heterologous coding sequence in a plant comprises growing a plant comprising a gene expression cassette comprising a GmTEFs1 promoter operably linked to at least one transgene. In an embodiment, a method of expressing at least one transgene/heterologous coding sequence in a plant tissue or plant cell comprises culturing a plant tissue or plant cell comprising a gene expression cassette containing a GmTEFs1 promoter operably linked to at least one transgene. In an embodiment, a method of expressing at least one transgene/heterologous coding sequence in a plant tissue or plant cell comprises culturing a plant tissue or plant cell comprising a gene expression cassette, a GmTEFs1 promoter operably linked to at least one transgene.

In an embodiment, a method of expressing at least one transgene/heterologous coding sequence in a plant comprises growing a plant comprising a GmTEFs1 5' UTR operably linked to at least one transgene/heterologous coding sequence or a polylinker sequence. In an embodiment the GmTEFs1 5' UTR consists of a sequence selected from SEQ ID NO:3 or a sequence that has 80%, 85%, 90%, 95% or 99.5% sequence identity with a sequence selected from SEQ ID NO:3. In an embodiment, a method of expressing at least one transgene/heterologous coding sequence in a plant comprising growing a plant comprising a GmTEFs1 5' UTR operably linked to at least one transgene. In an embodiment, a method of expressing at least one transgene/heterologous coding sequence in a plant tissue or plant cell comprising culturing a plant tissue or plant cell comprising a GmTEFs1 5' UTR operably linked to at least one transgene.

In an embodiment, a method of expressing at least one transgene/heterologous coding sequence in a plant comprises growing a plant comprising a gene expression cassette comprising a GmTEFs1 5' UTR operably linked to at least one transgene. In one embodiment the GmTEFs1 5' UTR consists of a sequence selected from SEQ ID NO:3 or a sequence that has 80%, 85%, 90%, 95% or 99.5% sequence identity with a sequence selected from SEQ ID NO:3. In an embodiment, a method of expressing at least one transgene/ heterologous coding sequence in a plant comprises growing a plant comprising a gene expression cassette comprising a GmTEFs1 5' UTR operably linked to at least one transgene. In an embodiment, a method of expressing at least one transgene/heterologous coding sequence in a plant comprises growing a plant comprising a gene expression cassette comprising a GmTEFs1 5' UTR operably linked to at least one transgene. In an embodiment, a method of expressing at least one transgene/heterologous coding sequence in a plant tissue or plant cell comprises culturing a plant tissue or plant cell comprising a gene expression cassette containing a GmTEFs1 5' UTR operably linked to at least one transgene. In an embodiment, a method of expressing at least one transgene/heterologous coding sequence in a plant tissue or plant cell comprises culturing a plant tissue or plant cell comprising a gene expression cassette, a GmTEFs1 5' UTR operably linked to at least one transgene.

In an embodiment, a method of expressing at least one transgene/heterologous coding sequence in a plant comprises growing a plant comprising a GmTEFs1 intron operably linked to at least one transgene/heterologous coding sequence or a polylinker sequence. In an embodiment the GmTEFs1 intron consists of a sequence selected from SEQ ID NO:28 or a sequence that has 80%, 85%, 90%, 95% or 99.5% sequence identity with a sequence selected from SEQ ID NO:28. In an embodiment, a method of expressing at least one transgene/heterologous coding sequence in a plant comprising growing a plant comprising a GmTEFs1 intron operably linked to at least one transgene. In an embodiment, a method of expressing at least one transgene/heterologous coding sequence in a plant tissue or plant cell comprising culturing a plant tissue or plant cell comprising a GmTEFs1 intron operably linked to at least one transgene.

In an embodiment, a method of expressing at least one transgene/heterologous coding sequence in a plant comprises growing a plant comprising a gene expression cassette comprising a GmTEFs1 intron operably linked to at least one transgene. In one embodiment the GmTEFs1 intron consists of a sequence selected from SEQ ID NO:28 or a sequence that has 80%, 85%, 90%, 95% or 99.5% sequence identity with a sequence selected from SEQ ID NO:28. In an embodiment, a method of expressing at least one transgene/ heterologous coding sequence in a plant comprises growing a plant comprising a gene expression cassette comprising a GmTEFs1 intron operably linked to at least one transgene. In an embodiment, a method of expressing at least one transgene/heterologous coding sequence in a plant comprises growing a plant comprising a gene expression cassette comprising a GmTEFs1 intron operably linked to at least one transgene. In an embodiment, a method of expressing at least one transgene/heterologous coding sequence in a plant tissue or plant cell comprises culturing a plant tissue or plant cell comprising a gene expression cassette containing a GmTEFs1 intron operably linked to at least one transgene.

In an embodiment, a method of expressing at least one transgene/heterologous coding sequence in a plant tissue or plant cell comprises culturing a plant tissue or plant cell comprising a gene expression cassette, a GmTEFs1 intron operably linked to at least one transgene.

In an embodiment, a method of expressing at least one transgene/heterologous coding sequence in a plant comprises growing a plant comprising a GmTEFs1 3' UTR operably linked to at least one transgene/heterologous coding sequence or a polylinker sequence. In an embodiment the GmTEFs1 3' UTR consists of a sequence selected from SEQ ID NO:4 or a sequence that has 80%, 85%, 90%, 95% or 99.5% sequence identity with a sequence selected from SEQ ID NO:4. In an embodiment, a method of expressing at least one transgene/heterologous coding sequence in a plant comprising growing a plant comprising a GmTEFs1 3' UTR operably linked to at least one transgene. In an embodiment, a method of expressing at least one transgene/heterologous coding sequence in a plant tissue or plant cell comprising culturing a plant tissue or plant cell comprising a GmTEFs1 3' UTR operably linked to at least one transgene.

In an embodiment, a method of expressing at least one transgene/heterologous coding sequence in a plant comprises growing a plant comprising a gene expression cassette comprising a GmTEFs1 3' UTR operably linked to at least one transgene. In one embodiment the GmTEFs1 3' UTR consists of a sequence selected from SEQ ID NO:4 or a sequence that has 80%, 85%, 90%, 95% or 99.5% sequence identity with a sequence selected from SEQ ID NO:4. In an embodiment, a method of expressing at least one transgene/ heterologous coding sequence in a plant comprises growing a plant comprising a gene expression cassette comprising a GmTEFs1 3' UTR operably linked to at least one transgene. In an embodiment, a method of expressing at least one transgene/heterologous coding sequence in a plant comprises growing a plant comprising a gene expression cassette comprising a GmTEFs1 3' UTR operably linked to at least one transgene. In an embodiment, a method of expressing at least one transgene/heterologous coding sequence in a plant tissue or plant cell comprises culturing a plant tissue or plant cell comprising a gene expression cassette containing a GmTEFs1 3' UTR operably linked to at least one transgene. In an embodiment, a method of expressing at least one transgene/heterologous coding sequence in a plant tissue or plant cell comprises culturing a plant tissue or plant cell comprising a gene expression cassette, a GmTEFs1 3' UTR operably linked to at least one transgene.

In an embodiment, a method of expressing at least one transgene/heterologous coding sequence in a plant comprises growing a plant comprising a GmTEFs1 terminator operably linked to at least one transgene/heterologous coding sequence or a polylinker sequence. In an embodiment the GmTEFs1 terminator consists of a sequence selected from SEQ ID NO:5 or a sequence that has 80%, 85%, 90%, 95% or 99.5% sequence identity with a sequence selected from SEQ ID NO:5. In an embodiment, a method of expressing at least one transgene/heterologous coding sequence in a plant comprising growing a plant comprising a GmTEFs1 terminator operably linked to at least one transgene. In an embodiment, a method of expressing at least one transgene/heterologous coding sequence in a plant tissue or plant cell comprises culturing a plant tissue or plant cell comprising a GmTEFs1 terminator operably linked to at least one transgene.

In an embodiment, a method of expressing at least one transgene/heterologous coding sequence in a plant comprises growing a plant comprising a gene expression cassette comprising a GmTEFs1 terminator operably linked to at least one transgene. In one embodiment the GmTEFs1 terminator consists of a sequence selected from SEQ ID NO:5 or a sequence that has 80%, 85%, 90%, 95% or 99.5% sequence identity with a sequence selected from SEQ ID NO:5. In an embodiment, a method of expressing at least one transgene/heterologous coding sequence in a plant comprises growing a plant comprising a gene expression cassette comprising a GmTEFs1 terminator operably linked to at least one transgene. In an embodiment, a method of expressing at least one transgene/heterologous coding sequence in a plant comprises growing a plant comprising a gene expression cassette comprising a GmTEFs1 terminator operably linked to at least one transgene. In an embodiment, a method of expressing at least one transgene/heterologous coding sequence in a plant tissue or plant cell comprises culturing a plant tissue or plant cell comprising a gene expression cassette containing a GmTEFs1 terminator operably linked to at least one transgene. In an embodiment, a method of expressing at least one transgene/heterologous coding sequence in a plant tissue or plant cell comprises culturing a plant tissue or plant cell comprising a gene expression cassette, a GmTEFs1 terminator operably linked to at least one transgene.

The following examples are provided to illustrate certain particular features and/or embodiments. The examples should not be construed to limit the disclosure to the particular features or embodiments exemplified.

EXAMPLES

Example 1: Identification of Regulatory Elements from Soybean Genomic Sequences The expression profiles of total mRNA expression for 25 soybean tissues (var. Williams 82) were obtained via Next Generation Sequencing (NGS) and were used to identify candidate soybean genes for sourcing regulatory elements. The tissues included were collected from young seedlings (expanded cotyledons, roots, and hypocotyls), V5 (leaves and stems), and R5 (leaves, flowers, different stages of seed and pod development) soybean plants. Soybean endogenous genes that exhibited the desired expression profile were identified as potential candidates for sourcing regulatory sequences.

One of the genes with the desired expression pattern was Glyma19g07240 that was expressed ubiquitously. This gene was identified as GmTEFs1 gene encoding translation Elongation factor-1 alpha (UniProtKB-O04299_SOYBN) (Apweiler, Rolf, et al. "UniProt: the universal protein knowledgebase." *Nucleic acids research* 32.suppl_1 (2004): D115-D119; available at http://www.uniprot.org/), thus this gene was described as "GmTEFs1". Regulatory sequences from the GmTEFs1 gene were isolated and characterized for the ability to drive transgene expression. The promoter of the GmTEFs1 is provided herein as SEQ ID NO:2.

The regulatory sequences of the Glyma19g07240 gene (GmTEFs1) were defined as ~1.4 kb sequence upstream of ATG of the Glyma19g07240 gene for the promoter and 5' untranslated leader (UTR), and ~0.6 kb downstream of the Glyma19g07240 gene stop codon for the 3' UTR and terminator. To further refine the regulatory sequences additional analyses of the regulatory elements were completed. Putative upstream and downstream regulatory sequences were assessed for the presence of transposable sequences, repressive DNA (methylation) and chromatin (histone-H3-lysine-4-dimethylation, commonly abbreviated as H3K4me2) marks using methods as previously disclosed in U.S. Patent Publication No. 20150128309A1, herein incorporated by reference in its entirety. The Glyma19g07240 gene DNA sequences containing the repressive DNA and chromatin marks were excluded from the sourced upstream and downstream regulatory sequence. Long stretches (100 bp or more) of AT-rich sequences (>75% AT rich) within the 5' and 3' sequences were also avoided as means to reduce difficulties with de novo synthesis of the DNA fragments.

The resulting GmTEFs1 upstream regulatory sequence contained both a promoter (SEQ ID NO:2) and 5' UTR (SEQ ID NO:3) that contains an 895 bp intron (SEQ ID NO:28). The downstream sequences encompassed a 3' UTR (SEQ ID NO:4) and a terminator (SEQ ID NO:4) of the GmTEFs1 gene. The terminator sequences extended for ~100-200 bp beyond the last known poly-adenylation site. Two guanine base pair were deleted from the candidate GmTEFs1 terminator (SEQ ID NO:5) to remove undesirable restriction sites.

Sequences of the sourced from soybean genome the GmTEFs1 (Glyma19g07240) gene promoter/5'UTR and terminator are provided herein.

Example 2: Cloning of the Regulatory Sequences from Soybean

The promoter, 5' UTR and 3' UTR/terminator sequences of the GmTEFs1 gene were synthesized by DNA2.0. A diagram of the synthetic fragment is shown in FIG. 1. A linker containing multiple cloning site was included between the promoter/5' UTR with the intron and the 3' UTR/terminator sequence.

The synthetic GmTEFs1 fragment (promoter/5'UTR and terminator) was cloned in a Gateway entry vector, and the RFP/AAD12 reporter gene (SEQ ID NO:10) was inserted between the 5'UTR and the terminator. The reporter gene was the dual reporter encoding a translational fusion protein containing the RFP and AAD12 polypeptides joined with the rigid helical peptide linker, LAE(EAAAK)$_5$AAA described by Arai et al, (2001), *Protein Eng*, 14, 529-532 and Marqusee et al, (1987), Proc Natl Acad Sci USA, 84, 8898-8902. The resulting expression cassette (SEQ ID NO:11) was moved to a binary vector and labeled as pDAB122124. This binary vector also contained the Green Fluorescent Protein (GFP) gene driven by the *Arabidopsis* Ubiquitin3 promoter and 5' UTR (AtUbi3) and terminated by the *Arabidopsis* Ubiquitin 3 terminator (AtUbi3). Likewise, the binary vector contained the synthetic phosphinothricin N-acetyltransferase gene from *Streptomyces viridochromogenes* (PAT) was driven by the Cassava vein mosaic virus promoter (CsVMV) and terminated by the *Agrobacterium tumefaciens* Orf1 terminator (AtuOrf1). The GFP and PAT gene expression cassettes are provided as SEQ ID NO:12.

Cloning steps for the GmAct7-2 and GmGAPC1 regulatory sequences were similar to those described above for GmTEFs1. The GmAct7-2 was tested in the pDAB122133 construct and GmGAPC1 was tested in the pDAB122134 construct.

Example 3: *N. benthamiana* Leaf Infiltrations and Transient Assays of GmTEFs1, GmAct7-2 and GmGAPC1 Driven Expression of the RFP/AAD12 Reporter Next, *N. benthamiana* plants were grown in the greenhouse under a 16 hour photoperiod, 27° C./24° C. The 20-24 day old plants were used for transient expression assays. For this, the top 3-4 leaves were infiltrated using a mix of two modified *Agrobacterium tumefaciens* strains. The first strain was used in all infiltrations and carried the pDAB112236 construct containing transgene that expressed the P19 silencing suppressor (Voinnet et al, (1999), Proc Natl Acad Sci U.S.A., 96, 14147-14152). The second *Agrobacterium* strain was either the experimental strain carrying a test construct (with the GmTEFs1, GmAct7-2, or GmGAPC1 regulatory elements), or a benchmark control construct (Table 1). Two benchmark constructs that were used contained the RFP/AAD12 reporter gene under the control of *Arabidopsis thaliana* Ubiquitin 14 promoter::*Arabidopsis thaliana* Ubiquitin 14 terminator (AtUbi14/AtUbi14) and the *Arabidopsis thaliana* Ubiquitin 10 promoter::*Agrobacterium tumefaciens* Orf23 (AtUbi10 AtuOrf23). The mixing ratios were based on Optical Density (OD) readings. The density of all *Agrobacterium* cultures was adjusted to OD 2.0. After infiltration, plants were grown to a Conviron™ until the infiltrated leaves were collected on the fifth day after infiltration. Fluorescence data for the reporter genes was collected using a Typhoon™ scanner from 25-30 individual 1.5 cm leaf disks for each construct.

All samples from *N. benthamiana* were scanned on three channels; chlorophyll (488 nm blue laser, 670 nm BP30, 580 nm split), GFP (488 nm blue laser, 520 nm BP40, 580 nm split), and RFP (532 nm green laser, 580 nm BP30). The photomultiplier voltage (PMT) setting used for *N. benthamiana* was 340 for chlorophyll, 340 for GFP and 360 for RFP.

functional and can be used to drive expression of a heterologous transgene in *N. benthamiana* leaf transient assays.

In contrast, to the GmTEFs1 regulatory sequences which drove significantly higher than background mean RFP/AAD12 fluorescence expression, the GmAct2-2 and GmGAPC1 regulatory sequences contained within the pDAB122333 and pDAB122134 constructs, respectively, produced only low levels of expression that was similar to the background (Table 1). These results demonstrate that the de novo isolated GmAct2-2 and GmGAPC1 candidate soybean regulatory sequences were not able to drive RFP/AAD12 transgene expression. Lack of RFP/AAD12 expression in the pDAB122333 and pDAB122134 constructs was not due to poor infiltrations because the second transgene within these constructs, GFP, displayed strong fluorescence that was significantly higher than background ($p<0.0001$). Thus, these results show that the de novo candidate regulatory sequences from Glyma06g15520 and Glyma06g01850 were not capable of driving heterologous reporter transgene expression.

Based on these results, constructs pDAB122333 and pDAB122134 carrying GmAct7-2 and GmGAPC1, respectively, were not pursued further. In contrast, the pDAB122124 construct containing the GmTEFs1 regulatory sequences and exhibiting high constitutive levels of RFP/AAD12 fluorescence, as compared to background of the *N. benthamiana* leaves, was advanced for further testing in stably transformed *Arabidopsis* transgenic plants.

TABLE 1

Results of assaying RFP/AAD12 fluorescence in transiently transformed *N. benthamiana* leaves.

| | | | RFP fluorescence (pixels/area) | | | | GFP fluorescence (pixels/area) | | | |
|---|---|---|---|---|---|---|---|---|---|---|
| Construct | Regulatory Element Name | No. of Samples | Mean | Median | Std Dev | Std Err | Mean | Median | Std Dev | Std Err |
| P19 only | None (Background) | 216 | 26.1 | 24.0 | 14.4 | 1.0 | 34.6 | 33.5 | 14.0 | 1.0 |
| pDAB 117559 | AtUbi14/ AtUbi14 | 261 | 7567.4*** | 6698.4 | 5191.7 | 321.4 | 9770.9*** | 9230.0 | 4609.7 | 285.3 |
| pDAB 117560 | AtUbi10/ AtuOrf23 | 260 | 3084.5*** | 2760.0 | 1984.2 | 123.1 | 8915.9*** | 8737.2 | 5404.7 | 335.2 |
| pDAB 122133 | GmAct7-2/ GmAct7-2 | 60 | 25.3 | 26.4 | 7.0 | 0.9 | 14206.1*** | 12874.3 | 6178.5 | 797.6 |
| pDAB 122134 | GmGAPC1/ GmGAPC1 | 30 | 25.3 | 24.6 | 5.1 | 0.9 | 5295.7*** | 5184.5 | 2085.8 | 380.8 |
| pDAB 122124 | GmTEFs1/ GmTEFs1 | 60 | 1283.3*** | 1236.5 | 785.0 | 101.3 | 6952.7*** | 6294.7 | 4459.6 | 575.7 |

Note:
***indicates RFP or GFP means that are significantly higher ($p < 0.0001$) than the mean background fluorescence.
Due to presence of unequal variances, Welch t-test was used to compare mean RFP or GFP fluorescence of each construct to the corresponding fluorescence means of "P19 only" background control.
Statistical analyses were conducted using JMP ® statistical package.

Results of testing in *N. benthamiana* transient assay are shown in Table 1. Analysis of fluorescence produced by RFP/AAD12 reporter transgene revealed that the GmTEFs1 regulatory sequences resulted in mean RFP fluorescence (1283.3 pixels/area) that was significantly higher ($p<0.0001$) than mean background fluorescence (26.1 pixels/area). It was observed that the RFP/AAD12 fluorescence from the GmTEFs1 regulatory sequences was lower ($p<0.0001$) than the mean RFP/AAD12 fluorescence from the constructs driven by the benchmark regulatory elements of the AtUbi14AtUbi14 and the AtUbi101AtuOrf23; 7567.4 and 3084.5 pixels/area, respectively. The significantly higher than background RFP/AAD12 fluorescence supported by the GmTEFs1 regulatory elements indicated that the GmTEFs1 regulatory sequences from Glyma19g07240 were Example 4: *Agrobacterium*-Mediated Transformation of *Arabidopsis* and Molecular Analyses of Transgenic Events

*Arabidopsis thaliana* ecotype Columbia-0 (Col-0) was used to test the relative expression of RFP/AAD12 reporter under the control of the GmTEFs1 regulatory elements. A standard *Arabidopsis* transformation procedure was used to produce transgenic seed by inflorescence dip method (Clough and Bent, 1998). The $T_1$ seeds were sown on selection trays (10.5"x21"x1", T.O. Plastics Inc., Clearwater, MN). For this, 200 mg of cold stratified seeds (0.1% agar+385 mg/L Liberty for 48 hours before sowing) were distributed on selection trays using a modified air driven spray apparatus to distribute 10 ml of seed suspension per selection tray. Trays were covered with humidity domes, marked with seed identifier, and placed in a Conviron™ with an individual watering tray under each flat. The humidifying dome was removed approximately five days post-sowing. The first watering of selection trays was done using sub-irrigation with Hoagland's fertilizer at approximately 10-14 days post-sowing. In addition to stratification with the herbicide, plants are sprayed with a 0.2% solution (20 µl/10 mL distilled $H_2O$) of Liberty™ herbicide seven and nine days post-sowing. The $T_1$ plants resistant to Liberty™ were transplanted from selection trays into two inch pots and allowed to grow for seven to ten days before sampling for molecular analysis.

Next, DNA was extracted from leaves using an approximately 0.5 square centimeter of *Arabidopsis* leaf that was pinched off each plant. The samples were collected in a 96-well DNA extraction plate. Then 200 µl of extraction buffer was added to each well and tissue was disrupted with three mm stainless steel beads using a Kleko™ tissue pulverizer (three minutes on the maximum setting). After tissue maceration, DNA was isolated using the BioSprint 96 DNA Plant Kit™.

For qPCR, transgene copy number was assayed using hydrolysis probe designed to detect the pat and aad12 genes (Table 2). The *Arabidopsis* endogenous gene, AtTafII15 (*Arabidopsis* Locus: AT4G31720), was used for normalization of DNA template concentration (Table 2). The qPCR was performed as follows: 10 µl of Probes Master Mix™ with a final concentration of 0.4 µM of each primer and 0.2 µM of each probe. The PCR cycles were performed using 95° C. for 10 min, followed by 40 amplification cycles (95° C. for 1 min, 60° C. for 40 sec, and 72° C. for 1 sec) and 40' C for 1 sec. All qPCR assays were run in bi-plex format, with pat or aad12 assays paired with assay for the endogenous gene AtTafII15. The cp scores, the point at which the florescence signal crosses the background threshold using the advanced relative quantification algorithm, based on the ΔΔCt method, (LightCycler® software release 1.5) were used to analyze the real time PCR data. All samples were then calibrated to a known hemizygous plant to obtain the transgene copy number. Up to 100 $T_1$ events that were identified as being resistant to Liberty™ were screened to identify one and two copy transgene events that were used for further analyses of transgene expression in $T_1$ transgenic plants.

TABLE 2

Primers and probes used for genotyping and zygosity analyses of *Arabidopsis* transgenic plants

| Oligo name | Oligo Sequence | Fluorophore label | Target gene |
| --- | --- | --- | --- |
| AtTafII15 F | SEQ ID NO: 13 GAGGATTAGGGTTTCAACGGAG | — | AtTafII15 |
| AtTafII15 R | SEQ ID NO: 14 GAGAATTGAGCTGAGACGAGG | — | AtTafII15 |
| AtTafII15 Probe | SEQ ID NO: 15 AGAGAAGTTTCGACGGATTTCGGGC | HEX | AtTafII15 |
| PAT A primer | SEQ ID NO: 16 ACAAGAGTGGATTGATGATCTAGAGAGGT | — | PAT |
| PAT S primer | SEQ ID NO: 17 CTTTGATGCCTATGTGACACGTAAACAGT | — | PAT |
| PAT_AS probe | SEQ ID NO: 18 AGGGTGTTGTGGCTGGTATTGCTTACGCT | Cy5 | PAT |
| AAD12 F | SEQ ID NO: 19 CAGAGTCCATGCTCACCAAT | — | AAD12 |
| AAD12 R | SEQ ID NO: 20 ACGTGGCAACTTGAAATCC | — | AAD12 |
| AAD12 Probe | SEQ ID NO: 21 TGGAGATGTGGTTGTGTGGGACAA | Cy5 (T1) or FAM (T2) | AAD12 |

Example 5: Evaluation of Genes Operably Linked to GmTEFs1 Regulatory Sequences in T$_1$ Arabidopsis Plants To evaluate expression of the RFP/AAD12 reporter gene driven by the GmTEFs1 promoter, GmTEFs1 5' UTR and GmTEFs1 terminator regulatory elements, single copy transgenic events were identified and assayed for RFP/AAD12 fluorescence using Typhoon instrument. All samples were scanned on three channels: chlorophyll (488 nm blue laser, 670 nm BP30, 580 nm split), GFP (488 nm blue laser, 520 nm BP40, 580 nm split), and RFP (532 nm green laser, 580 nm BP30). The PMT setting for leaf tissue was for chlorophyll 400, GFP 400 and RFP 420. For analyses of fluorescence in leaves, fully expanded rosette leaves from low copy (1-2 copies) transgenic events were harvested from each plant and scanned from adaxial (top) side. The "Contour Draw" function was used to outline leaf shapes and normalized fluorescence was determined by dividing signal volume by surface of the leaf. The results are shown in Table 3.

Analysis of the T$_1$ events for RFP/AAD12 fluorescence revealed that the GmTEFs1 regulatory elements supported high mean RFP/AAD12 fluorescence (804.4 pixels/area) that was statistically higher ($p<0.0001$) than the mean background fluorescence (350.5 pixels/area) detected in the non transgenic wild type control (Wt) (Table 3). These results show that the GmTEFs1 regulatory sequences drove higher than background expression of the RFP/AAD12 reporter in transgenic *Arabidopsis thaliana* plants. The mean RFP/AAD12 fluorescence produced by the GmTEFs1 regulatory elements was lower than RFP/AAD12 fluorescence levels of the pDAB117559 and pDAB117560 benchmark constructs ($p<0.0001$, not shown). In the pDAB117559 and pDAB117560 constructs the RFP/AAD12 reporter was under the control of the following regulatory elements; *Arabidopsis thaliana* Ubiquitin 14 promoter::*Arabidopsis thaliana* Ubiquitin 14 terminator, and the *Arabidopsis thaliana* Ubiquitin 10 promoter::*Agrobacterium tumefaciens* Orf23 terminator, respectively. Although RFP/AAD12 supported fluorescence was lower than that of the positive pDAB117559 and pDAB117560 controls, it was higher than background fluorescence, indicating that GmTEFs1 supports low but statistically higher than background transgene expression. Based on these results the transgenic pDAB122124 events containing the GmTEFs1 regulatory sequences were advanced for further characterization in T$_2$ *Arabidopsis*.

TABLE 3

Results of testing expression of RFP/AAD12 reporter gene/heterologous coding sequence expression in leaves of transgenic T$_1$ *Arabidopsis* plants

| | | | RFP fluorescence | | | | GFP fluorescence | | | |
|---|---|---|---|---|---|---|---|---|---|---|
| Construct | Regulatory Element | No. of events | Mean | Median | Std Dev | Std Err | Mean | Median | Std Dev | Std Err |
| Wt | None (Background) | 57 | 350.5 | 269.3 | 231.4 | 30.7 | 665.2 | 614.1 | 218.0 | 28.9 |
| pDAB 117559 | AtUbi14/ AtUbi14 | 60 | 1492.3*** | 1537.3 | 495.2 | 63.9 | 5164.1*** | 5164.7 | 1605.8 | 207.3 |
| pDAB 117560 | AtUbi10/ AtuOrf23 | 63 | 1547.6*** | 1556.1 | 504.5 | 63.6 | 5521.2*** | 5515.4 | 1434.3 | 180.7 |
| pDAB 122124 | GmTEFs1/ GmTEFs1 | 15 | 804.4*** | 766.7 | 248.9 | 64.3 | 6397.5*** | 6369.5 | 741.0 | 191.3 |

Note:

***indicates means that are different from the mean of the mean fluorescence of the Wt control at $p < 0.0001$.

Due to presence of unequal variances, Welch t-test was used to compare mean RFP or GFP fluorescence of each construct to the corresponding fluorescence means of Wt background control.

Statistical analyses were conducted using JMP ® statistical package.

Example 6: Expression of Genes Operably Linked to GmTEFs1 Regulatory Sequences in Leaves of T$_2$Arabidopsis Plants The GmTEFs1 regulatory sequences exhibited lower, but significantly higher than background, expression levels as compared to the expression levels of the benchmark *Arabidopsis thaliana* Ubiquitin 14 promoter::*Arabidopsis thaliana* Ubiquitin 14 terminator, and the *Arabidopsis thaliana* Ubiquitin 10 promoter::*Agrobacterium tumefaciens* Orf23 terminator regulatory sequences in T$_1$ *Arabidopsis* (EXAMPLE 5). Selected events that contained the GmTEFs1 regulatory sequences driving the RFP/AAD12 reporter gene were advanced for further characterization in T$_2$*Arabidopsis* plants. Accordingly, five T$_1$ plants that expressed from medium to high levels of RFP/AAD12 and GFP were selected. These five plants contained transgenic events of pDAB122124 and were selected for T$_2$ plant testing. From these four events, 56 plants were grown for each event. The T$_2$ plants were molecularly genotyped as described in EXAMPLE 4. Based on molecular analyses, all homozygous and a comparable number of hemizygous plants were retained for fluorescence analysis of the single copy events. To simplify data interpretation for the two copy transgenic events, only hemizygous plants were retained for expression analyses.

The results of analyses in T$_2$ transgenic plants are provided in Table 4. The results for homozygous (1 copy) and hemizygous (1 and 2 copy) events that contained the RFP/AAD12 transgene under the control of GmTEFs1 regulatory elements exhibited RFP/AAD12 fluorescence that was significantly higher than the background fluorescence from non transgenic control plants. While, the mean RFP/AAD12 fluorescence produced by hemizygous and homozygous for a transgene plants carrying the GmTEFs1 regulatory elements was significantly higher than background fluorescence (Table 4), this fluorescence was lower than that of the benchmark pDAB117559 and pDAB117560 constructs ($p<0.0002$, not shown). In the pDAB117559 and pDAB117560 constructs the RFP/AAD12 reporter was under the control of the following regulatory elements; *Arabidopsis thaliana* Ubiquitin 14 promoter::*Arabidopsis thaliana* Ubiquitin 14 terminator, and the *Arabidopsis thaliana* Ubiquitin 10 promoter::*Agrobacterium tumefaciens* Orf23 terminator, respectively. These results demonstrate that the GmTEFs1 regulatory sequences support the robust expression of transgenes in two generations of transgenic events.

TABLE 4

Results of testing expression of RFP/AAD12 reporter gene/heterologous coding sequence expression in leaves of transgenic T$_2$ *Arabidopsis* plants

| Construct | Regulatory Elements | Zygocity | No. of plants | RFP fluorescence (pixels/area) | | | | GFP fluorescence (pixels/area) | | | |
|---|---|---|---|---|---|---|---|---|---|---|---|
| | | | | Mean | Median | Std Dev | Std Err | Mean | Median | Std Dev | Std Err |
| Wt | None (background) | none | 15 | 1137.5 | 1062.9 | 384.0 | 99.2 | 337.0 | 322.8 | 60.3 | 15.6 |
| pDAB 117559 | AtUbi14/ AtUbi14 | hemi | 26 | 10943.2*** | 10394.5 | 2862.0 | 561.3 | 3352.3*** | 3355.0 | 380.2 | 74.6 |
| | | homo | 40 | 17194.3*** | 16208.0 | 6090.0 | 962.9 | 5649.3*** | 6144.2 | 1509.4 | 238.7 |
| pDAB 117560 | AtUbi10/ AtuOrf23 | hemi | 25 | 8239.2*** | 8031.3 | 1928.4 | 385.7 | 3436.3*** | 3312.6 | 674.3 | 134.9 |
| | | homo | 50 | 15334.3*** | 15077.5 | 4080.2 | 577.0 | 6308.3*** | 6152.4 | 1385.5 | 195.9 |
| pDAB 122124 | GmTEFs1/ GmTEFs1 | hemi | 26 | 2127.4*** | 1938.9 | 577.1 | 113.2 | 2602.9*** | 2680.0 | 360.6 | 70.7 |
| | | homo | 13 | 2881.2*** | 2461.5 | 1182.2 | 327.9 | 3867.8*** | 3550.6 | 1210.9 | 335.9 |

Note:

***indicates means that are different from the mean of the mean fluorescence of the Wt control at $p < 0.0001$.

Due to presence of unequal variances, Welch t-test was used to compare mean RFP or GFP fluorescence of each construct to the corresponding fluorescence means of Wt background control.

Statistical analyses were conducted using JMP ® statistical package.

Interrogating the individual transgenic events (Table 5) revealed that RFP/AAD12 fluorescence detected in the two single copy events (pDAB122124-033 and pDAB122124-065) had mean RFP/AAD12 fluorescence that was higher than the mean Wt fluorescence (Table 5). In these single copy transgenic events homozygous plants exhibited higher RFP/AAD12 fluorescence than the hemizygous plants indicating that transgene expression in these events was copy number dependent. Three events that had a complex transgene locus (two copies) also exhibited higher than background RFP/AAD12 fluorescence, although levels of AAD12 expression were lower than that of the homozygous single copy events ($p=0.0091$, not shown), indicating a possibility that complex locus structures, with potential DNA rearrangements, might have impacted RFP/AAD12 expression.

In summary, testing of the transgenic T$_2$ *Arabidopsis* events showed that the GmTEFs1 regulatory elements drive heritable expression of the RFP/AAD12 reporter gene that is higher than Wt background fluorescence. These results reaffirm that the GmTEFs1 regulatory elements are effective in driving heritable transgene expression in stably transformed *Arabidopsis* plants.

TABLE 5

Results of testing expression of RFP/AAD12 reporter gene/heterologous coding sequence expression in leaves of homozygous and hemizygous plants of the individual T₂ Arabidopsis events

| Construct; Regulatory Elements | Event | Zygocity | No. of plants | RFP fluorescence (pixels/area) | | | | GFP fluorescence (pixels/area) | | | |
|---|---|---|---|---|---|---|---|---|---|---|---|
| | | | | Mean | Median | Std Dev | Std Err | Mean | Median | Std Dev | Std Err |
| Col-0 | None (background) | none | 15 | 1137.5 | 1062.9 | 384.0 | 99.2 | 337.0 | 322.8 | 60.3 | 15.6 |
| pDAB 117559; AtUbi14/ AtUbi14 | 117559-057 | hemi | 5 | 10415.0 | 10400.7 | 930.2 | 416.0 | 3529.5 | 3519.1 | 159.8 | 71.5 |
| | | homo | 8 | 17840.7 | 19158.8 | 3743.1 | 1323.4 | 6196.5 | 6607.7 | 1257.6 | 444.6 |
| | 117559-062 | hemi | 6 | 9320.9 | 9586.9 | 808.9 | 330.2 | 3486.9 | 3472.2 | 161.6 | 66.0 |
| | | homo | 9 | 14534.0 | 16156.6 | 3679.1 | 1226.4 | 5455.1 | 6345.2 | 1482.7 | 494.2 |
| | 117559-246 | hemi | 5 | 14037.8 | 13650.2 | 1112.2 | 497.4 | 3351.0 | 3316.9 | 488.5 | 218.4 |
| | | homo | 9 | 23442.5 | 25126.5 | 5547.1 | 1849.0 | 5724.0 | 5870.9 | 1573.9 | 524.6 |
| | 117559-314 | hemi | 5 | 13987.2 | 13806.8 | 1671.9 | 747.7 | 3411.0 | 3489.6 | 465.9 | 208.3 |
| | | homo | 4 | 21176.8 | 20884.0 | 7321.8 | 3660.9 | 5296.8 | 5217.0 | 2391.4 | 1195.7 |
| | 117559-391 | hemi | 5 | 7279.7 | 7364.9 | 922.8 | 412.7 | 2956.2 | 3020.1 | 350.4 | 156.7 |
| | | homo | 10 | 11855.0 | 12938.5 | 2711.7 | 857.5 | 5459.9 | 5750.6 | 1475.0 | 466.4 |
| pDAB 117560; AtUbi10/ AtuOrf23 | 117560-191 | hemi | 5 | 8889.2 | 9549.1 | 2092.5 | 935.8 | 3831.1 | 4015.2 | 859.5 | 384.4 |
| | | homo | 10 | 15330.1 | 14866.4 | 4404.6 | 1392.9 | 6352.1 | 6030.2 | 1756.8 | 555.6 |
| | 117560-254 | hemi | 5 | 9158.7 | 8167.0 | 2264.3 | 1012.6 | 3611.3 | 3358.9 | 664.3 | 297.1 |
| | | homo | 10 | 14704.1 | 14959.2 | 4009.6 | 1267.9 | 6283.7 | 6343.9 | 1273.8 | 402.8 |
| | 117560-288 | hemi | 5 | 6506.8 | 6287.3 | 948.7 | 424.3 | 3066.4 | 3136.1 | 256.9 | 114.9 |
| | | homo | 10 | 18550.4 | 18921.9 | 3158.6 | 998.8 | 7007.3 | 6673.1 | 1175.3 | 371.7 |
| | 117560-325 | hemi | 5 | 7716.5 | 6838.0 | 1951.7 | 872.8 | 3172.3 | 3092.6 | 668.9 | 299.1 |
| | | homo | 10 | 14238.9 | 13152.0 | 4636.8 | 1466.3 | 6230.7 | 5924.0 | 1444.7 | 456.9 |
| | 117560-353 | hemi | 5 | 8924.7 | 8444.1 | 1354.0 | 605.5 | 3500.2 | 3459.6 | 733.6 | 328.1 |
| | | homo | 10 | 13848.3 | 13274.9 | 2821.9 | 892.4 | 5667.9 | 5782.0 | 1125.1 | 355.8 |
| pDAB 122124; GmTEFs1/ GmTEFs1 | 122124-195 (two copy event) | hemi | 5 | 1956.82*** | 1845.9 | 184.2 | 82.4 | 2776.7*** | 2832.6 | 192.3 | 86.0 |
| | 122124-033 | hemi | 6 | 2997.42*** | 3050.55 | 366.7 | 149.7 | 2453.8*** | 2420.2 | 470.9 | 192.28 |
| | | homo | 5 | 3760.4** | 3670.8 | 1316.1 | 588.6 | 4041.2*** | 4202.9 | 1114.1 | 498.2 |
| | 122124-049 (two copy event) | hemi | 5 | 1758.7* | 1861.3 | 391.9 | 175.3 | 2554.1*** | 2703.2 | 461.1 | 206.2 |
| | 122124-065 | hemi | 5 | 1894.8* | 1813.6 | 420.2 | 187.9 | 2627.3*** | 2745.3 | 325.9 | 145.7 |
| | | homo | 8 | 2331.6* | 2246.7 | 713.2 | 252.2 | 3759.4*** | 3301.1 | 1330.3 | 470.3 |
| | 122124-117 (two copy event) | hemi | 5 | 1855.3*** | 1817.8 | 217.0 | 97.0 | 2632.2*** | 2656.7 | 322.0 | 144.0 |

Note:
Statistical analyses of mean RFP and GFP fluorescence of individual pDAB122124 events were conducted separately for each zygocity class.
Due to the small sample sizes and presence of unequal variances, Welch t-test was used to compare mean RFP or GFP fluorescence of each event to the mean of Wt control fluorescence.
Stars indicate mean RFP and GFP fluorescence of pDAB122124 transgenic events (hemizygous or heterozygous) that is significantly higher than the mean fluorescence of the Wt control; *—p values that are equal or smaller than 0.0002, —p values are smaller than 0.001 and *—p values that equal or smaller than 0.01.
Statistical analyses were done using JMP ® statistical package.

Example 7: Soybean Transgenic Plants Production and Transgene Copy Number Estimation Using Real Time TaqMan® PCR The GmTEFs1 regulatory elements (pDAB122124) were further tested in transgenic soybean plants. Transgenic soybean plants were produced using the split seed transformation method described in Pareddy et al., US 2014/0173774 A1, herein incorporated by reference in its entirety. Transgenic plantlets were analyzed molecularly to determine transgene copy number. For this, leaf tissue samples from transgenic soybean plants and non-transgenic controls were collected in 96-well collection tubes. Tissue disruption was performed using tungsten 2 mm beads. Following tissue maceration, the genomic DNA was isolated in high throughput format using the MagAttract Plant kit™ (Qiagen, Hilden, Germany) on the Agilent BioCel™. The transgenic copy number of PAT was determined by using a hydrolysis probe assay, analogous to TaqMan® assay, in bi-plex with a soybean internal reference gene, GMS116 (GMFL01-25-J19 of Genbank Accession No: AK286292.1). The assays were designed using the LightCycler© Probe Design Software 2.0. The transgenic presence/absence of Spectinomycin resistance gene (SpecR) was determined by using a hydrolysis probe assay, analogous to TaqMan® assay, in bi-plex with a soybean internal reference gene, GMS116. This assay was designed to detect the SpecR gene located within the backbone of the binary constructs used for transformation. Only events in which there was no amplification with SpecR probe were regenerated because this indicated that backbone fragments were not likely to be present in the transgenic soybean genome. For amplification of all genes of interest (PAT, SpecR,GMS116), LightCycler® 480 Probes Master mix™ (Roche Applied Science) was prepared at a 1× final concentration in a 10 µL volume multiplex reaction containing 0.4 µM of each primer and 0.2 µM of each probe (composition of primers and probes listed in TABLE 7). A two-step amplification reaction was performed using the LIGHTCYCLER 480 system™ (Roche Applied Science), with an extension at 60° C. for 60 seconds with fluorescence acquisition.

Analysis of real time PCR data was performed using LightCycler® software release 1.5 using the advanced relative quant module and was based on the ΔΔCt method. For PAT, a sample of known single copy gDNA was included in each run and was used as a single copy calibrator. In addition, each run, for all genes of interest, included a wild-type (Maverick) sample as a negative control.

TABLE 6

Primer and Probe Information for hydrolysis probe assay of PAT and SpecR genes located in the backbone and internal reference (GMS116). All sequences are indicated 5'-3'.

| OLIGO | SEQUENCE | TYPE |
|---|---|---|
| PATF | ACAAGAGTGGATTGATGATCTAGAGA (SEQ ID NO: 22) | Primer |
| PATR | CTTTGATGCCTATGTGACACGTAAAC (SEQ ID NO: 23) | Primer |
| PAT PR | 6FAM-CCAGCGTAAGCAATACCAGCCACAACACC-3BHQ_1 (SEQ ID NO: 24) | Hydrolysis probe |
| SpecR F | CGCCGAAGTATCGACTCAACT (SEQ ID NO: 25) | Primer |
| SpecR R | GCAACGTCGGTTCGAGATG (SEQ ID NO: 26) | Primer |
| SpecR PR | 6FAM-TCAGAGGTAGTTGGCGTCATCGAG-3BHQ_1 (SEQ ID NO: 27) | Hydrolysis probe |

Example 8: Evaluation of the GmTEFs1 Regulatory Sequences Expression in $T_1$ Soybean Plants The expression of genes by the GmTEFs1 regulatory elements was tested in soybean transgenic plants. For this analysis stable transformation of soybean plants were generated as described in EXAMPLE 7. Transgenic plantlets carrying low transgene copy number (1-2 copies) from the GmTEFs1 regulatory elements construct (pDAB122124) and the control benchmark construct (pDAB117560) transformations were regenerated, and $T_1$ seeds were collected and used for planting in greenhouse. The $T_1$ soybean plants were grown in greenhouse and genotyped for transgene as described in EXAMPLE 7.

To evaluate expression of the RFP/AAD12 reporter gene driven by the GmTEFs1 promoter, GmTEFs1 5' UTR and GmTEFs1 terminator regulatory elements, transgenic plants were identified and assayed for RFP/AAD12 fluorescence using Typhoon instrument. All samples were scanned on three channels: chlorophyll (488 nm blue laser, 670 nm BP30, 580 nm split), GFP (488 nm blue laser, 520 nm BP40, 580 nm split), and RFP (532 nm green laser, 580 nm BP30). The PMT setting for leaf tissue was for chlorophyll 400, GFP 400 and RFP 420. Leaves were collected at V3 soybean plants from the topmost fully expanded leaf. For scanning, three leaf disks were cut out of each collected leaf. The fluorescence results of the RFP/AAD12 and GFP reporter genes are shown in Table 7. The expression of the reporter gene driven by the GmTEFs1 regulatory sequences was robust (1507.5 pixels/area for hemizygous and 2674.2 pixels/area for homozygous plants) and highly significant above background (613.1 pixels/area, p<0.0001, Table 7). The mean RFP/AAD12 fluorescence specified by the hemizygous and homozygous pDAB122124 plants carrying GmTEFs1 regulatory sequences was lower that of RFP/AAD12 driven by the *Arabidopsis thaliana* Ubiquitin 10 promoter::*Agrobacterium tumefaciens* Orf23 terminator (p<0.0001 for hemizygous and homozygous plans, not shown). Although expression of GmTEFs1 driven RFP/AAD12 was lower than that of the control, this expression level is sufficient for reliable transgene expression in $T_1$ soybean.

TABLE 7

Results of testing expression of RFP/AAD12 reporter gene/heterologous coding sequence expression in leaves of soybean single copy $T_1$ transgenic events

| Construct | Regulatory Elements | Consensus zygocity | No. of plants | No. of leaf disks scanned | RFP fluorescence (pixels/area) | | | | GFP fluorescence (pixels/area) | | | |
|---|---|---|---|---|---|---|---|---|---|---|---|---|
| | | | | | Mean | Median | Std Dev | Std Err | Mean | Median | Std Dev | Std Err |
| Wt | Maverick | Null | 4 | 12 | 613.1 | 608.8 | 64.5 | 18.6 | 235.4 | 238.0 | 11.6 | 3.3 |
| pDAB 117560 | AtUbi10/ AtuOrf23 | Hemi | 12 | 36 | 3075.6*** | 3055.5 | 1036.4 | 172.7 | 2084.2*** | 2072.2 | 377.3 | 62.9 |
| | | Homo | 11 | 33 | 4559.2*** | 4300.7 | 2059.8 | 358.6 | 4085.2*** | 4308.5 | 1094.8 | 190.6 |
| pDAB 122124 | GmTEFs1/ GmTEFs1 | Hemi | 24 | 72 | 1507.5*** | 1263.5 | 723.0 | 85.2 | 992.2*** | 655.9 | 833.4 | 98.2 |
| | | Homo | 23 | 69 | 2674.2*** | 2337.1 | 1305.3 | 157.1 | 2019.3*** | 320.4 | 1877.9 | 226.1 |

Note:

***indicates means that are different from the mean of the mean fluorescence of the Wt control at p < 0.0001.

Due to presence of unequal variances, Welch t-test was used to compare mean RFP or GFP fluorescence of each construct to the corresponding fluorescence means of Wt background control.

Statistical analyses were conducted using JMP ® statistical package.

Interrogating the individual soybean transgenic events (Table 8) revealed that RFP/AAD12 fluorescence was detected in all four single copy events that were assayed. For all transgenic events homozygous plants exhibited higher RFP/AAD12 fluorescence than the hemizygous siblings, thereby indicating that transgene expression in these events was copy number dependent.

In summary, testing of the transgenic $T_1$ Soybean events showed that the GmTEFs1 regulatory elements drive heritable expression of the RFP/AAD12 reporter gene that is higher than the Wt background in multiple independent transgenic events. These results reaffirm that the GmTEFs1 regulatory elements are effective in driving heritable transgene expression in stably transformed soybean plants.

Rice may be transformed with genes operably linked to the GmTEFs1 promoter, the GmTEFs1 5' UTR, the GmTEFs1 3' UTR and/or the GmTEFs1 terminator by utilizing the same techniques previously described in Example #19 of patent application WO 2013/116700A1 (Lira et al.)

Example 10: *Agrobacterium*-Mediated Transformation of Genes Operably Linked to the GmTEFs1 Regulatory Elements In light of the subject disclosure, additional crops can be transformed according to embodiments of the subject disclosure using techniques that are known in the art. For

TABLE 8

Results of testing expression of RFP/AAD12 reporter gene/heterologous coding sequence expression in leaves of homozygous and hemizygous plants of the individual T2 soybean events

| Construct | Regulatory Elements | Event | Consensus zygocity | No. of plants | No. of leaf disks | RFP fluorescence (pixels/area) | | | | GFP fluorescence (pixels/area) | | | |
|---|---|---|---|---|---|---|---|---|---|---|---|---|---|
| | | | | | | Mean | Median | Std Dev | Std Err | Mean | Median | Std Dev | Std Err |
| Maverick | None | none | Null | 4 | 12 | 613.1 | 608.8 | 64.5 | 18.6 | 235.4 | 238.0 | 11.6 | 3.3 |
| pDAB 117560 | AtUbi10/ AtuOrf23 | 117560-670 | Hemi | 6 | 18 | 2463.2*** | 2562.1 | 805.5 | 189.9 | 1941.5*** | 1875.1 | 439.1 | 103.5 |
| | | | Homo | 6 | 18 | 4002.2*** | 3884.2 | 1918.3 | 452.2 | 3631.2*** | 3829.9 | 1203.8 | 283.7 |
| | | 117560-691 | Hemi | 6 | 18 | 3687.9*** | 3528.3 | 876.8 | 206.7 | 2226.9*** | 2172.5 | 239.0 | 56.3 |
| | | | Homo | 5 | 15 | 5227.6 | 4562.0 | 2086.1 | 538.6 | 4630.0 | 4616.6 | 630.0 | 162.7 |
| pDAB 122124 | GmTEFs1/ GmTEFs1 | 122124-213 | Hemi | 6 | 18 | 2450.0*** | 2329.2 | 744.7 | 175.5 | 2128.5*** | 2067.5 | 291.7 | 68.7 |
| | | | Homo | 6 | 18 | 2715.8*** | 2760.2 | 441.1 | 104.0 | 3979.9*** | 4009.2 | 524.1 | 123.5 |
| | | 122124-220 | Hemi | 6 | 18 | 1066.0*** | 1034.1 | 286.1 | 67.4 | 221.1*** | 231.0 | 30.1 | 7.1 |
| | | | Homo | 6 | 18 | 1852.7*** | 1562.6 | 705.5 | 166.3 | 243.7*** | 239.6 | 19.7 | 4.7 |
| | | 122124-221 | Hemi | 6 | 18 | 1137.6*** | 1210.5 | 251.8 | 59.3 | 265.0*** | 270.9 | 58.7 | 13.8 |
| | | | Homo | 6 | 18 | 2470.4*** | 2088.6 | 1022.5 | 241.0 | 295.4*** | 302.2 | 22.6 | 5.3 |
| | | 122124-230 | Hemi | 6 | 18 | 1376.3*** | 1263.5 | 416.6 | 98.2 | 1354.1*** | 1262.3 | 340.1 | 80.2 |
| | | | Homo | 5 | 15 | 3854.5*** | 3228.0 | 1936.3 | 500.0 | 3865.9*** | 3709.8 | 568.0 | 146.7 |

Note:
***indicates means that are different from the mean of the mean fluorescence of the Wt control at $p < 0.0001$.
Due to presence of unequal variances, Welch t-test was used to compare mean RFP or GFP fluorescence of each construct to the corresponding fluorescence means of Wt background control.
Statistical analyses were conducted using JMP ® statistical package.

Example 9: *Agrobacterium*-Mediated Transformation of Genes Operably Linked to the GmTEFs1 Promoter, the GmTEFs1 5' UTR, the GmTEFs1 3' UTR and/or the GmTEFs1 Terminator Soybean may be transformed with genes operably linked to the GmTEFs1 promoter, the GmTEFs1 5' UTR, the GmTEFs1 3' UTR and/or the GmTEFs1 terminator by utilizing the same techniques previously described in Example #11 or Example #13 of patent application WO 2007/053482.

Cotton may be transformed with genes operably linked to the GmTEFs1 promoter, the GmTEFs1 5' UTR, the GmTEFs1 3' UTR and/or the GmTEFs1 terminator by utilizing the same techniques previously described in Examples #14 of U.S. Pat. No. 7,838,733 or Example #12 of patent application WO 2007/053482 (Wright et al.).

Canola may be transformed with genes operably linked to the GmTEFs1 promoter, the GmTEFs1 5' UTR, the GmTEFs1 3' UTR and/or the GmTEFs1 terminator by utilizing the same techniques previously described in Example #26 of U.S. Pat. No. 7,838,733 or Example #22 of patent application WO 2007/053482 (Wright et al.)

Wheat may be transformed with genes operably linked to the GmTEFs1 promoter, the GmTEFs1 5' UTR, the GmTEFs1 3' UTR and/or the GmTEFs1 terminator by utilizing the same techniques previously described in Example #23 of patent application WO 2013/116700A1 (Lira et al.)

*Agrobacterium*-mediated transformation of rye, see, e.g., Popelka J C, Xu J, Altpeter F., "Generation of rye with low transgene copy number after biolistic gene transfer and production of (*Secale cereale* L.) plants instantly marker-free transgenic rye," *Transgenic Res.* 2003 October; 12(5): 587-96). For *Agrobacterium*-mediated transformation of sorghum, see, e.g., Zhao et al., "*Agrobacterium*-mediated sorghum transformation," Plant Mol Biol. 2000 December; 44(6):789-98. For *Agrobacterium*-mediated transformation of barley, see, e.g., Tingay et al., "*Agrobacterium tumefaciens*-mediated barley transformation," The Plant Journal, (1997) 11: 1369-1376. For *Agrobacterium*-mediated transformation of wheat, see, e.g., Cheng et al., "Genetic Transformation of Wheat Mediated by *Agrobacterium tumefaciens*," *Plant Physiol.* 1997 November; 115(3):971-980. For *Agrobacterium*-mediated transformation of rice, see, e.g., Hiei et al., "Transformation of rice mediated by *Agrobacterium tumefaciens*," *Plant Mol. Biol.* 1997 September; 35(1-2):205-18.

The Latin names for these and other plants are given below. It should be clear that other (non-*Agrobacterium*) transformation techniques can be used to transform genes operably linked to GmTEFs1 promoter, the GmTEFs1 5' UTR, the GmTEFs1 3' UTR and/or the GmTEFs1 terminator, for example, into these and other plants. Examples include, but are not limited to; Maize (*Zea mays*), Wheat (*Triticum* spp.), Rice (*Oryza* spp. and *Zizania* spp.), Barley (*Hordeum* spp.), Cotton (*Abroma augusta* and *Gossypium* spp.), Soybean (*Glycine max*), Sugar and table beets (Beta spp.), Sugar cane (*Arenga pinnata*), Tomato (*Lycopersicon esculentum* and other spp., *Physalis ixocarpa, Solanum incanum* and other spp., and *Cyphomandra betacea*), Potato (*Solanum tuberosum*), Sweet potato (*Ipomoea batatas*), Rye (*Secale* spp.), Peppers (*Capsicum annuum, chinense,* and *frutescens*), Lettuce (*Lactuca sativa, perennis,* and *pulchella*), Cabbage (*Brassica* spp.), Celery (*Apium graveolens*), Eggplant (*Solanum melongena*), Peanut (*Arachis hypogea*), Sorghum (*Sorghum* spp.), Alfalfa (*Medicago sativa*), Carrot (*Daucus carota*), Beans (*Phaseolus* spp. and other genera), Oats (*Avena sativa* and *strigosa*), Peas (*Pisum, Vigna,* and *Tetragonolobus* spp.), Sunflower (*Helianthus annuus*), Squash (*Cucurbita* spp.), Cucumber (*Cucumis sativa*), Tobacco (*Nicotiana* spp.), Arabidopsis (*Arabidopsis thaliana*), Turfgrass (*Lolium, Agrostis, Poa, Cynodon,* and other genera), Clover (*Trifolium*), Vetch (*Vicia*). Transformation of such plants, with genes operably linked to the GmTEFs1 promoter, the GmTEFs1 5' UTR, the GmTEFs1 3' UTR and/or the GmTEFs1 terminator, for example, is contemplated in embodiments of the subject disclosure.

Use of the GmTEFs1 promoter, the GmTEFs1 5' UTR, the GmTEFs1 3' UTR and/or the GmTEFs1 terminator to drive operably linked genes can be deployed in many deciduous and evergreen timber species. Such applications are also within the scope of embodiments of this disclosure. These species include, but are not limited to; alder (*Alnus* spp.), ash (*Fraxinus* spp.), aspen and poplar species (*Populus* spp.), beech (*Fagus* spp.), birch (*Betula* spp.), cherry (*Prunus* spp.), eucalyptus (*Eucalyptus* spp.), hickory (*Carya* spp.), maple (Acer spp.), oak (*Quercus* spp.), and pine (*Pinus* spp.).

Use of GmTEFs1 promoter, the GmTEFs1 5' UTR, the GmTEFs1 3' UTR and/or the GmTEFs1 terminator to drive operably linked genes can be deployed in ornamental and fruit-bearing species. Such applications are also within the scope of embodiments of this disclosure. Examples include, but are not limited to; rose (Rosa spp.), burning bush (*Euonymus* spp.), petunia (*Petunia* spp.), begonia (*Begonia* spp.), rhododendron (*Rhododendron* spp.), crabapple or apple (Malus spp.), pear (*Pyrus* spp.), peach (*Prunus* spp.), and marigolds (*Tagetes* spp.).

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A nucleic acid vector comprising a 3' UTR operably linked to: a) a heterologous polylinker sequence; or b) a non-GmTEFs1 polynucleotide sequence, wherein said 3' UTR comprises a polynucleotide sequence that has at least 97% sequence identity with SEQ ID NO:4.

2. The nucleic acid vector of claim 1, wherein said 3' UTR is 739 bp in length.

3. The nucleic acid vector of claim 1, wherein said 3' UTR consists of a polynucleotide sequence that has at least 97% sequence identity with SEQ ID NO:4.

4. The nucleic acid vector of claim 1, further comprising a sequence encoding a selectable maker.

5. The nucleic acid vector of claim 1, wherein said non-GmTEFs1 polynucleotide sequence is a transgene.

6. The nucleic acid vector of claim 5, wherein the transgene encodes a selectable marker or a gene product conferring insecticidal resistance, herbicide tolerance, expression of an RNAi, nitrogen use efficiency, water use efficiency, or nutritional quality.

7. The nucleic acid vector of claim 1, further comprising a promoter polynucleotide sequence of SEQ ID NO:2, wherein the promoter sequence is operably linked to said polylinker or said non-GmTEFs1 polynucleotide sequence.

8. The nucleic acid vector of claim 7, further comprising an intron sequence.

9. The nucleic acid vector of claim 7, wherein said promoter has tissue preferred specific expression.

\* \* \* \* \*